(12) United States Patent
Morinaga et al.

(10) Patent No.: US 11,286,286 B2
(45) Date of Patent: Mar. 29, 2022

(54) METHOD AND DEVICE FOR MANUFACTURING PROTEIN FIBER

(71) Applicants: Spiber Inc., Yamagata (JP); Kojima Industries Corporation, Aichi (JP)

(72) Inventors: Takashi Morinaga, Tsuruoka (JP); Takehisa Maekawa, Tsuruoka (JP)

(73) Assignees: Spiber Inc., Yamagata (JP); Kojima Industries Corporation, Aichi (JP)

( * ) Notice: Subject to any disclaimer, the term of this patent is extended or adjusted under 35 U.S.C. 154(b) by 132 days.

(21) Appl. No.: 16/491,633

(22) PCT Filed: Mar. 5, 2018

(86) PCT No.: PCT/JP2018/008198
§ 371 (c)(1),
(2) Date: Sep. 6, 2019

(87) PCT Pub. No.: WO2018/164020
PCT Pub. Date: Sep. 13, 2018

(65) Prior Publication Data
US 2020/0031886 A1 Jan. 30, 2020

(30) Foreign Application Priority Data
Mar. 10, 2017 (JP) .............................. JP2017-046519

(51) Int. Cl.
*D01D 5/06* (2006.01)
*D01D 5/14* (2006.01)
(Continued)

(52) U.S. Cl.
CPC .......... *C07K 14/43518* (2013.01); *D01F 4/02* (2013.01); *D02J 1/222* (2013.01);
(Continued)

(58) Field of Classification Search
CPC .. D01D 5/06; D01D 5/14; D01D 7/00; D01D 10/02; D01F 4/00; D02J 1/22;
(Continued)

(56) References Cited

U.S. PATENT DOCUMENTS

| 2003/0155670 A1 | 8/2003 | O'Brien |
| 2009/0318963 A1 | 12/2009 | Asakura |

(Continued)

FOREIGN PATENT DOCUMENTS

| CN | 102808237 A | 12/2012 |
| CN | 104395511 A | 3/2015 |

(Continued)

OTHER PUBLICATIONS

Extended European Search Report issued in counterpart European Patent Application No. 18764885.2 dated Nov. 10, 2020.

(Continued)

*Primary Examiner* — Leo B Tentoni
(74) *Attorney, Agent, or Firm* — Morgan, Lewis & Bockius LLP

(57) ABSTRACT

The present invention relates to a method for manufacturing a protein fiber, including an extension and contraction step of contracting or extending a protein raw fiber containing a protein by bringing the protein raw fiber into contact with a liquid or vapor; and a drying step of drying the protein raw fiber that has undergone the extension and contraction step while adjusting a length of the protein raw fiber to an arbitrary length.

18 Claims, 5 Drawing Sheets
Specification includes a Sequence Listing.

(51) Int. Cl.

| | |
|---|---|
| *D01D 7/00* | (2006.01) |
| *D01D 10/02* | (2006.01) |
| *D01F 4/00* | (2006.01) |
| *D02J 1/22* | (2006.01) |
| *D02J 13/00* | (2006.01) |
| *D04H 3/015* | (2012.01) |
| *D06B 3/04* | (2006.01) |
| *D06M 11/05* | (2006.01) |
| *D06M 11/84* | (2006.01) |
| *F26B 13/00* | (2006.01) |
| *F26B 13/12* | (2006.01) |
| *C07K 14/435* | (2006.01) |
| *D01F 4/02* | (2006.01) |
| *D06M 101/10* | (2006.01) |

(52) U.S. Cl.
CPC ............ *D02J 1/223* (2013.01); *D02J 1/229* (2013.01); *D06M 2101/10* (2013.01); *D10B 2211/22* (2013.01)

(58) Field of Classification Search
CPC .. D02J 1/222; D02J 1/223; D02J 1/229; D02J 13/00; D04H 3/015; D06B 3/04; D06M 11/05; D06M 11/84; D06M 2101/10; D10B 2211/22; F26B 13/00; F26B 13/12
USPC ... 264/103, 202, 210.3, 210.4, 210.5, 210.8, 264/211.12, 211.14, 211.15, 234, 288.4, 264/289.6, 290.5, 290.7, 342 RE, 345; 425/66, 71, 378.2, 445; 28/220, 240; 34/381, 623; 68/5 D, 175
See application file for complete search history.

(56) References Cited

U.S. PATENT DOCUMENTS

| | | | |
|---|---|---|---|
| 2014/0058066 A1* | 2/2014 | Sekiyama | ............... D01D 5/06 530/353 |
| 2015/0141618 A1 | 5/2015 | Ishikawa et al. | |
| 2018/0216260 A1* | 8/2018 | Breslauer | ................. D01F 4/00 |

FOREIGN PATENT DOCUMENTS

| | | | | |
|---|---|---|---|---|
| EP | 0015143 A1 | 9/1980 | | |
| EP | 2868782 A1 | 5/2015 | | |
| GB | 954824 A | * 4/1964 | ............ | D02J 1/229 |
| JP | S55-142759 A | 11/1980 | | |
| JP | H01-183534 A | 7/1989 | | |
| JP | H02-006869 A | 2/1990 | | |
| JP | H03-213565 A | 9/1991 | | |
| JP | H06-294068 A | 10/1994 | | |
| JP | H07-207520 A | 8/1995 | | |
| JP | 3722708 B2 | 11/2005 | | |
| JP | 2009-155774 A | 7/2009 | | |
| JP | 2013-506058 A | 2/2013 | | |
| WO | 2011/038401 A2 | 3/2011 | | |
| WO | 2012/165476 A1 | 12/2012 | | |
| WO | 2012/165477 A1 | 12/2012 | | |
| WO | 2014/037453 A1 | 3/2014 | | |
| WO | 2018/087239 A1 | 5/2018 | | |

OTHER PUBLICATIONS

International Search Report issued in corresponding International Patent Application No. PCT/JP2018/008198 dated May 29, 2018.
International Preliminary Report on Patentability and Written Opinion issued in corresponding International Patent Application No. PCT/JP2018/008198 dated Sep. 19, 2019.
Communication issued in counterpart European Patent Application No. 18764885.2 dated Dec. 6, 2021.

* cited by examiner

Fig.5
(a)
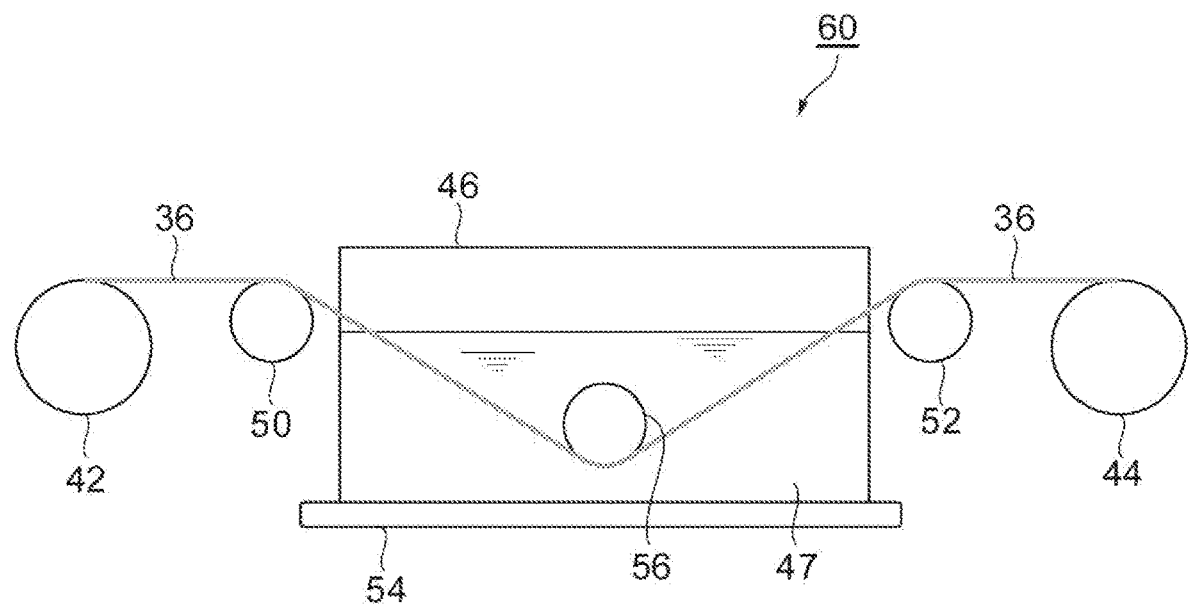
(b)
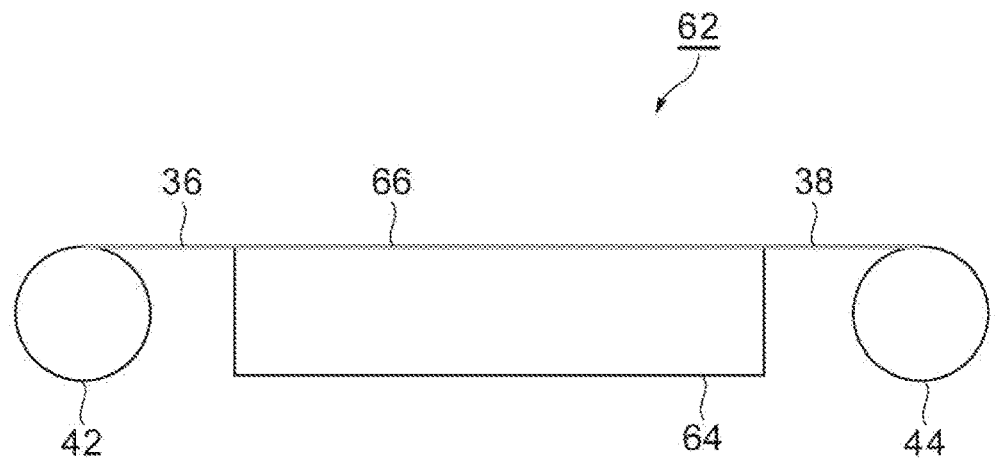

METHOD AND DEVICE FOR MANUFACTURING PROTEIN FIBER

SEQUENCE LISTING SUBMISSION VIA EFS-WEB

A computer readable text file, entitled "SequenceListing.txt," created on or about Sep. 6, 2019 with a file size of about 151 kb contains the sequence listing for this application and is hereby incorporated by reference in its entirety.

TECHNICAL FIELD

The present invention relates to a method and a device for manufacturing a protein fiber. The present invention also relates to a method for processing a protein fiber and a method for manufacturing fabric made of protein fibers.

BACKGROUND ART

In the related art, protein fibers such as silk and wool have been widely used as materials for clothing, bedding, and the like by utilizing their excellent tactile properties and heat retention properties. In addition, spider silks having excellent strength and high elasticity have attracted attention recently, and research toward practical applications of artificial spider silks having the characteristics of these spider silks are actively conducted. Artificial spider silks are not only examined to be applied to clothing but also examined as various materials such as industrial materials and medical materials that require high strength and high toughness. Furthermore, these protein fibers, unlike synthetic fibers, are biodegradable and require less energy for manufacture and processing. Therefore, a demand thereof is expected to increase in accordance with an increase in environmental conservation awareness in recent years.

Meanwhile, as is well known, some protein fibers are contracted upon contact with moisture (for example, immersion in water or hot water, or exposure to a high-humidity environment). In addition, depending on the type of protein fiber, the manner of manufacture, and the like, protein fibers are considered to be extended upon contact with moisture. In a case where an unexpected length change such as contraction and extension upon contact with moisture in such protein fibers occurs when the protein fibers are brought into contact with moisture for the first time after manufacture, there are concerns that various problems may be caused thereby. For example, in a case where protein fibers are exposed to high-humidity environment during storage immediately after manufacture, or in case where an unexpected length change occurs when a process using moisture, such as cleaning and wet heat setting, is performed for the first time after manufacture, there is a possibility of not only a deterioration in workability and quality, but also adverse effects to post-processing.

Under such circumstances, Patent Literature 1 discloses a method for pre-shrinking woven fabric (silk woven fabric) using silk, which is a kind of protein fiber. This method prevents contraction of silk fabric at a processing stage such as dyeing by immersing silk fabric, which is so-called crepe formed of strong twisted yarn after scouring, in water and heating it in a state where it is tensioned and fixed such that it is not contracted. However, because such a pre-shrinking method is intended for pre-shrinkage of woven fabric made of a special silk thread, which had been already brought into contact with moisture at the time of scouring, and which is formed of strong twisted yarn, it was difficult to say that this method is effective in contraction of a protein fiber itself when it is brought into contact with moisture for the first time after manufacture, and in prevention of an unexpected length change including extension.

In addition, Patent Literature 2 discloses a method for manufacturing an animal hair fiber having excellent pre-shrinkage resistance. Although this method is intended for pre-shrinkage of a protein fiber, because oxidation-reduction treatment with respect to an S—S bond present within an animal hair fiber is performed in multiple stages, complication in manufacturing steps was inevitable.

CITATION LIST

Patent Literature

[Patent Literature 1] Japanese Examined Patent Publication No. H2-6869
[Patent Literature 2] Japanese Patent No. 3722708

SUMMARY OF INVENTION

Problems to be Solved by the Invention

In view of the above-mentioned problems of the related art, an object of the present invention is to provide a method and a device which can more easily manufacture a protein fiber in which an unexpected length change when a fiber is brought into contact with moisture for the first time after manufacture can be prevented. In addition, another object of the present invention is to provide a method for processing a protein fiber which can prevent, as much as possible, an unexpected length change when a fiber is brought into contact with moisture for the first time after manufacture; and a method for easily manufacturing fabric made of protein fibers which is obtained by using such a protein fiber.

Means for Solving the Problems

As a result of intensive studies to solve the above-mentioned problems, the inventors of the present invention have found that, by drying a protein raw fiber while adjusting a length of the protein raw fiber to an arbitrary length after naturally contracting or extending the protein raw fiber by, without external force, bringing the protein raw fiber into contact with moisture and the like and allowing the moisture and the like to enter between protein raw fibers or within the fiber, it is possible to control a length of a protein raw fiber when it is brought into contact with moisture for the first time after manufacture by an amount corresponding to an amount of an adjusted length during drying. The present invention is based on these findings.

That is, the present invention relates to a method for manufacturing a protein fiber, including an extension and contraction step of contracting or extending a protein raw fiber containing a protein by bringing the protein raw fiber into contact with a liquid or vapor; and a drying step of drying the protein raw fiber that has undergone the extension and contraction step while adjusting a length of the protein raw fiber to an arbitrary length.

In the manufacturing method of the present invention, the extension and contraction step may be a step of naturally contracting the protein raw fiber by bringing the protein raw fiber into contact with the liquid or vapor (hereinafter will be referred to as the "contraction step").

In the manufacturing method of the present invention, the extension and contraction step may be performed in a state where the protein raw fiber is not loosened.

In the manufacturing method of the present invention, in the extension and contraction step, the protein raw fiber may be tensioned such that a contraction amount of the protein raw fiber is substantially the same as a contraction amount of the protein raw fiber in a case where the protein raw fiber is naturally contracted by being brought into contact with the liquid or vapor in a state where the protein raw fiber is loosened.

In the manufacturing method of the present invention, the protein may be a structural protein.

In the manufacturing method of the present invention, the structural protein may be a spider silk fibroin.

In the manufacturing method of the present invention, the liquid may be a warmed liquid.

In the manufacturing method of the present invention, the extension and contraction step may be performed by immersing the protein raw fiber in the liquid.

In the manufacturing method of the present invention, the liquid or vapor may have a polarity.

In the manufacturing method of the present invention, the liquid may be water or hot water, and the vapor may be water vapor.

In the manufacturing method of the present invention, the extension and contraction step and the drying step may be performed with respect to the protein raw fiber fed continuously, and the method further comprises a step of continuously winding a protein fiber obtained through the extension and contraction step and the drying step. In this case, a speed at which the protein fiber is wound may be slower than a speed at which the protein raw fiber is fed, and may be a speed at which the protein raw fiber is not loosened in the extension and contraction step.

The present invention also relates to a method for manufacturing fabric made of protein fibers, including a step of producing fabric using the protein fiber manufactured by the above-described method for manufacturing a protein fiber.

The present invention also relates to a method for processing a protein fiber, including: an extension and contraction step of contracting or extending a protein raw fiber containing a protein by bringing the protein raw fiber into contact with a liquid or vapor; and a drying step of drying the protein raw fiber that has undergone the extension and contraction step while adjusting a length of the protein raw fiber to an arbitrary length.

In the processing method of the present invention, the extension and contraction step may be a step of naturally contracting a length of the protein raw fiber by bringing the protein raw fiber into contact with the liquid or vapor.

The present invention also relates to a device for manufacturing a protein fiber, including: extension and contraction means for contracting or extending a protein raw fiber containing a protein by bringing the protein raw fiber into contact with a liquid or vapor that contracts or extends the protein raw fiber upon contact with the protein raw fiber; drying means for drying the protein raw fiber contracted or extended by the extension and contraction means; and adjustment means for adjusting a length of the protein raw fiber to an arbitrary length during drying of the protein raw fiber by the drying means.

In the manufacturing device of the present invention, the extension and contraction means may be configured to naturally contract the protein raw fiber by bringing the protein raw fiber into contact with the liquid or vapor.

The manufacturing device of the present invention may further include tensioning means for tensioning the protein raw fiber such that the contraction of the protein raw fiber by the extension and contraction means is performed in a state where the protein raw fiber is not loosened.

Effects of the Invention

According to the method for manufacturing a protein fiber of the present invention, it is possible to arbitrarily control an amount of change in length in a case where the protein raw fiber is brought into contact with moisture for the first time after manufacture merely by performing a simple step of drying after bringing the protein fiber into contact with a liquid or vapor. Therefore, it is possible to more easily manufacture a protein fiber in which an unexpected length change can be prevented. In addition, even with the device for manufacturing a protein fiber and the method for processing a protein fiber of the present invention, the effects substantially the same as those of the manufacturing method of the present invention can be exhibited. According to the method for manufacturing fabric made of protein fibers of the present invention, it is possible to more easily manufacture fabric made of protein fibers in which an unexpected length change when they are brought into contact with moisture for the first time after manufacture can be prevented.

BRIEF DESCRIPTION OF DRAWINGS

FIG. 5 is a schematic view showing another example of the manufacturing device for manufacturing a protein fiber. FIG. 5(a) shows a contraction processing device that is included in the manufacturing device, and FIG. 5(b) shows a drying device that is included in the manufacturing device.

EMBODIMENTS FOR CARRYING OUT THE INVENTION

Figure 1:
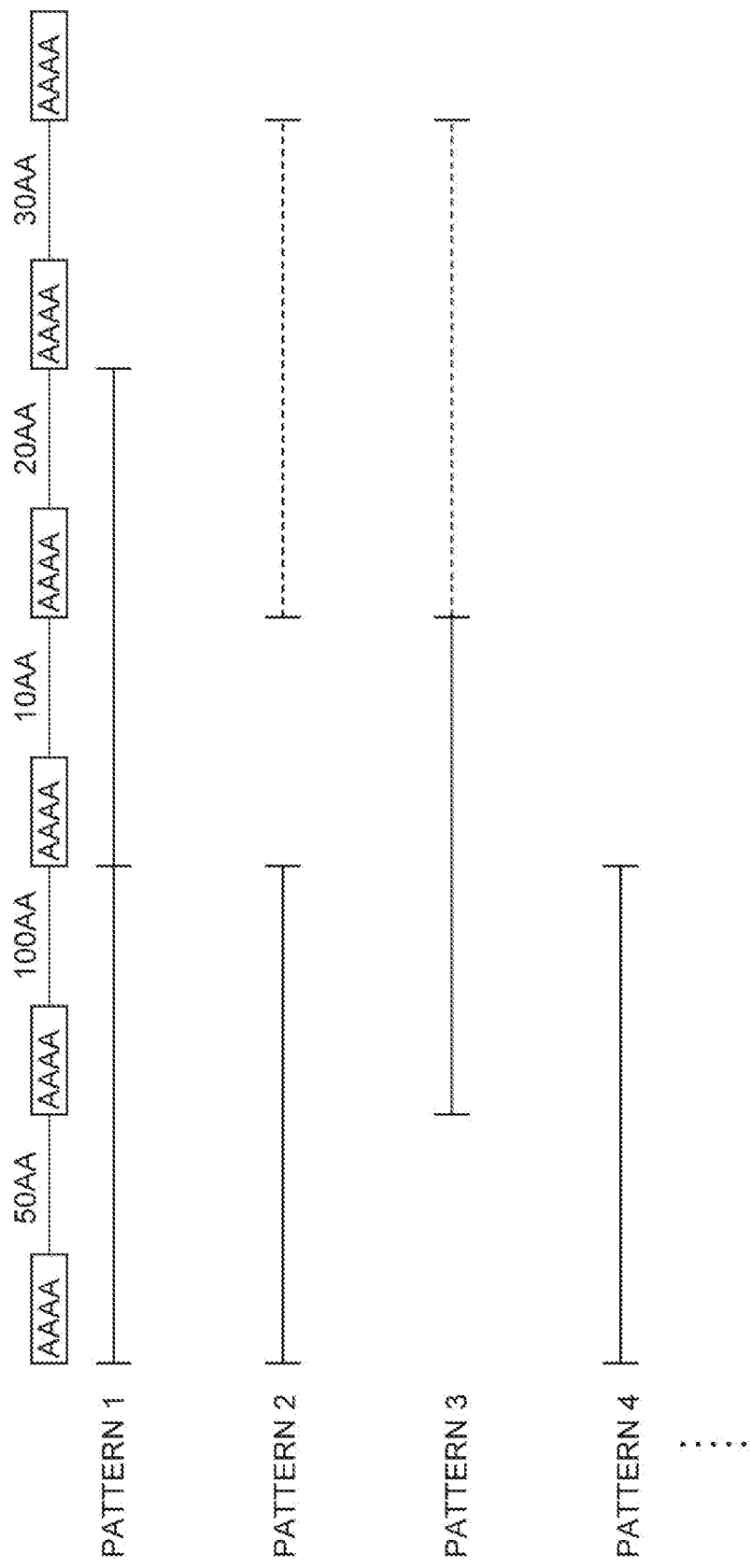
FIG. 1 is a schematic diagram showing an example of a domain sequence of a modified fibroin.

Hereinafter, although preferred embodiments of the present invention will be described in detail with reference to the drawings depending on the case, the present invention is not limited to the following embodiments. In the drawings, the same or corresponding portions are denoted by the same reference numerals, and overlapping descriptions will be appropriately omitted.

[Method for Manufacturing Protein Fiber]

A method for manufacturing a protein fiber of the present invention includes an extension and contraction step of contracting or extending a protein raw fiber containing a protein by bringing the protein raw fiber into contact with a liquid or vapor; and a drying step of drying the protein raw fiber that has undergone the extension and contraction step while adjusting a length of the protein raw fiber to an arbitrary length.

[Protein]

The protein fiber manufactured according to the manufacturing method of the present invention, or a protein raw fiber as a raw material, contains a protein, as a main component, which imparts a fiber which is naturally contracted or extended, and of which a length is naturally changed upon contact with a predetermined liquid such as water or vapor, for example, in a case where the liquid or vapor enters the inside of the fiber. The protein is not particularly limited, and may be a protein manufactured by a microorganism or the like by genetic recombination technology, or may be a protein manufactured synthetically, or may be a protein obtained by purifying naturally occurring proteins.

The protein may be, for example, a structural protein and an artificial structural protein derived from the structural protein. The structural protein means a protein which forms or retains the structure, form and the like in vivo. Examples of structural proteins include fibroin, keratin, collagen, elastin, resilin, and the like.

The structural protein may be a fibroin. The fibroin may be, for example, one or more kinds selected from the group consisting of a silk fibroin, a spider silk fibroin, and a hornet silk fibroin. In particular, the structural protein may be a silk fibroin, a spider silk fibroin or a combination thereof. In a case where a silk fibroin and a spider silk fibroin are used in combination, a proportion of silk fibroin may be, for example, 40 parts by mass or less, 30 parts by mass or less, or 10 parts by mass or less with respect to 100 parts by mass of a spider silk fibroin.

A silk thread is a fiber (cocoon yarn) obtained from cocoons made by silkworms which are larvae of silkworms (*Bombyx mori*). In general, one cocoon thread is composed of two silk fibroins and a shell material (sericin) covering them from the outside. The silk fibroin is composed of a large number of fibrils. The silk fibroin is covered with four layers of sericin. In practice, silk filaments obtained by dissolving and removing outer sericin by refining are used for clothing applications. A general silk thread has a specific gravity of 1.33, a fineness of 3.3 decitex on average, and a fiber length of about 1300 to 1500 m. The Silk fibroin can be obtained from natural or domestic silkworm cocoons, or used or discarded silk fabrics as a raw material.

As the silk fibroin, a sericin-removed silk fibroin, a sericin-unremoved silk fibroin, or a combination thereof may be used. The sericin-removed silk fibroin is obtained by removing and purifying sericin covering silk fibroin, other fats, and the like. The silk fibroin thus purified is preferably used as a freeze-dried powder. The sericin-unremoved silk fibroin is an unpurified silk fibroin from which sericin and the like are not removed.

The spider silk fibroin may contain a spider silk polypeptide selected from the group consisting of natural spider silk proteins and polypeptides derived from natural spider silk proteins (artificial spider silk proteins).

Examples of natural spider silk proteins include large nasogastric silkworm silk proteins, weft silk proteins, and viallet gland proteins. The large nasogastric silkworm silk has high stress and elasticity because it has a repeated region consisting of a crystalline region and a non-crystallin region (also referred to as an amorphous region). The weft of spider silk has a characteristic of having no crystalline region and having a repeated region consisting of a non-crystallin region. The weft is inferior in stress as compared with the large nasogastric silkworm silk, but has high elasticity.

The large nasogastric silkworm silk protein is characterized by having excellent toughness because of being manufactured in a large spider line. Examples of large nasogastric silkworm silk proteins include major ampullate spidroins MaSp1 and MaSp2 derived from *Nephila clavipes*, and ADF3 and ADF4 derived from *Araneus diadematus*. ADF3 is one of the two major dragline proteins of *Araneus diadematus*. The polypeptides derived from natural spider silk proteins may be polypeptides derived from these dragline proteins. The polypeptides derived from ADF3 are relatively easily synthesized, and have excellent properties in terms of strength-elongation and toughness.

A weft protein is manufactured in the flagelliform gland of the spider. Examples of weft proteins include a flagelliform silk protein derived from *Nephila clavipes*.

A polypeptide derived from a natural spider silk protein may be a recombinant spider silk protein. Examples of recombinant spider silk proteins include mutants, analogues, or derivatives of natural spider silk proteins. A preferred example of such a polypeptide is a recombinant spider silk protein (will be referred to as a "polypeptide derived from the large nasogastric dragline protein") of the large nasogastric silkworm protein.

Examples of fibroin-like proteins derived from the large nasogastric silkworm and proteins derived from *Bombyx mori* silk include proteins including domain sequences represented by Formula 1: $[(A)_n \text{ motif-REP}]_m$ or Formula 2: $[(A)_n \text{ motif-REP}]_m-(A)_n$ motif. The $(A)_n$ motif indicates an amino acid sequence mainly including an alanine residue, and the number of amino acid residues is 2 to 27. The number of amino acid residues of the $(A)_n$ motif may be an integer of 2 to 20, 4 to 27, 4 to 20, 8 to 20, 10 to 20, 4 to 16, 8 to 16, or 10 to 16. In addition, it is sufficient as long as a ratio of the number of alanine residues with respect to the total number of amino acid residues in the $(A)_n$ motif is 40% or more, and it may be 60% or more, 70% or more, 80% or more, 83% or more, 85% or more, 86% or more, 90% or more, 95% or more, or 100% (meaning it consists only of alanine residues). At least seven of a plurality of $(A)_n$ motifs present in the domain sequence consist of only alanine residues. REP represents an amino acid sequence consisting of 2 to 200 amino acid residues. REP may be an amino acid sequence consisting of 10 to 200 amino acid residues. m indicates an integer of 2 to 300, and may be an integer of 10 to 300. A plurality of $(A)_n$ motifs may be the same amino acid sequence or different amino acid sequences. A plurality of REPs may be the same amino acid sequence or different amino acid sequences.

A modified fibroin derived from the large nasogastric silkworm silk protein manufactured in the large ampullate gland of the spider includes a unit of the amino acid sequence represented by Formula 1: $[(A)_n \text{ motif-REP}]_m$, and may be a polypeptide which is an amino acid sequence having a homology of 90% or more to the amino acid sequence whose C-technical sequence is shown in any of SEQ ID NOs: 14 to 16, or the amino acid sequence set forth in any of SEQ ID NOs: 14 to 16.

The amino acid sequence set forth in SEQ ID NO: 14 is identical to the amino acid sequence consisting of 50 amino acid residues at the C-terminus of the amino acid sequence of ADF3 (GI: 1263287, NCBI); the amino acid sequence set forth in SEQ ID NO: 15 is identical to the amino acid sequence obtained by removing 20 residues from the C-terminus of the amino acid sequence set forth in SEQ ID NO: 14; and the amino acid sequence set forth in SEQ ID NO: 16 is identical to the amino acid sequence obtained by removing 29 residues from the C-terminus of the amino acid sequence set forth in SEQ ID NO: 14.

A more specific example of the modified fibroin derived from the large nasogastric silkworm silk protein manufactured in the large ampullate gland of the spider may be a modified fibroin including (1-i) an amino acid sequence set forth in SEQ ID NO: 17 or (1-ii) an amino acid sequence having 90% or more sequence identity with the amino acid sequence set forth in SEQ ID NO: 17. It is preferred that the sequence identity is 95% or more.

The amino acid sequence set forth in SEQ ID NO: 17 is an amino acid sequence in which the first to thirteenth repeat regions are increased to approximately double, and which is mutated so that the translation is terminated at the 1154th amino acid residue, in the amino acid sequence of ADF3 in which the amino acid sequence consisting of initiation codon, His10 tag, and HRV3C protease (Human rhinovirus 3C protease) recognition site (SEQ ID NO: 18) are added to the N terminus. The amino acid sequence at the C-terminus of the amino acid sequence set forth in SEQ ID NO: 17 is identical to the amino acid sequence set forth in SEQ ID NO: 16.

The modified fibroin of (1-i) may consist of the amino acid sequence set forth in SEQ ID NO: 17.

The modified fibroin in which a content of glycine residues is reduced has an amino acid sequence whose domain sequence has a reduced content of glycine residues as compared to naturally occurring fibroin. The modified fibroin can be said to have at least an amino acid sequence corresponding to substitution of one or a plurality of glycine residues in REP with another amino acid residue, as compared to naturally occurring fibroin.

The modified fibroin in which a content of glycine residues is reduced may be a modified fibroin in which the domain sequence has, in at least one motif sequence selected from GGX and GPGXX (where G represents a glycine residue, P represents a proline residue, and X represents an amino acid residue other than glycine) in REP, at least an amino acid sequence corresponding to substitution of one glycine residue in one or a plurality of the motif sequences with another amino acid residue, as compared to the naturally occurring fibroin.

The modified fibroin in which a content of glycine residues is reduced may be a modified fibroin in which the ratio of the motif sequence in which the glycine residue is substituted with another amino acid residue is 10% or more with respect to the entire motif sequence.

The modified fibroin in which a content of glycine residues is reduced may be a modified fibroin which includes a domain sequence represented by Formula 1: $[(A)_n$ motif-$REP]_m$, and has an amino acid sequence in which z/w is 30% or more, 40% or more, 50% or more, or 50.9% or more, in the case where the total number of amino acid residues in the amino acid sequence consisting of XGX (where G represents a glycine residue, and X represents an amino acid residue other than glycine) contained in all REPs in the sequence excluding the sequence from the $(A)_n$ motif located at the most C-terminal side to the C-terminus of the domain sequence from the domain sequence is defined as z, and the total number of amino acid residues in the sequence excluding the sequence from the $(A)_n$ motif located at the most C-terminal side to the C-terminus of the domain sequence from the domain sequence is defined as w. It is sufficient as long as the number of alanine residues is 83% or more relative to the total number of amino acid residues in the $(A)_n$ motif, but it is preferably 86% or more, more preferably 90% or more, still more preferably 95% or more, and even still more preferably 100% (which means that the $(A)_n$ motif consists of only alanine residues).

The modified fibroin in which a content of glycine residues is reduced is preferably a modified fibroin in which the content ratio of the amino acid sequence consisting of XGX is increased by substituting one glycine residue of the GGX motif with another amino acid residue. In the modified fibroin in which a content of glycine residues is reduced, the content ratio of the amino acid sequence consisting of GGX in the domain sequence is preferably 30% or less, more preferably 20% or less, still more preferably 10% or less, even still more preferably 6% or less, still further preferably 4% or less, and particularly preferably 2% or less. The content ratio of the amino acid sequence consisting of GGX in the domain sequence can be calculated by the same method as the calculation method of the content ratio (z/w) of the amino acid sequence consisting of XGX described below.

The calculation method of z/w will be described in more detail. First, in a fibroin (a modified fibroin or naturally occurring fibroin) containing a domain sequence represented by Formula 1: $[(A)_n$ motif-$REP]_m$, from the domain sequence, an amino acid sequence consisting of XGX is extracted from all the REPs contained in the sequence excluding the sequence from the $(A)_n$ motif located at the most C-terminal side to the C-terminus of the domain sequence. The total number of amino acid residues constituting XGX is z. For example, in the case where 50 amino acid sequences consisting of XGX are extracted (there is no overlap), z is 50×3=150. Also, for example, in the case where X (central X) contained in two XGXs exists as in the case of the amino acid sequence consisting of XGXGX, it is calculated by subtracting the overlapping portion (in the case of XGXGX, it is 5 amino acid residues). w is the total number of amino acid residues contained in the sequence excluding the sequence from the $(A)_n$ motif located at the most C-terminal side to the C-terminus of the domain sequence from the domain sequence. For example, in the case of the domain sequence shown in FIG. 1, w is 4+50+4+100+4+10+4+20+4+30=230 (excluding the $(A)_n$ motif located at the most C-terminal side). Next, z/w (%) can be calculated by dividing z by w.

In the modified fibroin in which a content of glycine residues is reduced, z/w is preferably 50.9% or more, more preferably 56.1% or more, still more preferably 58.7% or more, even still more preferably 70% or more, and still further preferably 80% or more. The upper limit of z/w is not particularly limited, but it may be 95% or less, for example.

The modified fibroin in which a content of glycine residues is reduced can be obtained, for example, by substituting and modifying at least a part of a base sequence encoding a glycine residue from the gene sequence of cloned naturally occurring fibroin so as to encode another amino acid residue. At this time, one glycine residue in the GGX motif and GPGXX motif may be selected as the glycine residue to be modified, and substitution may be carried out such that z/w is 50.9% or more. Alternatively, the modified fibroin according to the embodiment can also be obtained, for example, by designing an amino acid sequence satisfying each of the above embodiments from the amino acid sequence of naturally occurring fibroin and chemically synthesizing a nucleic acid encoding the designed amino acid sequence. In any case, in addition to the modification corresponding to substitution of a glycine residue in REP with another amino acid residue from the amino acid sequence of naturally occurring fibroin, modification of the amino acid sequence corresponding to substitution, deletion, insertion and/or addition of one or a plurality of amino acid residues may be carried out.

The above-mentioned another amino acid residue is not particularly limited as long as it is an amino acid residue other than a glycine residue, but it is preferably a hydrophobic amino acid residue such as a valine (V) residue, a leucine (L) residue, an isoleucine (I) residue, a methionine (M) residue, a proline (P) residue, a phenylalanine (F) residue, or a tryptophan (W) residue, or a hydrophilic amino acid residue such as a glutamine (Q) residue, an asparagine (N) residue, a serine (S) residue, a lysine (K) residue, or a glutamic acid (E) residue, among which more preferred is a valine (V) residue, a leucine (L) residue, an isoleucine (I) residue or a glutamine (Q) residue, and still more preferred is a glutamine (Q) residue.

A more specific example of the modified fibroin in which a content of glycine residues is reduced may be a modified fibroin including (2-i) an amino acid sequence set forth in SEQ ID NO: 3, SEQ ID NO: 4, SEQ ID NO: 10, or SEQ ID NO: 12; or (2-ii) an amino acid sequence having 90% or more sequence identity with the amino acid sequence set forth in SEQ ID NO: 3, SEQ ID NO: 4, SEQ ID NO: 10, or SEQ ID NO: 12.

The modified fibroin of (2-i) will be described. The amino acid sequence set forth in SEQ ID NO: 3 is obtained by substituting GQX for all GGX in REP of the amino acid sequence set forth in SEQ ID NO: 1 corresponding to naturally occurring fibroin. The amino acid sequence set forth in SEQ ID NO: 4 is obtained by deleting the $(A)_n$ motif every other two positions from the N-terminal side to the C-terminal side from the amino acid sequence set forth in SEQ ID NO: 3 and further inserting one $[(A)_n$ motif-REP] before the C-terminal sequence. The amino acid sequence set forth in SEQ ID NO: 10 is obtained by inserting two alanine residues at the C-terminal side of each $(A)_n$ motif of the amino acid sequence set forth in SEQ ID NO: 4 and further substituting a part of glutamine (Q) residues with a serine (S) residue to delete a part of amino acids on the N-terminal side so as to be almost the same as the molecular weight of SEQ ID NO: 4. The amino acid sequence set forth in SEQ ID NO: 12 is an amino acid sequence in which a His tag has been added to the C-terminus of a sequence obtained by repeating, 4 times, the region of the 20 domain sequences present in the amino acid sequence set forth in SEQ ID NO: 9 (however, several amino acid residues at the C-terminal side of the region are substituted).

The value of z/w in the amino acid sequence set forth in SEQ ID NO: 1 (corresponding to naturally occurring fibroin) is 46.8%. The values of z/w in the amino acid sequence set forth in SEQ ID NO: 3, the amino acid sequence set forth in SEQ ID NO: 4, the amino acid sequence set forth in SEQ ID NO: 10, and the amino acid sequence set forth in SEQ ID NO: 12 are respectively 58.7%, 70.1%, 66.1%, and 70.0%. In addition, the values of x/y at the Giza ratio (to be described later) 1:1.8 to 1:11.3 of the amino acid sequences set forth in SEQ ID NO: 1, SEQ ID NO: 3, SEQ ID NO: 4, SEQ ID NO: 10, and SEQ ID NO: 12 are respectively 15.0%, 15.0%, 93.4%, 92.7%, and 89.3%.

The modified fibroin of (2-i) may consist of an amino acid sequence set forth in SEQ ID NO: 3, SEQ ID NO: 4, SEQ ID NO: 10, or SEQ ID NO: 12.

The modified fibroin of (2-ii) includes an amino acid sequence having 90% or more sequence identity with the amino acid sequence set forth in SEQ ID NO: 3, SEQ ID NO: 4, SEQ ID NO: 10, or SEQ ID NO: 12. The modified fibroin of (2-ii) is also a protein including a domain sequence represented by Formula 1: $[(A)_n$ motif-REP]$_m$. The sequence identity is preferably 95% or more.

It is preferred that the modified fibroin of (2-ii) has 90% or more sequence identity with the amino acid sequence set forth in SEQ ID NO: 3, SEQ ID NO: 4, SEQ ID NO: 10, or SEQ ID NO: 12, and z/w is 50.9% or more in the case where the total number of amino acid residues in the amino acid sequence consisting of XGX (where G represents a glycine residue, and X represents an amino acid residue other than glycine) contained in REP is defined as z, and the total number of amino acid residues of REP in the domain sequence is defined as w.

The above-mentioned modified fibroin may include a tag sequence at either or both of the N-terminus and C-terminus. This makes it possible to isolate, immobilize, detect and visualize the modified fibroin.

The tag sequence may be, for example, an affinity tag utilizing specific affinity (binding property, affinity) with another molecule. As a specific example of the affinity tag, a histidine tag (His tag) can be mentioned. The His tag is a short peptide in which about 4 to 10 histidine residues are arranged and has a property of specifically binding to a metal ion such as nickel, so it can be used for isolation of modified fibroin by chelating metal chromatography. A specific example of the tag sequence may be an amino acid sequence set forth in SEQ ID NO: 5 (amino acid sequence including His tag).

In addition, a tag sequence such as glutathione-S-transferase (GST) that specifically binds to glutathione or a maltose binding protein (MBP) that specifically binds to maltose can also be used.

Further, an "epitope tag" utilizing an antigen-antibody reaction can also be used. By adding a peptide (epitope) showing antigenicity as a tag sequence, an antibody against the epitope can be bound. Examples of the epitope tag include an HA (peptide sequence of hemagglutinin of influenza virus) tag, a myc tag, and a FLAG tag. The modified fibroin can easily be purified with high specificity by utilizing an epitope tag.

It is also possible to use a tag sequence which can be cleaved with a specific protease. By treating a protein adsorbed through the tag sequence with protease, it is also possible to recover the modified fibroin cleaved from the tag sequence.

A more specific example of the modified fibroin including the tag sequence may be a modified fibroin including (2-iii) an amino acid sequence set forth in SEQ ID NO: 8, SEQ ID NO: 9, SEQ ID NO: 11, or SEQ ID NO: 13; or (2-iv) an amino acid sequence having 90% or more sequence identity with the amino acid sequence set forth in SEQ ID NO: 8, SEQ ID NO: 9, SEQ ID NO: 11, or SEQ ID NO: 13.

The amino acid sequences set forth in SEQ ID NO: 6, SEQ ID NO:7, SEQ ID NO: 8, SEQ ID NO: 9, SEQ ID NO: 11, and SEQ ID NO: 13 are amino acid sequences in which an amino acid sequence set forth in SEQ ID NO: 5 (including a His tag sequence and a hinge sequence) is added at the N-terminus of the amino acid sequences set forth in SEQ ID NO: 1, SEQ ID NO: 2, SEQ ID NO: 3, SEQ ID NO: 4, SEQ ID NO: 10, and SEQ ID NO: 12, respectively.

The modified fibroin of (2-iii) may consist of an amino acid sequence set forth in SEQ ID NO: 8, SEQ ID NO: 9, SEQ ID NO: 11, or SEQ ID NO: 13.

The modified fibroin of (2-iv) includes an amino acid sequence having 90% or more sequence identity with the amino acid sequence set forth in SEQ ID NO: 8, SEQ ID NO: 9, SEQ ID NO: 11, or SEQ ID NO: 13. The modified fibroin of (2-iv) is also a protein including a domain sequence represented by Formula 1: $[(A)_n$ motif-REP]$_m$. The sequence identity is preferably 95% or more.

It is preferred that the modified fibroin of (2-iv) has 90% or more sequence identity with the amino acid sequence set forth in SEQ ID NO: 8, SEQ ID NO: 9, SEQ ID NO: 11, or SEQ ID NO: 13, and z/w is 50.9% or more in the case where the total number of amino acid residues in the amino acid sequence consisting of XGX (where G represents a glycine residue, and X represents an amino acid residue other than glycine) contained in REP is defined as z, and the total number of amino acid residues of REP in the domain sequence is defined as w.

The above-mentioned modified fibroin may include a secretory signal for releasing the protein manufactured in the recombinant protein manufacture system to the outside of a host. The sequence of the secretory signal can be appropriately set depending on the type of the host.

The modified fibroin in which a content of $(A)_n$ motifs is reduced has an amino acid sequence whose domain sequence has a reduced content of $(A)_n$ motifs as compared to naturally occurring fibroin. The domain sequence of the modified fibroin can be said to have at least an amino acid sequence corresponding to deletion of one or a plurality of $(A)_n$ motifs, as compared to naturally occurring fibroin.

The modified fibroin in which a content of $(A)_n$ motifs is reduced may have an amino acid sequence corresponding to 10 to 40% deletion of the $(A)_n$ motif from naturally occurring fibroin.

The modified fibroin in which a content of $(A)_n$ motifs is reduced may be a modified fibroin whose domain sequence has at least an amino acid sequence corresponding to deletion of one $(A)_n$ motif per one to three $(A)_n$ motifs from the N-terminal side to the C-terminal side, as compared to naturally occurring fibroin.

The modified fibroin in which a content of $(A)_n$ motifs is reduced may be a modified fibroin whose domain sequence has at least an amino acid sequence corresponding to repetition of two consecutive $(A)_n$ motif deletions and one $(A)_n$ motif deletion in this order from the N-terminal side to the C-terminal side, as compared to the naturally occurring fibroin.

The modified fibroin in which a content of $(A)_n$ motifs is reduced may be a modified fibroin whose domain sequence has at least an amino acid sequence corresponding to deletion of the $(A)_n$ motif every other two positions from the N-terminal side to the C-terminal side.

The modified fibroin in which a content of (A motifs is reduced may be a modified fibroin which have a domain sequence represented by Formula 1: $[(A)_n$ motif-REP$]_m$, and have an amino acid sequence in which x/y is 20% or more, 30% or more, 40% or more, or 50% or more, in the case where the number of amino acid residues in REPs of two adjacent $[(A)_n$ motif-REP] units is sequentially compared from the N-terminal side to the C-terminal side, and the number of amino acid residues in REP having a smaller number of amino acid residues is defined as 1, the maximum value of the total value of the number of amino acid residues in the two adjacent $[(A)_n$ motif-REP] units where the ratio of the number of amino acid residues in the other REP is 1.8 to 11.3 is defined as x, and the total number of amino acid residues of the domain sequence is y. It is sufficient as long as the number of alanine residues is 83% or more relative to the total number of amino acid residues in the $(A)_n$ motif, but it is preferably 86% or more, more preferably 90% or more, still more preferably 95% or more, and even still more preferably 100% (which means that the $(A)_n$ motif consists of only alanine residues).

A method of calculating x/y will be described in more detail with reference to FIG. 1. FIG. 1 shows a domain sequence excluding N-terminal sequence and C-terminal sequence from modified fibroin. This domain sequence has a sequence of $(A)_n$ motif-first REP (50 amino acid residues)-$(A)_n$ motif-second REP (100 amino acid residues)-$(A)_n$ motif-third REP (10 amino acid residues)-$(A)_n$ motif-fourth REP (20 amino acid residues)-$(A)_n$ motif-fifth REP (30 amino acid residues)-$(A)_n$ motif from the N-terminal side (left side).

The two adjacent $[(A)_n$ motif-REP] units are sequentially selected from the N-terminal side to the C-terminal side so as not to overlap. At this time, an unselected $[(A)_n$ motif-REP] unit may exist. FIG. 1 shows a pattern 1 (a comparison between first REP and second REP and a comparison between third REP and fourth REP), a pattern 2 (a comparison between first REP and second REP and a comparison between fourth REP and fifth REP), a pattern 3 (a comparison between second REP and third REP and a comparison between fourth REP and fifth REP), and a pattern 4 (a comparison between first REP and second REP). There are other selection methods besides this.

Next, for each pattern, the number of amino acid residues of each REP in the selected two adjacent $[(A)_n$ motif-REP] units is compared. The comparison is carried out by obtaining the ratio of the number of amino acid residues of the other REP in the case where one REP having a smaller number of amino acid residues is 1. For example, in the case of comparing the first REP (50 amino acid residues) and the second REP (100 amino acid residues), the ratio of the number of amino acid residues of the second REP is 100/50=2 in the case where the first REP having a smaller number of amino acid residues is 1. Similarly, in the case of comparing the fourth REP (20 amino acid residues) and the fifth REP (30 amino acid residues), the ratio of the number of amino acid residues of the fifth REP is 30/20=1.5 in the case where the fourth REP having a smaller number of amino acid residues is 1.

In FIG. 1, a set of $[(A)_n$ motif-REP] units in which the ratio of the number of amino acid residues of the other REP is 1.8 to 11.3 in the case where one REP having a smaller number of amino acid residues is 1 is indicated by a solid line. Hereinafter, such a ratio is referred to as a Giza ratio. A set of $[(A)_n$ motif-REP] units in which the ratio of the number of amino acid residues of the other REP is less than 1.8 or more than 11.3 in the case where one REP having a smaller number of amino acid residues is 1 is indicated by a broken line.

In each pattern, the number of all amino acid residues of two adjacent $[(A)_n$ motif-REP] units indicated by solid lines (including not only the number of amino acid residues of REP but also the number of amino acid residues of $(A)_n$ motif) is combined. Then, the total values thus combined are compared and the total value of the pattern whose total value is the maximum (the maximum value of the total value) is defined as x. In the example shown in FIG. 1, the total value of the pattern 1 is the maximum.

Next, x/y (%) can be calculated by dividing x by the total amino acid residue number y of the domain sequence.

In the modified fibroin in which a content of $(A)_n$ motifs is reduced, x/y is preferably 50% or more, more preferably 60% or more, still more preferably 65% or more, even still more preferably 70% or more, still further preferably 75% or more, and particularly preferably 80% or more. The upper limit of x/y is not particularly limited, and it may be 100% or less, for example. In a case where a Giza ratio is 1:1.9 to 1:11.3, x/y is preferably 89.6% or more; in a case where a Giza ratio is 1:1.8 to 1:3.4, x/y is preferably 77.1% or more; in a case where a Giza ratio is 1:1.9 to 1:8.4, x/y is preferably 75.9% or more; and in a case where a Giza ratio is 1:1.9 to 1:4.1, x/y is preferably 64.2% or more.

In a case where the modified fibroin in which a content of $(A)_n$ motifs is reduced is a modified fibroin in which at least seven of (A)n motifs which are present in plural in the domain sequence are composed of only alanine residues, x/y is preferably 46.4% or more, is more preferably 50% or more, is even more preferably 55% or more, is still even more preferably 60% or more, is still even more preferably 70% or more, and is particularly preferable 80% or more. The upper limit of x/y is not particularly limited, and may be 100% or less.

The modified fibroin in which a content of $(A)_n$ motifs is reduced can be obtained, for example, from a gene sequence of cloned naturally occurring fibroin, by deleting one or a plurality of the sequences encoding the $(A)_n$ motif such that x/y is 64.2% or more. Further, the modified fibroin including a domain sequence with a reduced $(A)_n$ motif content can also be obtained, for example, by designing an amino acid sequence corresponding to deletion of one or a plurality of $(A)_n$ motifs such that x/y is 64.2% or more, from the amino acid sequence of naturally occurring fibroin, and chemically synthesizing a nucleic acid encoding the designed amino acid sequence. In any case, in addition to the modification corresponding to deletion of $(A)_n$ motif from the amino acid sequence of naturally occurring fibroin, modification of the amino acid sequence corresponding to substitution, deletion, insertion and/or addition of one or a plurality of amino acid residues may be carried out.

A more specific example of the modified fibroin in which a content of $(A)_n$ motifs is reduced may be a modified fibroin including (3-i) an amino acid sequence set forth in SEQ ID NO: 2, SEQ ID NO: 4, SEQ ID NO: 10, or SEQ ID NO: 12; or (3-ii) an amino acid sequence having 90% or more sequence identity with the amino acid sequence set forth in SEQ ID NO: 2, SEQ ID NO: 4, SEQ ID NO: 10, or SEQ ID NO: 12.

The modified fibroin of (3-i) will be described. The amino acid sequence set forth in SEQ ID NO: 2 is obtained by deleting the $(A)_n$ motif every other two positions from the N-terminal side to the C-terminal side from the amino acid sequence set forth in SEQ ID NO: 1 corresponding to naturally occurring fibroin and further inserting one [$(A)_n$ motif-REP] before the C-terminal sequence. The amino acid sequence set forth in SEQ ID NO: 4 is obtained by substituting GQX for all GGX in REP of the amino acid sequence set forth in SEQ ID NO: 2. The amino acid sequence set forth in SEQ ID NO: 10 is obtained by inserting two alanine residues at the C-terminal side of each $(A)_n$ motif of the amino acid sequence set forth in SEQ ID NO: 4 and further substituting a part of glutamine (Q) residues with a serine (S) residue to delete a part of amino acids on the N-terminal side so as to be almost the same as the molecular weight of SEQ ID NO: 4. The amino acid sequence set forth in SEQ ID NO: 12 is an amino acid sequence in which a His tag has been added to the C-terminus of a sequence obtained by repeating, 4 times, the region of the 20 domain sequences present in the amino acid sequence set forth in SEQ ID NO: 9 (however, several amino acid residues at the C-terminal side of the region are substituted).

The value of x/y in the Giza ratio 1:1.8 to 1:11.3 of the amino acid sequence set forth in SEQ ID NO: 1 (corresponding to naturally occurring fibroin) is 15.0%. Values of x/y in the amino acid sequence set forth in SEQ ID NO: 2 and the amino acid sequence set forth in SEQ ID NO: 4 are both 93.4%. The value of x/y in the amino acid sequence set forth in SEQ ID NO: 10 is 92.7%. The value of x/y in the amino acid sequence set forth in SEQ ID NO: 12 is 89.3%. The values of z/w at the amino acid sequences set forth in SEQ ID NO: 1, SEQ ID NO: 2, SEQ ID NO: 4, SEQ ID NO: 10, and SEQ ID NO: 12 are respectively 46.8%, 56.2%, 70.1%, 66.1%, and 70.0%.

The modified fibroin of (3-i) may consist of an amino acid sequence set forth in SEQ ID NO: 2, SEQ ID NO: 4, SEQ ID NO: 10, or SEQ ID NO: 12.

The modified fibroin of (3-ii) includes an amino acid sequence having 90% or more sequence identity with the amino acid sequence set forth in SEQ ID NO: 2, SEQ ID NO: 4, SEQ ID NO: 10, or SEQ ID NO: 12. The modified fibroin of (3-ii) is also a protein including a domain sequence represented by Formula 1: [$(A)_n$ motif-REP] m. The sequence identity is preferably 95% or more.

The modified fibroin of (3-ii) preferably has 90% or more sequence identity with the amino acid sequence set forth in SEQ ID NO: 2, SEQ ID NO: 4, SEQ ID NO: 10, or SEQ ID NO: 12, and has an amino acid sequence in which x/y is 64.2% or more, in the case where the number of amino acid residues in REPs of two adjacent [$(A)_n$ motif-REP] units is sequentially compared from the N-terminal side to the C-terminal side, and the number of amino acid residues in REP having a smaller number of amino acid residues is defined as 1, the maximum value of the total value of the number of amino acid residues in the two adjacent [$(A)_n$ motif-REP] units where the ratio of the number of amino acid residues in the other REP is 1.8 to 11.3 (a Giza ratio of 1:1.8 to 1:11.3) is defined as x, and the total number of amino acid residues of the domain sequence is y.

The above-mentioned modified fibroin may include the above-mentioned tag sequence at either or both of the N-terminus and C-terminus.

A more specific example of the modified fibroin including the tag sequence may be a modified fibroin including (3-iii) an amino acid sequence set forth in SEQ ID NO: 7, SEQ ID NO: 9, SEQ ID NO: 11, or SEQ ID NO: 13; or (2-iv) an amino acid sequence having 90% or more sequence identity with the amino acid sequence set forth in SEQ ID NO: 7, SEQ ID NO: 9, SEQ ID NO: 11, or SEQ ID NO: 13.

The amino acid sequences set forth in SEQ ID NO: 6, SEQ ID NO:7, SEQ ID NO: 8, SEQ ID NO: 9, SEQ ID NO: 11, and SEQ ID NO: 13 are amino acid sequences in which an amino acid sequence set forth in SEQ ID NO: 5 (including a His tag sequence) is added at the N-terminus of the amino acid sequences set forth in SEQ ID NO: 1, SEQ ID NO: 2, SEQ ID NO: 3, SEQ ID NO: 4, SEQ ID NO: 10, and SEQ ID NO: 12, respectively.

The modified fibroin of (3-iii) may consist of an amino acid sequence set forth in SEQ ID NO: 7, SEQ ID NO: 9, SEQ ID NO: 11, or SEQ ID NO: 13.

The modified fibroin of (3-iv) includes an amino acid sequence having 90% or more sequence identity with the amino acid sequence set forth in SEQ ID NO: 7, SEQ ID NO: 9, SEQ ID NO: 11, or SEQ ID NO: 13. The modified fibroin of (3-iv) is also a protein including a domain sequence represented by Formula 1: [$(A)_n$ motif-REP]$_m$. The sequence identity is preferably 95% or more.

The modified fibroin of (3-iv) preferably has 90% or more sequence identity with the amino acid sequence set forth in SEQ ID NO: 7, SEQ ID NO: 9, SEQ ID NO: 11, or SEQ ID NO: 13, and has an amino acid sequence in which x/y is 64.2% or more, in the case where the number of amino acid residues in REPs of two adjacent [$(A)_n$ motif-REP] units is sequentially compared from the N-terminal side to the C-terminal side, and the number of amino acid residues in REP having a smaller number of amino acid residues is defined as 1, the maximum value of the total value of the number of amino acid residues in the two adjacent [$(A)_n$ motif-REP] units where the ratio of the number of amino acid residues in the other REP is 1.8 to 11.3 is defined as x, and the total number of amino acid residues of the domain sequence is y.

The above-mentioned modified fibroin may include a secretory signal for releasing the protein manufactured in the recombinant protein manufacture system to the outside of a host. The sequence of the secretory signal can be appropriately set depending on the type of the host.

The modified fibroin in which a content of glycine residues and a content of $(A)_n$ motifs are reduced is a modified fibroin in which the domain sequence has an amino acid sequence in which the content of glycine residues is reduced in addition to having a reduced content of $(A)_n$ motifs as compared to naturally occurring fibroin. The domain sequence of the modified fibroin can be said to further have an amino acid sequence corresponding at least the substitution of one or a plurality of glycine residues in REP with another amino acid residue, in addition to deletion of one or a plurality of $(A)_n$ motifs, as compared to naturally occurring fibroin. In other words, it is a modified fibroin having characteristics of the modified fibroin in which a content of glycine residues is reduced, and the modified fibroin in which a content of $(A)_n$ motifs is reduced in combination. Specific aspects thereof are as described in the modified fibroin in which a content of glycine residues is reduced, and the modified fibroin in which a content of $(A)_n$ motifs is reduced.

A more specific example of the modified fibroin in which a content of glycine residues and a content of $(A)_n$ motifs are reduced may be a modified fibroin including (4-i) an amino acid sequence set forth in SEQ ID NO: 4, SEQ ID NO: 10, or SEQ ID NO: 12; or (4-ii) an amino acid sequence having 90% or more sequence identity with the amino acid sequence set forth in SEQ ID NO: 4, SEQ ID NO: 10, or SEQ ID NO: 12. Specific aspects of the modified fibroin including the amino acid sequence set forth in SEQ ID NO: 4, SEQ ID NO: 10, or SEQ ID NO: 12 are as described above.

The modified fibroin according to another embodiment may be a modified fibroin having an amino acid sequence having a region locally having a large hydrophobicity index, in which the domain sequence thereof corresponds to a sequence in which one or a plurality of amino acid residues in the REP is substituted by an amino acid residue having a large hydrophobicity index, and/or one or a plurality of amino acid residues having a large hydrophobicity index is inserted into the REP, as compared to naturally occurring fibroins.

The region locally having a large hydrophobicity index is preferably composed of 2 to 4 consecutive amino acid residues.

The amino acid residue having a large hydrophobicity index mentioned above is more preferably an amino acid residue selected from isoleucine (I), valine (V), leucine (L), phenylalanine (F), cysteine (C), methionine (M), and alanine (A).

In the modified fibroin according to the present embodiment may be a modified fibroin, in addition to modification corresponding to substitution of one or a plurality of amino acid residues in the REP by an amino acid residue having a large hydrophobicity index, and/or insertion of one or a plurality of amino acid residues having a large hydrophobicity index into the REP, as compared to naturally occurring fibroins, there may a modification of the amino acid sequence corresponding to substitution, deletion, insertion, and/or addition of one or a plurality of amino acid residues, as compared to naturally occurring fibroins.

The modified fibroin according to the present embodiment can be obtained by, from the gene sequence of cloned naturally occurring fibroins, substituting one or a plurality of hydrophilic amino acid residues in the REP (for example, amino acid residues whose hydrophobicity index is negative) by hydrophobic amino acid residues (for example, amino acid residues whose hydrophobicity index is positive); and/or by inserting one or a plurality of hydrophobic amino acid residues into REP. In addition, the modified fibroin according to the present embodiment can be obtained by, for example, designing an amino acid sequence corresponding to substitution of one or a plurality of hydrophilic amino acid residues in the REP by hydrophobic amino acid residues, from the amino acid sequence of naturally occurring fibroins, and/or insertion of one or a plurality of hydrophobic amino acid residues into the REP; and chemically synthesizing a nucleic acid encoding the designed amino acid sequence. In any case, in addition to modification corresponding to substitution of one or a plurality of hydrophilic amino acid residues in the REP by hydrophobic amino acid residues, from the amino acid sequence of naturally occurring fibroins, and/or insertion of one or a plurality of hydrophobic amino acid residues into the REP, further modification of the amino acid sequence corresponding to substitution, deletion, insertion and/or addition of one or a plurality of amino acid residues may be carried out.

The modified fibroin according to still another embodiment contains the domain sequence represented by Formula 1: $[(A)_n$ motif-REP$]_m$, and may have an amino acid sequence whose p/q is 6.2% or more, in all of the REP included in the sequence obtained by removing the sequence from the $(A)_n$ motif located the most C-terminal side to the C-terminus of the domain sequence, from the above-mentioned domain sequence, in a case where the total number of amino acid residues contained in a region where the average value of the hydrophobicity index of four consecutive amino acid residues is 2.6 or more is p, and the total number of amino acid residues contained in the sequence obtained by removing the sequence from the $(A)_n$ motif located the most C-terminal side to the C-terminus of the domain sequence, from the above-mentioned domain sequence is q.

With regard to the hydrophobicity index of amino acid residues, known indices (Hydropathy index: Kyte J, & Doolittle R (1982) "A simple method for displaying the hydropathic character of a protein," J. Mol. Biol., 157, pp. 105-132) are used. Specifically, the hydrophobicity index (hydropatshy index, hereinafter will be referred to as "HI") of each amino acid is as shown in Table 1.

TABLE 1

| Amino acid | HI | Amino acid | HI |
| --- | --- | --- | --- |
| Isoleucine (Ile) | 4.5 | Tryptophan (Trp) | −0.9 |
| Valine (Val) | 4.2 | Tyrosine (Tyr) | −1.3 |
| Leucine (Leu) | 3.8 | Proline (Pro) | −1.6 |
| Phenylalanine (Phe) | 2.8 | Histidine (His) | −3.2 |
| Cysteine (Cys) | 2.5 | Asparagine (Asn) | −3.5 |
| Methionine (Met) | 1.9 | Asparaginic acid (Asp) | −3.5 |
| Alanine (Ala) | 1.8 | Glutamine (Gln) | −3.5 |
| Glycine (Gly) | −0.4 | Glutamic acid (Glu) | −3.5 |
| Threonine (Thr) | −0.7 | Lysine (Lys) | −3.9 |
| Serine (Ser) | −0.8 | Arginine (Arg) | −4.5 |

The calculation method of p/q will be described in more detail. In the calculation, the sequence obtained by removing the sequence from the $(A)_n$ motif located at the most C-terminal side to the C-terminus of the domain sequence, from the domain sequence represented by Formula 1: $[(A)_n$ motif-REP]$_m$, is used. First, in all REPs included in sequence A, an average value of the hydrophobicity index of four consecutive amino acid residues is calculated. The average value of the hydrophobicity index is obtained by dividing the sum of HI of each amino acid residue contained in the four consecutive amino acid residues by 4 (the number of amino acid residues). The average value of the hydrophobicity index is obtained for all four consecutive amino acid residues (each amino acid residue is used to calculate an average of 1 to 4 times). Next, a region in which the average value of the hydrophobicity index of the four consecutive amino acid residues is 2.6 or more is identified. Even in a case where a certain amino acid residue corresponds to the "four consecutive amino acid residues in which the average value of the plurality of hydrophobicity indices is 2.6 or more," this amino acid residue is included in the region as one amino acid residue. In addition, a total number of amino acid residues contained in the region is p. Furthermore, the total number of amino acid residues contained in the sequence A is q.

Figure 2:
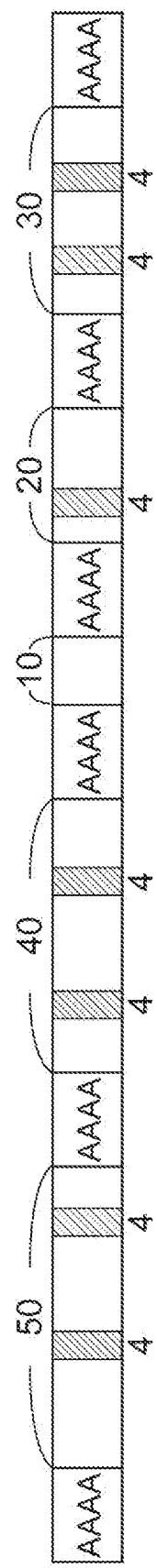
FIG. 2 is a schematic diagram showing an example of a domain sequence of a modified fibroin.

For example, in a case where consecutive four amino acid residues having the average value of the hydrophobicity index of 2.6 or more are extracted at 20 positions (no duplication), in the region where the average value of the hydrophobicity index of the four consecutive amino acid residues is 2.6 or more, there are 20 consecutive four amino acid residues (no duplication), and therefore p is 20×4=80. In addition, for example, in a case where two "consecutive four amino acid residues having an average value of the hydrophobicity index of 2.6 or more" overlap by one amino acid residue, in the region where the average value of the hydrophobicity index of the four consecutive amino acid residues is 2.6 or more, seven amino acid residues are contained (p=2×4−1=7, where "−1" is a subtraction of duplicates). For example, in the case of the domain sequence shown in FIG. 2, p is 7×4=28, because seven "consecutive four amino acid residues having the average value of the hydrophobicity index of 2.6 or more" are present without duplication. In addition, for example, in the case of the domain sequence shown in FIG. 2, q is 4+50+4+40+4+10+4+20+4+30=170 (not including the (A)$_n$ motif present at the C-terminus). Next, p/q (%) can be calculated by dividing p by q. In the case of FIG. 2, 28/170=16.47%.

In the modified fibroin according to the present embodiment, p/q is preferably 6.2% or more, more preferably 7% or more, still more preferably 10% or more, even still more preferably 20% or more, and still further preferably 30% or more. The upper limit of p/q is not particularly limited, but it may be 45% or less, for example.

The modified fibroin according to the present embodiment can be obtained by modifying the amino acid sequence of cloned naturally occurring fibroins to the amino acid sequence containing the region locally having a large hydrophobicity index, by substituting one or a plurality of hydrophilic amino acid residues in the REP (for example, amino acid residues whose hydrophobicity index is negative) by hydrophobic amino acid residues (for example, amino acid residues whose hydrophobicity index is positive); and/or by inserting one or a plurality of hydrophobic amino acid residues into REP, such that the above conditions of p/q is satisfied. Alternatively, the modified fibroin according to the embodiment can also be obtained, for example, by designing an amino acid sequence satisfying the conditions of p/q from the amino acid sequence of naturally occurring fibroin and chemically synthesizing a nucleic acid encoding the designed amino acid sequence. In any case, in addition to modification corresponding to substitution of one or a plurality of amino acid residues in the REP by amino acid residues having a large hydrophobicity index, and/or insertion of one or a plurality of amino acid residues having a large hydrophobicity index into the REP as compared to naturally occurring fibroins, further modification corresponding to substitution, deletion, insertion and/or addition of one or a plurality of amino acid residues may be carried out.

The amino acid residue having a large hydrophobicity index mentioned above is not particularly limited, but is preferably isoleucine (I), valine (V), leucine (L), phenylalanine (F), cysteine (C), methionine (M), and alanine (A), and is more preferably valine (V), leucine (L), and isoleucine (I).

Other specific examples of the modified fibroin include modified fibroins including (5-i) an amino acid sequence set forth in SEQ ID NO: 19, SEQ ID NO: 21, or SEQ ID NO: 22, or (5-ii) an amino acid sequence having 90% or more sequence identity with the amino acid sequence set forth in SEQ ID NO: 19, SEQ ID NO: 21, or SEQ ID NO: 22.

The modified fibroin of (5-i) will be described. The amino acid sequence set forth in SEQ ID NO: 4 is an amino acid sequence in which consecutive amino acid sequences are deleted such that the number of consecutive alanine residues in the (A)$_n$ motif of naturally occurring fibroins becomes 5. The amino acid sequence set forth in SEQ ID NO: 19 is an amino acid sequence in which, with respect to the amino acid sequence set forth in SEQ ID NO: 4, an amino acid sequence (VLI) consisting of three amino acid residues is inserted in two places every REP, respectively, and some of amino acids at the C-terminal side is deleted so that a molecular weight thereof becomes almost the same molecular weight as the amino acid sequence set forth in SEQ ID NO: 4. The amino acid sequence set forth in SEQ ID NO: 20 is obtained by inserting two alanine residues at the C-terminal side of each (A)$_n$ motif with respect to the amino acid sequence set forth in SEQ ID NO: 19, and further substituting a part of glutamine (Q) residues with a serine (S) residue to delete a part of amino acids on the C-terminal side so as to be almost the same as the molecular weight of the amino acid sequence set forth in SEQ ID NO: 4. The amino acid sequence set forth in SEQ ID NO: 21 is an amino acid sequence in which, with respect to the amino acid sequence set forth in SEQ ID NO: 20, an amino acid sequence (VIT) consisting of three amino acid residues is inserted in one place every REP, respectively. The amino acid sequence set forth in SEQ ID NO: 22 is an amino acid sequence in which, with respect to the amino acid sequence set forth in SEQ ID NO: 20, an amino acid sequence (VLI) consisting of three amino acid residues is inserted in two places every REP, respectively.

The modified fibroin of (5-i) may consist of the amino acid sequence set forth in SEQ ID NO: 19, SEQ ID NO: 21, or SEQ ID NO: 22.

The modified fibroin of (5-ii) includes an amino acid sequence having 90% or more sequence identity with the amino acid sequence set forth in SEQ ID NO: 19, SEQ ID NO: 21, or SEQ ID NO: 22. The modified fibroin of (5-ii) is also a protein including a domain sequence represented by Formula 1: [(A)$_n$ motif-REP] m. The sequence identity is preferably 95% or more.

The modified fibroin of (5-ii) has 90% or more sequence identity with the amino acid sequence set forth in SEQ ID NO: 19, SEQ ID NO: 21, or SEQ ID NO: 22, and preferably has p/q of 6.2% or more, in all of the REP included in the sequence obtained by removing the sequence from the (A)$_n$ motif located the most C-terminal side to the C-terminus of the domain sequence, from the above-mentioned domain sequence, in a case where the total number of amino acid residues contained in a region where the average value of the hydrophobicity index of four consecutive amino acid residues is 2.6 or more is p, and the total number of amino acid residues contained in the sequence obtained by removing the sequence from the $(A)_n$ motif located the most C-terminal side to the C-terminus of the domain sequence, from the above-mentioned domain sequence is q.

The above-mentioned modified fibroin may include a tag sequence at either or both of the N-terminus and C-terminus.

A more specific example of the modified fibroin including a tag sequence may be a modified fibroin including (5-iii) an amino acid sequence set forth in SEQ ID NO: 23, SEQ ID NO: 24, or SEQ ID NO: 25, or (5-iv) an amino acid sequence having 90% or more sequence identity with the amino acid sequence set forth in SEQ ID NO: 23, SEQ ID NO: 24, or SEQ ID NO: 25.

The amino acid sequences set forth in SEQ ID NO: 23, SEQ ID NO:24, and SEQ ID NO: 25 are amino acid sequences in which an amino acid sequence set forth in SEQ ID NO: 5 (including a His tag sequence and a hinge sequence) is added at the N-terminus of the amino acid sequences set forth in SEQ ID NO: 19, SEQ ID NO: 21, and SEQ ID NO: 22, respectively.

The modified fibroin of (5-iii) may consist of an amino acid sequence set forth in SEQ ID NO: 23, SEQ ID NO: 24, or SEQ ID NO: 25.

The modified fibroin of (5-iv) includes an amino acid sequence having 90% or more sequence identity with the amino acid sequence set forth in SEQ ID NO: 23, SEQ ID NO: 24, or SEQ ID NO: 25. The modified fibroin of (5-iv) is also a protein including a domain sequence represented by Formula 1: $[(A)_n \text{ motif-REP}]_m$. The sequence identity is preferably 95% or more.

The modified fibroin of (5-iv) has 90% or more sequence identity with the amino acid sequence set forth in SEQ ID NO: 23, SEQ ID NO: 24, or SEQ ID NO: 25, and preferably has p/q of 6.2% or more, in all of the REP included in the sequence obtained by removing the sequence from the $(A)_n$ motif located the most C-terminal side to the C-terminus of the domain sequence, from the above-mentioned domain sequence, in a case where the total number of amino acid residues contained in a region where the average value of the hydrophobicity index of four consecutive amino acid residues is 2.6 or more is p, and the total number of amino acid residues contained in the sequence obtained by removing the sequence from the $(A)_n$ motif located the most C-terminal side to the C-terminus of the domain sequence, from the above-mentioned domain sequence is q.

The above-mentioned modified fibroin may include a secretory signal for releasing the protein manufactured in the recombinant protein manufacture system to the outside of a host. The sequence of the secretory signal can be appropriately set depending on the type of the host.

Examples of proteins derived from the weft protein include a protein including a domain sequence represented by Formula 3: $[REP2]_o$ (where, in Formula 3, REP2 represents an amino acid sequence composed of Gly-Pro-Gly-Gly-X, X represents one amino acid selected from the group consisting of alanine (Ala), serine (Ser), tyrosine (Tyr), and valine (Val), and o represents an integer of 8 to 300). Specific examples thereof include a protein including the amino acid sequence set forth in SEQ ID NO: 26. The amino acid sequence set forth in SEQ ID NO: 26 is an amino acid sequence in which the amino acid sequence (referred to as a PR1 sequence) from 1220th residue to 1659th residue from the N-terminus corresponding to a motif and a repeat part of a partial sequence (NCBI Accession No.: AAF36090, GI: 7106224) of the flagelliform silk protein of *Nephila clavipes* obtained from the NCBI database is bonded to the C-terminal amino acid sequence from the 816th residue to 907th residue from the C-terminus of a partial sequence (NCBI Accession No.: AAC38847, GI: 2833649) of the flagelliform silk protein of *Nephila clavipes* obtained from the NCBI database; and the amino acid sequence (a tag sequence and a hinge sequence) set forth in SEQ ID NO: 5 is added to the N-terminus of the bonded sequence.

Examples of proteins derived from collagen include a protein including a domain sequence represented by Formula 4: $[REP3]_p$ (where, in Formula 4, p represents an integer of 5 to 300, REP3 represents the amino acid sequence consisting of Gly-X-Y, X and Y represent any amino acid residues other than Gly, and a plurality of REP3's may be the same amino acid sequence with each other or different amino acid sequences from each other). Specific examples thereof include a protein including the amino acid sequence set forth in SEQ ID NO: 27. The amino acid sequence set forth in SEQ ID NO: 27 is an amino acid sequence in which the amino acid sequence (a tag sequence and a hinge sequence) set forth in SEQ ID NO: 5 is added to the N-terminus of the amino acid sequence from 301st residue to 540th residue corresponding to the motif and a repeat part of a partial sequence of human collagen type 4 obtained from the NCBI database (Accession No: CAA56335.1, GI: 3702452 of NCBI GenBank).

Examples of proteins derived from resilin include a protein including a domain sequence represented by Formula 5: $[REP4]_q$ (where, in Formula 5, q represents an integer of 4 to 300; REP4 represents the amino acid sequence consisting of Ser-J-j-Tyr-Gly-U-Pro; J represents any amino acid residue, and is particularly preferably an amino acid residue selected from the group consisting of Asp, Ser, and Thr; U is any amino acid residue, and is particularly preferably an amino acid residue selected from the group consisting of Pro, Ala, Thr, and Ser; and a plurality of REP4's may be the same amino acid sequence with each other or different amino acid sequences from each other). Specific examples thereof include a protein including the amino acid sequence set forth in SEQ ID NO: 28. The amino acid sequence set forth in SEQ ID NO: 28 is an amino acid sequence in which the amino acid sequence (a tag sequence and a hinge sequence) set forth in SEQ ID NO: 5 is added at the N-terminus of the amino acid sequence from 19th residue to 321st residue of the sequence in which Thr at 87th position is replaced by Ser, and Asn at 95th position is replaced by Asp, in the amino acid sequence of resilin (Accession No. NP611157, GI: 24654243 of NCBI GenBank).

Examples of proteins derived from elastin include a protein having an amino acid sequence such as Accession Nos. AAC98395 (human), 147076 (sheep), NP786966 (bovine), and the like of GenBank of NCBI. Specific examples thereof include a protein including the amino acid sequence set forth in SEQ ID NO: 29. The amino acid sequence set forth in SEQ ID NO: 29 is an amino acid sequence in which the amino acid sequence set forth in SEQ ID NO: 5 (a tag sequence and a hinge sequence) is added to the N-terminus of the amino acid sequence from 121st residue to 390th residue of the amino acid sequence of Accession No. AAC98395 of GenBank of NCBI.

The structural protein described above and the protein derived from the structural protein can be used alone or in combination of two or more kinds thereof.

A protein fiber and a protein contained as a main component in a protein raw fiber can be manufactured by, for example, expressing the nucleic acid by a nucleic acid sequence encoding the protein, and a host transformed with an expression vector having one or a plurality of regulatory sequences operably linked to the nucleic acid sequence.

A method for manufacturing a nucleic acid encoding the protein fiber and the protein contained in the protein raw fiber as the main component is not particularly limited. A nucleic acid can be manufactured by, for example, a method in which a gene encoding natural structural protein is amplified and cloned by polymerase chain reaction (PCR) or the like; or a method of chemically synthesizing a nucleic acid. A method for chemically synthesizing a nucleic acid is not particularly limited, and, for example, genes can be chemically synthesized by a method in which of linking, by PCR or the like, oligonucleotides that are automatically synthesized by AKTA oligopilot plus 10/100 (GE Healthcare Japan Ltd.) or the like, based on the amino acid sequence information of the structural protein obtained from the NCBI web database and the like. At this time, in order to facilitate purification and/or confirmation of the protein, a nucleic acid encoding the protein consisting of an amino acid sequence obtained by adding an amino acid sequence consisting of a start codon and a His10 tag to the N terminus of the above amino acid sequence may be synthesized.

The regulatory sequence is a sequence (for example, a promoter, an enhancer, a ribosome binding sequence, or a transcription termination sequence) that controls the expression of a recombinant protein in a host, and can be appropriately selected depending on the type of the host. As a promoter, an inducible promoter which functions in host cells and is capable of inducible expression of a target protein may be used. An inducible promoter is a promoter that can control transcription due to the presence of an inducer (expression inducer), the absence of a repressor molecule, or physical factors such as an increase or decrease in temperature, osmotic pressure, or pH value.

The type of the expression vector such as a plasmid vector, a viral vector, a cosmid vector, a fosmid vector, or an artificial chromosome vector can be appropriately selected depending on the type of the host. As the expression vector, an expression vector which can autonomously replicate in a host cell or can be incorporated into a chromosome of a host and which contains a promoter at a position capable of transcribing the nucleic acid encoding a target protein is suitably used.

Both prokaryotes and eukaryotes such as yeast, filamentous fungi, insect cells, animal cells, and plant cells can be suitably used as hosts.

Examples of hosts of the prokaryote include bacteria belonging to the genus *Escherichia, Brevibacillus, Serratia, Bacillus, Microbacterium, Brevibacterium, Corynebacterium* and *Pseudomonas*. Examples of microorganisms belonging to the genus *Escherichia* include *Escherichia coli* and the like. Examples of microorganisms belonging to the genus *Brevibacillus* include *Brevibacillus agri* and the like. Examples of microorganisms belonging to the genus *Serratia* include *Serratia liquefaciens* and the like. Examples of microorganisms belonging to the genus *Bacillus* include *Bacillus subtilis* and the like. Examples of microorganisms belonging to the genus *Microbacterium* include *Microbacterium ammoniaphilum*. Examples of microorganisms belonging to the genus *Brevibacterium* include *Brevibacterium divaricatum* and the like. Examples of microorganisms belonging to the genus *Corynebacterium* include *Corynebacterium ammoniagenes* and the like. Examples of microorganisms belonging to the genus *Pseudomonas* include *Pseudomonas putida* and the like.

In a case where a prokaryote is used as a host, examples of vectors into which a nucleic acid encoding a target protein is introduced include pBTrp2 (manufactured by Boehringer Mannheim), pGEX (manufactured by Pharmacia), pUC18, pBluescriptII, pSupex, pET22b, pCold, pUB110, and pNCO2 (Japanese Unexamined Patent Publication No. 2002-238569), and the like.

Examples of eukaryotic hosts include yeast and filamentous fungi (mold and the like). Examples of yeasts include a yeast which belongs to the genus *Saccharomyces, Pichia, Schizosaccharomyces*, and the like. Examples of filamentous fungi include filamentous fungi belonging to the genus *Aspergillus, Penicillium, Trichoderma*, and the like.

In a case where a eukaryote is used as a host, examples of vectors into which a nucleic acid encoding a target protein is introduced include YEP13 (ATCC37115), YEp24 (ATCC37051), and the like. As a method for introducing an expression vector into the foregoing host cell, any method can be used as long as it introduces DNA into the host cell. Examples thereof include a method using calcium ions [Proc. Natl. Acad. Sci. USA, 69, 2110 (1972)], an electroporation method, a spheroplast method, a protoplast method, a lithium acetate method, a competent method, and the like.

As a method for expressing a nucleic acid by a host transformed with an expression vector, secretory manufacture, fusion protein expression, or the like, in addition to direct expression, can be carried out according to the method described in Molecular Cloning, 2nd edition.

The protein can be manufactured, for example, by culturing a host transformed with the expression vector in a culture medium, manufacturing and accumulating the protein in the culture medium, and then collecting the protein from the culture medium. The method for culturing the host in a culture medium can be carried out according to a method commonly used for culturing a host.

In the case where the host is a prokaryote such as *Escherichia coli* or a eukaryote such as yeast, any of a natural medium and a synthetic medium may be used as a culture medium as long as it contains a carbon source, a nitrogen source, inorganic salts and the like which can be assimilated by the host and it is capable of efficiently culturing the host.

As the carbon source, any carbon source that can be assimilated by the transformed microorganism may be used. Examples of the carbon source that can be used include carbohydrates such as glucose, fructose, sucrose, and molasses, starch and starch hydrolyzates containing them, organic acids such as acetic acid and propionic acid, and alcohols such as ethanol and propanol. Examples of the nitrogen source that can be used include ammonium salts of inorganic or organic acids such as ammonia, ammonium chloride, ammonium sulfate, ammonium acetate and ammonium phosphate, other nitrogen-containing compounds, peptone, meat extract, yeast extract, corn steep liquor, casein hydrolyzate, soybean cake and soybean cake hydrolyzate, various fermented microbial cells and digested products thereof. As inorganic salts, it is possible to use potassium dihydrogen phosphate, dipotassium phosphate, magnesium phosphate, magnesium sulfate, sodium chloride, ferrous sulfate, manganese sulfate, copper sulfate, and calcium carbonate.

Culture of a prokaryote such as *Escherichia coli* or a eukaryote such as yeast can be carried out under aerobic conditions such as shaking culture or deep aeration stirring culture. The culture temperature is, for example, 15° C. to 40° C. The culture time is usually 16 hours to 7 days. It is preferable to maintain the pH of the culture medium during the culture at 3.0 to 9.0. The pH of the culture medium can be adjusted using an inorganic acid, an organic acid, an alkali solution, urea, calcium carbonate, ammonia, or the like.

In addition, antibiotics such as ampicillin and tetracycline may be added to the culture medium as necessary during the culture. In the case of culturing a microorganism transformed with an expression vector using an inducible promoter as a promoter, an inducer may be added to the medium as necessary. For example, in the case of culturing a microorganism transformed with an expression vector using a lac promoter, isopropyl-β-D-thiogalactopyranoside or the like is used, and in the case of culturing a microorganism transformed with an expression vector using a trp promoter, indole acrylic acid or the like may be added to the medium.

Isolation and purification of the expressed protein can be performed by a commonly used method. For example, in the case where the protein is expressed in a dissolved state in cells, the host cells are recovered by centrifugation after completion of the culture, suspended in an aqueous buffer solution, and then disrupted using an ultrasonicator, a French press, a Manton-Gaulin homogenizer, a Dyno-Mill, or the like to obtain a cell-free extract. From the supernatant obtained by centrifuging the cell-free extract, a purified preparation can be obtained by a method commonly used for protein isolation and purification, that is, a solvent extraction method, a salting-out method using ammonium sulfate or the like, a desalting method, a precipitation method using an organic solvent, an anion exchange chromatography method using a resin such as diethylaminoethyl (DEAE)-Sepharose or DIAION HPA-75 (manufactured by Mitsubishi Kasei Kogyo Kabushiki Kaisha), an cation exchange chromatography method using a resin such as S-Sepharose FF (Pharmacia Corporation), a hydrophobic chromatography method using a resin such as butyl sepharose or phenyl sepharose, a gel filtration method using a molecular sieve, an affinity chromatography method, a chromatofocusing method, an electrophoresis method such as isoelectric focusing or the like, alone or in combination thereof.

In the case where the protein is expressed by the formation of an insoluble matter in the cell, similarly, the host cells are recovered, disrupted and centrifuged to recover the insoluble matter of the protein as a precipitated fraction. The recovered insoluble matter of the protein can be solubilized with a protein denaturing agent. After this operation, a purified preparation of the protein can be obtained by the same isolation and purification method as described above. In the case where the protein is secreted extracellularly, the protein can be recovered from the culture supernatant. That is, a culture supernatant is obtained by treating the culture by a technique such as centrifugation, and a purified preparation can be obtained from the culture supernatant by using the same isolation and purification method as described above.

[Protein Raw Fiber]

Protein raw fiber is obtained by spinning the above-described protein, and contains the above-described protein as a main component. The protein raw fiber can be manufactured by a known spinning method. That is, for example, in a case of manufacturing the protein raw fiber containing the spider silk fibroin as a main component, first, a dope solution is produced by adding and dissolving the spider silk fibroin manufactured according to the method described above in a solvent such as dimethyl sulfoxide (DMSO), N,N-dimethylformamide (DMF), hexafluoroisopronol (HFIP), or formic acid, together with inorganic salt as a dissolution promoter. Next, using this dope solution, spinning is performed by a known spinning method such as wet-type spinning, dry-type spinning, dry-wet-type spinning, or melt spinning, and thereby a target protein raw fiber can be obtained.

Figure 3:
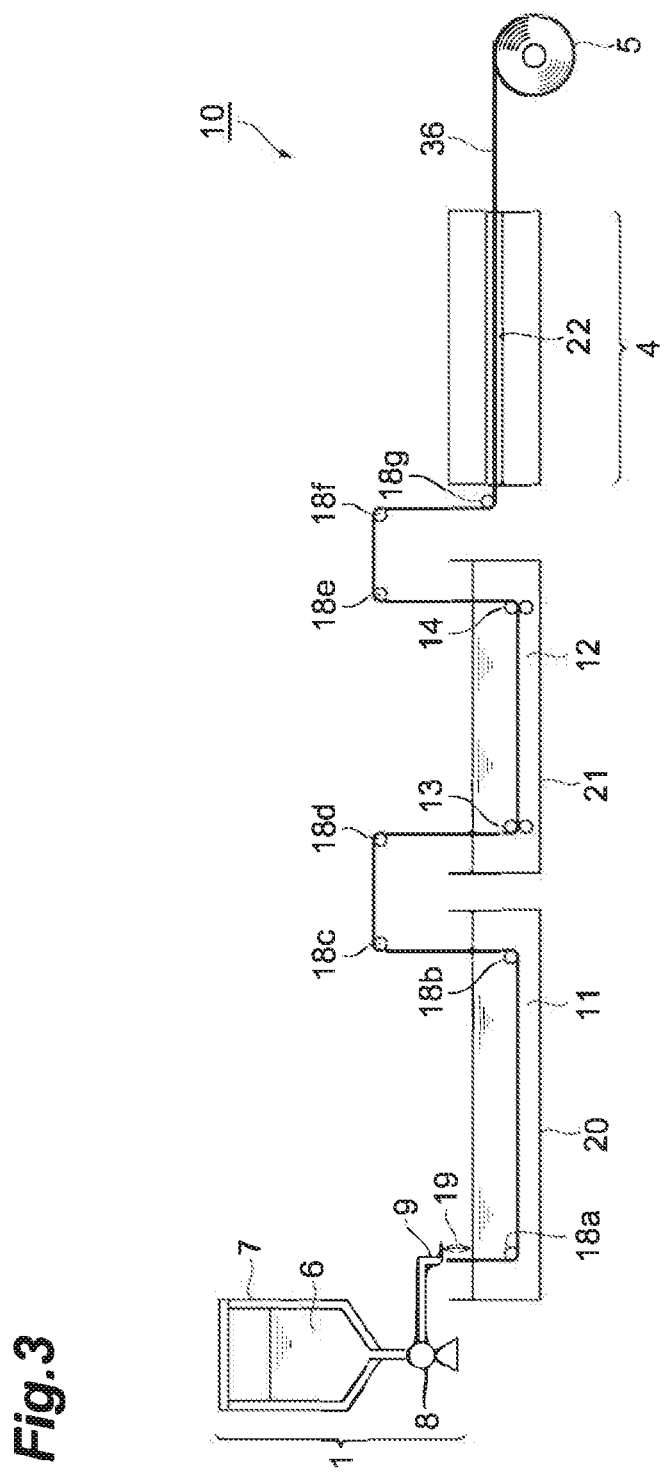
FIG. 3 is a schematic view showing an example of a spinning device for manufacturing a protein raw fiber.

FIG. 3 is a schematic view showing an example of a spinning device for manufacturing protein raw fibers. A spinning device 10 shown in FIG. 3 is an example of a spinning device for thy-wet-type spinning, and has an extrusion device 1, a coagulation bath 20, a washing bath 21, and a drying device 4 in this order from the upstream side.

The extrusion device 1 has a storage tank 7, in which a dope solution (spinning undiluted solution) 6 is stored. A coagulation liquid 11 (for example, methanol) is stored in the coagulation bath 20. The dope solution 6 is pushed out from a nozzle 9 provided by opening an air gap 19 between the dope solution 6 and the coagulation liquid 11, by a gear pump 8 attached to a lower end of the storage tank 7. The extruded dope solution 6 is supplied into the coagulation liquid 11 through the air gap 19. The solvent is removed from the dope solution 6 in the coagulation liquid 11 to coagulate the protein. The coagulated protein is guided to the washing bath 21 and washed with a washing solution 12 in the washing bath 21, and then sent to the drying device 4 by a first nip roller 13 and a second nip roller 14 installed in the washing bath 21. At this time, for example, in a case where a rotational speed of the second nip roller 14 is set to be faster than a rotational speed of the first nip roller 13, protein raw fibers 36 drawn at a magnification corresponding to the rotational speed ratio is obtained. The protein raw fibers drawn in the washing solution 12 are separated from the inside of the washing bath 21 and then is dried when passing through the drying device 4. Thereafter, the fibers are wound up by a winder. Accordingly, the protein raw fibers are obtained as a wound product 5 which is finally wound around the winder, by the spinning device 10. 18a to 18g are yarn guides.

The coagulation liquid 11 may be a solution capable of desolvation, and examples thereof include lower alcohols having 1 to 5 carbon atoms such as methanol, ethanol and 2-propanol, and acetone. The coagulation liquid 11 may appropriately contain water. The temperature of the coagulation liquid 11 is preferably 0° C. to 30° C. The distance the coagulated protein passes in the coagulation liquid 11 (substantially, the distance from the yarn guide 18a to the yarn guide 18b) may be any length that enables efficient desolvation, and is, for example, 200 to 500 mm. The residence time in the coagulation liquid 11 may be, for example, 0.01 to 3 minutes and preferably 0.05 to 0.15 minutes. Further, drawing (pre-drawing) may be carried out in the coagulation liquid 11.

For the drawing carried out in a case of obtaining the protein raw fiber, for example, wet heat drawing and dry heat drawing are also employed in addition to the above-described pre-drawing performed in the coagulation bath 20, and drawing performed in the washing bath 21.

The wet heat drawing can be carried out in warm water, in a solution obtained by adding an organic solvent or the like to warm water, or during steam heating. The temperature may be, for example, 50° C. to 90° C. and preferably 75° C. to 85° C. In wet heat drawing, undrawn yarn (or pre-drawn yarn) can be drawn, for example, 1 to 10 times, preferably 2 to 8 times.

Dry heat drawing can be carried out using an electric tube furnace, a dry heat plate, or the like. The temperature may be, for example, 140° C. to 270° C. and preferably 160° C.

to 230° C. In dry heat drawing, undrawn yarn (or pre-drawn yarn) can be drawn, for example, 0.5 to 8 times, preferably 1 to 4 times.

The wet heat drawing and the dry heat drawing may be carried out individually, or they may be carried out in multiple stages or in combination. That is, wet heat drawing and dry heat drawing can be carried out in an appropriate combination in such a manner that the first stage drawing is carried out by wet heat drawing and the second stage drawing is carried out by dry heat drawing, or the first stage drawing is carried out by wet heat drawing and the second stage drawing is carried out by wet heat drawing, and the third stage drawing is further carried out by dry heat drawing.

The lower limit of the final draw ratio is preferably more than 1 time, 2 times or more, 3 times or more, 4 times or more, 5 times or more, 6 times or more, 7 times or more, 8 times or more, or 9 times or more a draw ratio of the undrawn yarn (or pre-drawn yarn). The upper limit is preferably 40 times or less, 30 times or less, 20 times or less, 15 times or less, 14 times or less, 13 times or less, 12 times or less, 11 times or less, or 10 times or less.

[Extension and Contraction Step]

The extension and contraction step is a step of contracting or extending a protein raw fiber containing a protein by bringing the protein raw fiber into contact with a liquid or vapor. The fiber containing a protein can be contracted or extended upon contact with a liquid or vapor. The extension and contraction step is a step of naturally causing contraction or extension of a protein raw fiber by bringing the protein raw fiber into contact with a liquid or vapor, without external force. In short, the extension and contraction step is not a step of contracting or extending the protein raw fiber by an external force, such as by pulling the protein fiber in a length direction to extend it, or by not allowing a protein raw fiber to be contracted upon contact with water or hot water by immersing the protein raw fiber in water or hot water and the like in a state where both ends of the protein raw fiber are fixed to a predetermined frame. However, in the extension and contraction step, a tensile force or the like may be applied to the protein raw fiber within a range of allowing natural contraction or extension of the protein raw fiber due to contact between the protein raw fiber and a liquid or vapor. The extension and contraction step is preferably performed such that an amount of change in length in a fiber axis direction of the protein raw fibers due to contraction or extension is substantially the same amount as an amount of change in length when the protein raw fibers are naturally contracted or extended in a loosened state, without being tensioned. Thereby, in the next step (a drying step), by drying the protein raw fibers while adjusting a length thereof to an arbitrary length, an amount of change in length of the protein fibers when the obtained protein fibers are brought into contact with moisture for the first time can be controlled to be an amount corresponding to an "arbitrary length" (an amount corresponding to an "arbitrary length"—a "length before drying"). For example, by adjusting an amount of change in length of the protein raw fibers to be zero during the drying step, an amount of change in length (a contraction amount) of the protein fibers when they are brought into contact with moisture for the first time can be controlled to be zero or a value close to zero.

The extension and contraction step may be a step of naturally contracting protein raw fibers without external force by bringing the protein raw fibers into contact with a liquid or vapor, for example, by allowing a liquid or vapor to enter between fibers or within a fiber of the protein raw fibers (hereinafter will be referred to as the "contraction step"), or may be a step of naturally extending protein raw fibers without external force (hereinafter will be referred to as the "extension step").

In addition, it is considered that the natural contraction or extension of the protein raw fibers which does not depend on external force in the extension and contraction step occurs due to the following reasons, for example. That is, it is thought that the natural contraction of the protein raw fiber in the extension and contraction step occurs due to, for example, relaxation of a residual stress because of a liquid or vapor entering between fibers or within a fiber of the protein raw fibers having the residual stress due to stretching or the like in the manufacturing step. Meanwhile, natural extension of the protein raw fibers in the extension and contraction step is considered to be generated due to, for example, extremely little or no residual stress in the manufacturing process, and occurrence of swelling in a case where a liquid or vapor enters between fibers or within a fiber of the protein raw fibers contracted at the time of drying in the manufacturing step; or is considered to be generated in, for example, protein raw fibers that have been subjected to molecular design or the like such that that they are extended in a case where a liquid or vapor enters between fibers or within a fiber.

The type of the liquid or vapor used in the extension and contraction step is not particularly limited as long as it is a liquid or vapor that can naturally contract the protein raw fibers upon contact with the protein raw fibers, or is a liquid or vapor that can naturally extend the protein raw fibers. Among liquids or vapors, examples of liquids or vapors that naturally contract the protein raw fibers include a liquid or vapor which has a polarity. Examples of liquids having a polarity include water, tetrahydrofuran, acetonitrile, acetone, methanol, and the like. Among them, water is preferably used. This is because water is not only inexpensive and excellent in handleability, but also allows the protein raw fibers to be contracted more quickly and reliably upon contact with the protein raw fibers. Examples of vapors having a polarity include vapor of the liquid having a polarity described above, and among examples, water vapor is preferably used. This is because the water vapor can contract the protein raw fibers more quickly and reliably upon contact with the protein raw fibers, as in the case of water.

In the extension and contraction step, for example, in a case of performing a process of naturally contracting the protein raw fibers (hereinafter will be referred to as the "contraction process"), it is preferable to bring the protein raw fibers into contact with a liquid in a heated state. Thereby, a contraction time of the protein raw fibers can be further favorably shortened. From the same viewpoint, a liquid used in the contraction process is more preferably hot water (warmed water) rather than water.

When performing the contraction process using a warmed liquid, it is sufficient as long as a temperature of the liquid is lower than a temperature at which a protein contained in the protein raw fibers is decomposed or at which the protein raw fibers are thermally damaged. However, the upper limit value of the temperature of the liquid is preferably less than a boiling point in consideration of handling of the liquid and workability of the contraction step. In addition, from the viewpoint of sufficiently obtaining an effect of shortening a contraction time, the lower limit value of the temperature of the liquid is preferably 10° C. or more, is more preferably 40° C. or more, and is even more preferably 70° C. or more.

In the extension and contraction step, a method of bringing the liquid or vapor into contact with the protein raw fibers is not particularly limited. Examples of methods include a method of immersing protein raw fibers in a liquid; a method of spraying a liquid on protein raw fibers at normal temperature or spraying a liquid as a state of heated steam, and the like; a method of exposing protein raw fibers to a high-humidity environment filled with vapor; and the like. Among these methods, in the contraction process, the method of immersing protein raw fibers in a liquid is preferable, because a time required for contracting a predetermined amount of the protein raw fibers in the contraction process can be shortened effectively, and simplification and the like of contraction process equipment can be realized.

In the contraction step, when performing the contraction process, in a case where protein fibers in a loosened state are brought into contact with a liquid or vapor, protein raw fibers may not only be contracted but also be crimped like a wave in some cases. In order to prevent the occurrence of such crimp, for example, the contraction step may be carried out with the protein raw fibers which are not in a loosened state by performing the contraction process while tensioning (stretching) the protein raw fibers in a fiber axial direction, and the like.

In a case of performing the contraction process in a state where the protein raw fiber is not loosened, for example, a degree of tension (tensile force and the like) of the protein raw fibers is adjusted such that a contraction amount of protein raw fiber exceeds zero and becomes substantially equal to or less than a contraction amount when the protein raw fiber is naturally contracted in a loosened state without being tensioned. In addition, a degree of tension (tensile force and the like) of the protein raw fibers is preferably adjusted such that a contraction amount of protein raw fiber becomes substantially the same as a contraction amount when the protein raw fiber is naturally contracted in a loosened state without being tensioned. Accordingly, the protein raw fibers are more effectively prevented from being crimped, and furthermore, the protein raw fibers are contracted by the maximum amount or an amount close thereto. As a result, for example, by adjusting an amount of change in length of the protein raw fibers to be zero in the drying step after the contraction process, a change in length (a contraction amount) of the protein fibers when they are brought into contact with moisture for the first time can be controlled to be zero or a value close to zero. In the present specification, the phrase "substantially the same as" refers to the same amount or value, or an amount or value approximated thereto. In addition, the amount or value approximated thereto refers to an amount that can achieve the same effect as that obtained when the same amount or value is used.

[Drying Step]

The drying step is a step of drying the protein raw fiber that has undergone the extension and contraction step while adjusting a length thereof to an arbitrary length. As long as the drying step is performed so that the length of the protein raw fiber can be arbitrarily adjusted, a method of performing the drying step is not particularly limited. Drying may be, for example, natural drying or forced drying using a drying facility. As the drying equipment, any known drying equipment of contact type or non-contact type can be used. In addition, a drying temperature is not particularly limited as long as it is lower than, for example, a temperature at which proteins contained in the protein raw fibers are decomposed or at which the protein raw fibers are thermally damage. In general, the temperature is within a range of 20° C. to 150° C., and the temperature is preferably within a range of 50° C. to 100° C. When the temperature is within this range, the protein raw fibers are dried more quickly and efficiently without thermal damage to the protein raw fibers or decomposition of proteins contained in the protein raw fibers. A drying time is appropriately set in accordance with the drying temperature and the like, and for example, a time in which the influence of overdrying on the quality and physical properties of the protein raw fibers can be eliminated as much as possible.

A method for adjusting a length of the protein raw fiber to an arbitrary length in the drying step is not particularly limited. For example, in a case where the protein raw fibers are dried discontinuously for a predetermined length (so-called batch drying), as a method of making a change in length of the protein raw fibers in the drying zero, for example, a method of drying the protein raw fibers in a state where both ends of the protein raw fibers are fixed to a fixed frame or the like so that no tensile force is applied and no loosening occurs is adopted. Thereby, an amount of change in length of the protein raw fibers before and after drying can be made zero or an amount close thereto. In addition, as a method of lengthening a length of protein raw fibers in batch drying, for example, a method in which a tensile force is applied to protein raw fibers, and the protein raw fibers are dried in a state where a length of the protein raw fibers is extended to an arbitrary length is adopted. Thereby, protein raw fibers can be extended in drying, and a length after drying of protein raw fibers can be made longer than that before drying. In addition, as a method of shortening a length of protein raw fibers in batch drying, for example, a method in which protein raw fibers are dried in a state where the protein raw fibers are loosened and fixed in a fixed frame in which distances between the frames are smaller than a length of the protein raw fibers is adopted. Thereby, protein raw fibers are contracted in drying, and a length after drying of the protein raw fibers can be made shorter than that before drying.

Furthermore, for example, in a case of continuously drying wound protein raw fibers between rollers (so-called continuous drying) while running the wound protein raw fibers between a feeding roller and a winding roller, as a method of making a change in length of the protein raw fibers in drying zero, for example, a method of drying protein raw fibers by setting a feeding speed of the protein raw fibers by the feeding roller and a winding speed thereof of the winding roller to the same speed is adopted. Thereby, an amount of change in length of the protein raw fibers before and after drying can be made zero or an amount close thereto. In addition, as a method of lengthening a length of protein raw fibers in continuous drying, for example, a method of drying protein raw fibers with a winding speed of the protein raw fibers which is faster than a feeding speed thereof is adopted. Thereby, protein raw fibers are extended in drying, and a length after drying of the protein raw fibers can be made longer than that before drying. Furthermore, as a method of shortening a length of protein raw fibers in continuous drying, for example, a method of drying protein raw fibers with a winding speed of the protein raw fibers which is slower than a feeding speed thereof is adopted. Thereby, protein raw fibers are contracted in drying, and a length after drying of the protein raw fibers can be made shorter than that before drying.

Figure 4:
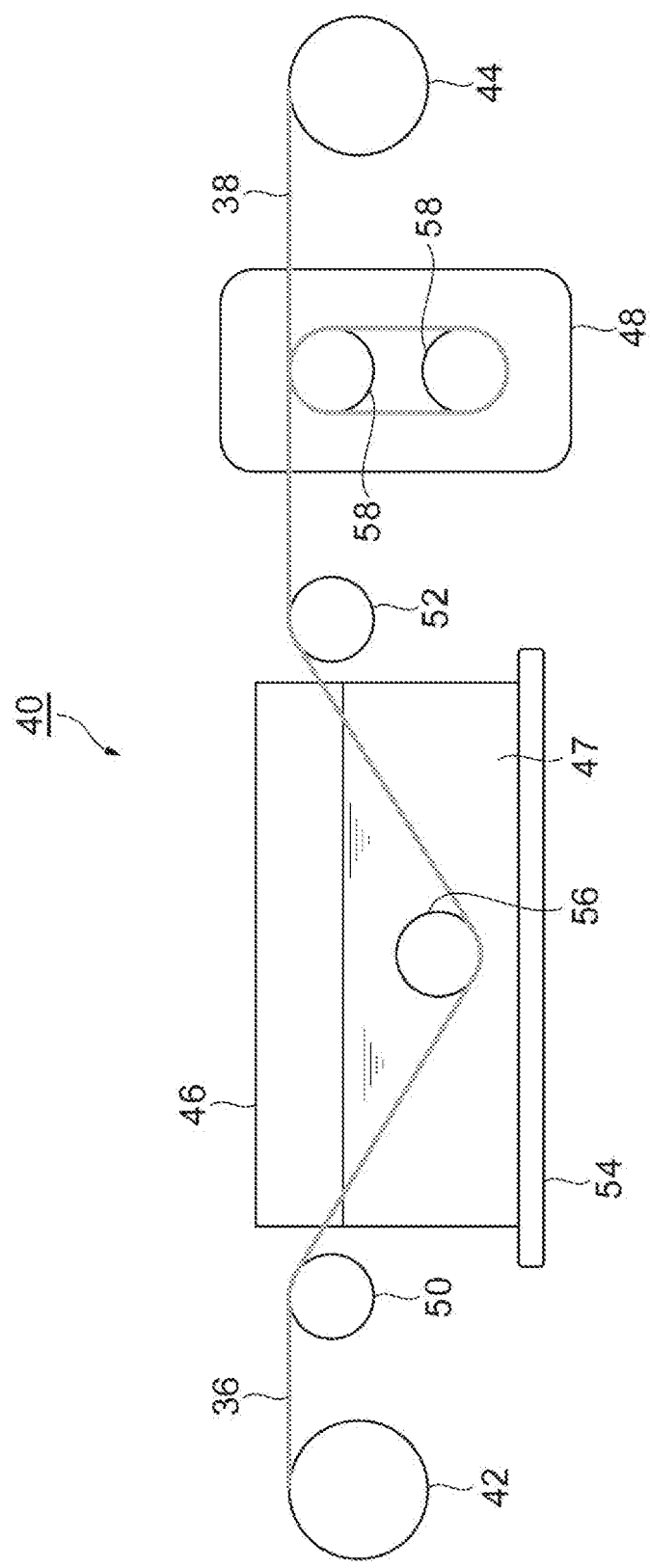
FIG. 4 is a schematic view showing an example of a manufacturing device for manufacturing a protein fiber.

FIG. 4 is a schematic view showing an example of a manufacturing device for manufacturing a protein fiber. A manufacturing device 40 shown in FIG. 4 is configured to include a feed roller 42 for delivering protein raw fibers, a winder 44 for winding protein raw fibers, a water bath 46 for performing an extension and contraction step, and a dryer 48 for performing a drying step.

More specifically, the feed roller 42 can be loaded with a wound product of protein raw fibers 36, and the protein raw fibers 36 are continuously automatically delivered from the wound product of the protein raw fibers 36 by rotation of an electric motor or the like (not shown). The winder 44 can continuously and automatically wind protein fibers 38 manufactured through the contraction step (the extension and contraction step) and the drying step to be described later after being fed out from the feed roller 42 by the rotation of an electric motor (not shown). A feed speed of the protein raw fibers 36 by the feed roller 42 and the winding speed of the protein fibers 38 by the winder 44 can be controlled independently of each other.

The water bath 46 and the dryer 48 are disposed between the feed roller 42 and the winder 44 respectively on the upstream side and the downstream side in a feeding direction of the protein raw fibers 36. The manufacturing device 40 shown in FIG. 4 has relay rollers 50 and 52 relaying the protein raw fibers 36 traveling from the feed roller 42 toward the winder 44.

The water bath 46 has a heater 54, and hot water 47 heated by the heater 54 is accommodated in the water bath 46. In addition, in the water bath 46, a tension roller 56 is installed in a state of being immersed in the hot water 47. Accordingly, the protein raw fibers 36 delivered from the feed roller 42 travel toward the winder 44 while being immersed in the hot water 47 in a state of being wound around the tension roller 56 in the water bath 46. An immersion time of the protein raw fibers 36 in the hot water 47 is appropriately controlled according to the traveling speed of the protein raw fibers 36.

The dryer 48 has a pair of hot rollers 58. The pair of hot rollers 58 can be wound with the protein raw fibers 36 which are separated from the water bath 46 and travel toward the winder 44 side. Accordingly, the protein raw fibers 36 immersed in the hot water 47 in the water bath 46 are heated by the pair of hot rollers 58 in the dryer 48 and dried, and then is further fed toward the winder 44.

When manufacturing the target protein fibers 38 using the manufacturing device 40 having such a structure, first, for example, the wound product 5 of the protein raw fibers 36 spun using the spinning device 10 shown in FIG. 3 is mounted on the feed roller 42. Next, the protein raw fibers 36 are continuously fed from the feed roller 42 and immersed in the hot water 47 in the water bath 46. At this time, for example, the winding speed of the winder 44 is made slower than the feed speed of the feed roller 42. Accordingly, the protein raw fibers 36 are naturally contracted by being brought into contact with the hot water 47 in a tensioned state so as not to be loosened between the feed roller 42 and the winder 44. In the present embodiment, the water bath 46 is configured with extension and contraction means that naturally contracts the protein raw fibers 36 to naturally change a length of the protein raw fibers 36 in a fiber axis direction, and the feed roller 42 and the winder 44 are configured with tensioning means. Because protein raw fibers having a residual stress due to stretching in the manufacturing process are used as the protein raw fibers 36, in a case where the protein raw fibers 36 are immersed in the hot water 47, the hot water 47 penetrates into the protein raw fibers 36, and the residual stress is relaxed, whereby the protein raw fibers 36 are naturally contracted.

When performing the contraction process (the extension and contraction step) on the protein raw fibers 36 as described above, by controlling a ratio of the feed speed of the feed roller 42 and the winding speed of the winder 44, it is possible to appropriately change a contraction amount of the protein raw fibers 36 in the hot water 47. For example, in a case of using protein raw fibers that are contracted by about 20% in a fiber axis direction when being immersed in the hot water 47 in a loosened state as the protein raw fibers 36, by controlling a winding speed of the winder 44 and a feed speed of the feed roller 42 so that the latter is about 80% of the former, without loosening the protein raw fibers 36 in the hot water 47, a contraction amount of the protein raw fibers 36 in the hot water 47 can be made substantially the same as a contraction amount when the protein raw fibers 36 are naturally contracted in a loosened state. In addition, in a case where the latter speed is faster than 80% of the former, by pulling the protein raw fibers 36 in the hot water 47, a contraction amount of the protein raw fibers 36 in the hot water 47 can be made smaller than a contraction amount when the protein raw fibers 36 are naturally contracted in a loosened state. On the other hand, in a case where the latter speed is slower than 80% of the former, the protein raw fibers 36 can be naturally contracted in a loosened state in the hot water 47.

Next, the protein raw fibers 36 contracted in the hot water 47 in the water bath 46 are heated by the pair of hot rollers 58 of the dryer 48. Thereby, the contracted protein raw fibers 36 are dried to form the protein fibers 38. At this time, by controlling a ratio of the feed speed of the feed roller 42 and the winding speed of the winder 44 so that a contraction amount of the protein raw fibers 36 when being immersed in hot water 47 becomes substantially the same as a contraction amount when the protein raw fibers 36 are naturally contracted in a loosened state, without contracting the protein raw fibers 36, the protein raw fibers 36 in a non-loosened state can be dried in a state where a length thereof is controlled so that a length after a contract process can be maintained, that is, a length after a contract process is not changed. As is clear from these findings, in the present embodiment, the drying means is constituted by a pair of hot rollers 58, and the adjustment means is constituted by the feed roller 42 and the winder 44, in addition to the tensioning means. Next, the obtained protein fibers 38 are wound on the winder 44, and thereby the wound product of the protein fibers 38 is obtained.

Instead of the pair of hot rollers 58, the protein raw fibers 36 may be dried using a drying facility which consists only of heat sources such as known dry heat plates and the like. Also in this case, by adjusting a relative speed between the feed speed of the feed roller 42 and the winding speed of the winder 44 in the same manner as in the case of using the pair of hot rollers 58 as a drying facility, the protein raw fibers 36 can be dried in a state in which a length after a contraction process is controlled so that it is not changed. Herein, the drying means is constituted by a dry heat plate.

As described above, by using the manufacturing device 40, the target protein fibers 38 can be manufactured automatically, continuously, and very easily. In addition, in particular, the protein fibers 38 has an amount of expansion and contraction of zero or a value close thereto when the protein fibers 38 are brought into contact with water for the first time after manufacture, the protein fiber 38 being manufactured by drying the protein raw fibers 36, in which a contraction amount in the hot water 47 is the maximum amount or an amount close thereto, such that a length of the protein raw fibers 36 is not changed by controlling a winding speed of the winder 44 and a feed speed of the feed roller 42. Accordingly, in such protein fibers 38, for example, when they are stored in a high-humidity environment after manufacture, contraction occurring when they are brought into contact with moisture for the first time after manufacture can be effectively suppressed in a case where an operation or process such as washing, wet heat setting, or dyeing, which brings the protein fibers 38 into contact with water for the first time after manufacture, is performed, and the like. As a result, a deterioration in quality and the like of the protein fibers 38 due to such contraction can be favorably prevented or suppressed.

FIG. 5 is a schematic view showing another example of the manufacturing device for manufacturing a protein fiber. FIG. 5(a) shows a contraction processing device that is included in the manufacturing device, and FIG. 5(b) shows a drying device that is included in the manufacturing device. The manufacturing device shown in FIG. 5 has a contraction processing device 60 as contraction means (extension and contraction means) for performing a contraction process (the extension and contraction step) on the protein raw fibers 36, and a drying device 62 for drying the protein raw fibers 36 on which the contraction process has been performed by the contraction processing device 60; and has a structure in which these devices are independently installed with each other.

More specifically, the contraction processing device 60 shown in FIG. 5(a) has a structure in which the dryer 48 is omitted from the manufacturing device 40 shown in FIG. 4, and the feed roller 42, the water bath 46, and the winder 44 are arranged in order from the upstream side to the downstream side in a traveling direction of the protein raw fibers 36. Such a contraction processing device 60 is designed to cause the protein raw fibers 36 delivered from the feed roller 42 to be immersed in hot water 47 in the water bath 46 and to be naturally contracted before being wound up by the winder 44. In addition, the structure is configured such that the protein raw fibers 36 naturally contracted in the hot water 47 is wound by the winder 44.

The drying device 62 shown in FIG. 5(b) has the feed roller 42 and the winder 44 as adjustment means, and the dry heat plate 64 as drying means. The dry heat plate 64 is disposed between the feed roller 42 and the winder 44 such that a dry heat surface 66 comes into contact with the protein raw fibers 36 and extends along the traveling direction thereof. As described above, for example, by making a winding speed of the winder 44 the same as a feed speed of the feed roller 42, or by increasing or decreasing a winding speed of the winder 44 by a predetermined amount with respect to a feed speed of the feed roller 42, the drying device 62 can perform drying such that lengths of the protein raw fibers 36 before and after drying become the same as each other, a length after drying becomes longer than a length before drying, or a length after drying becomes shorter than a length before drying.

In a case of using the manufacturing device having such a structure, for example, the target protein fibers 38 can be manufactured by firstly naturally contracting the protein raw fibers 36 by the contraction processing device 60, and then drying the protein raw fibers 36 by the drying device 62 while adjusting a length of the protein raw fibers 36. In addition, in the protein fibers 38 obtained in this manner, an amount of change in length when they are brought into contact with water and the like for the first time after manufacture is controlled to be an amount corresponding to an amount of length adjusted at the time of drying.

The feed roller 42 and the winder 44 may be omitted from the contraction processing device 60 shown in FIG. 5(a), and the contraction processing device may be configured with only the water bath 46. In a case of using the manufacturing device having such a contraction processing device, for example, protein fibers having a predetermined length are manufactured in a so-called batch system.

[Method for Processing Protein Fiber]

The method for manufacturing a protein fiber of the present invention described above can be perceived as a method for processing a protein fiber, including an extension and contraction step of contracting or extending a protein raw fiber containing a protein by bringing the protein raw fiber into contact with a liquid or vapor; and a drying step of drying the protein raw fiber that has undergone the extension and contraction step while adjusting a length of the protein raw fiber to an arbitrary length.

[Method for Manufacturing Fabric Made of Protein Fibers]

A method for manufacturing fabric made of protein fibers according to the present invention includes a step of producing fabric using the protein fiber obtained by the method for manufacturing a protein fiber according to the present invention. The method for producing fabric from the protein fibers is not particularly limited, and known methods can be used.

According to the method for manufacturing fabric made of protein fibers according to the present embodiment, by using protein fibers that have been subjected to the extension and contraction step and drying step as described above, it is possible to easily manufacture fabric made of protein fibers in which an unexpected length change can be prevented as much as possible when the protein fibers are brought into contact with moisture for the first time after manufacture.

Protein fibers used for manufacturing the fabric made of the protein fibers may be short fibers or long fibers. In addition, such protein fibers may be used alone or in combination with other fibers. In other words, in a case of manufacturing the fabric made of the protein fibers, as material yarns, a single yarn consisting only of protein fibers that have been subjected to the extension and contraction step and the drying step, and a composite yarn formed by combining protein fibers subjected to the extension and contraction step and the drying step with other fibers may be used alone, or may be used in combination thereof. In addition, the other fibers mean protein fibers which have not been subjected to the extension and contraction step and/or the drying step, fibers not containing a protein, and the like. Furthermore, examples of composite yarns include blended yarns, mixed yarns, covering yarns, and the like.

The type of fabric made of the protein fibers manufactured according to the method for manufacturing fabric made of protein fibers according to the present embodiment is also not particularly limited. The fabric made of the protein fibers may be, for example, a woven or knitted fabric, or may be a non-woven fabric. In addition, the woven fabric may be, for example, fabric in which a woven structure is plain weave, twill weave, satin weave, and the like, and the type of yarn used may be one kind or plural kinds. The knitted fabric may be, for example, a warp knitted fabric such as tricot or russell, may be a weft knitted fabric such as a weft knitted fabric or a circular knitted fabric, and the type of yarn used may be one kind or plural kinds.

EXAMPLES

Hereinafter, the present invention will be described more specifically with respect to Examples. However, the present invention is not limited to the following Examples.

<Test Example>
<1. Manufacture of Spider Silk Protein (Spider Silk Fibroin: PRT410)>
(Synthesis of Gene Encoding Spider Silk Protein and Construction of Expression Vector)

Based on the base sequence and amino acid sequence of a fibroin (GenBank Accession Number: P46804.1, GI: 1174415) derived from *Nephila clavipes*, a modified fibroin (hereinafter, will be referred to as "PRT410") having an amino acid sequence set forth in SEQ ID NO: 9 was designed.

With respect to the amino acid sequence of the fibroin derived from *Nephila clavipes*, the amino acid sequence set forth in SEQ ID NO: 9 has an amino acid sequence in which amino acid residues are substituted, inserted, and deleted for the purpose of improving productivity, and has the N-terminus to which the amino acid sequence (a tag sequence and a hinge sequence) set forth in SEQ ID NO: 5 is added.

Next, a nucleic acid encoding PRT410 was synthesized. In the nucleic acid, an NdeI site was added to the 5' end and an EcoRI site was added downstream of the stop codon. The nucleic acid was cloned into a cloning vector (pUC118). Thereafter, the same nucleic acid was cleaved by restriction enzyme treatment with NdeI and EcoRI, and then recombined into a protein expression vector pET-22b(+) to obtain an expression vector.

*Escherichia coli* BLR (DE3) was transformed with the obtained expression vector pET22b (+) containing the nucleic acid encoding PRT410. The transformed *Escherichia coli* was cultured in 2 mL of an LB medium containing ampicillin for 15 hours. The culture solution was added to 100 mL of a seed culture medium (Table 2) containing ampicillin so that the $OD_{600}$ was 0.005. The temperature of the culture solution was maintained at 30° C. and the flask culture was carried out (for about 15 hours) until the $OD_{600}$ reached 5, thereby obtaining a seed culture solution.

TABLE 2

| Seed culture medium | |
|---|---|
| Reagents | Concentration (g/L) |
| Glucose | 5.0 |
| $KH_2PO_4$ | 4.0 |
| $K_2HPO_4$ | 9.3 |
| Yeast Extract | 6.0 |
| Ampicillin | 0.1 |

The seed culture solution was added to a jar fermenter to which 500 ml of a production medium (Table 3) had been added so that the $OD_{600}$ was 0.05. The culture was carried out while maintaining the culture solution temperature at 37° C. and keeping the pH constant at 6.9. Further, the dissolved oxygen concentration in the culture solution was maintained at 20% of the dissolved oxygen saturation concentration.

TABLE 3

| Production medium | |
|---|---|
| Reagents | Concentration (g/L) |
| Glucose | 12.0 |
| $KH_2PO_4$ | 9.0 |
| $MgSO_4 \cdot 7H_2O$ | 2.4 |
| Yeast Extract | 15 |
| $FeSO_4 \cdot 7H_2O$ | 0.04 |
| $MnSO_4 \cdot 5H_2O$ | 0.04 |

TABLE 3-continued

| Production medium | |
|---|---|
| Reagents | Concentration (g/L) |
| $CaCl_2 \cdot 2H_2O$ | 0.04 |
| ADEKANOL (LG-295S, Adeka Corporation) | 0.1 (mL/L) |

Immediately after glucose in the production medium was completely consumed, a feed solution (455 g/1 L of glucose and 120 g/1 L of Yeast Extract) was added at a rate of 1 mL/min. The culture was carried out while maintaining the culture solution temperature at 37° C. and keeping the pH constant at 6.9. Further, the dissolved oxygen concentration in the culture solution was maintained at 20% of the dissolved oxygen saturation concentration, and the culture was carried out for 20 hours. Thereafter, 1 M isopropyl-β-thiogalactopyranoside (IPTG) was added to the culture solution to a final concentration of 1 mM to induce the expression of PRT410. Twenty hours after addition of IPTG, the culture solution was centrifuged to recover the bacterial cells. SDS-PAGE was carried out using the bacterial cells prepared from the culture solution before the addition of IPTG and after the addition of IPTG, and the expression of PRT410 was confirmed by the appearance of a band of a size of PRT410 depending on the addition of IPTG.

(Purification of PRT410)

The bacterial cells recovered 2 hours after the addition of IPTG were washed with 20 mM Tris-HCl buffer solution (pH 7.4). The bacterial cells after washing were suspended in 20 mM Tris-HCl buffer solution (pH 7.4) containing about 1 mM PMSF, and the cells were disrupted with a high-pressure homogenizer (available from GEA Niro Soavi SpA). The disrupted cells were centrifuged to obtain a precipitate. The obtained precipitate was washed with 20 mM Tris-HCl buffer solution (pH 7.4) until high purity. The precipitate after washing was suspended in 8 M guanidine buffer solution (8 M guanidine hydrochloride, 10 mM sodium dihydrogen phosphate, 20 mM NaCl, 1 mM Tris-HCl, pH 7.0) so as to have a concentration of 100 mg/mL, and dissolved by stirring with a stirrer at 60° C. for 30 minutes. After dissolution, dialysis was carried out with water using a dialysis tube (cellulose tube 36/32 manufactured by Sanko Junyaku Co., Ltd.). The white aggregated protein (PRT410) obtained after dialysis was recovered by centrifugation, the water content was removed with a freeze dryer, and the freeze-dried powder was recovered.

2. Manufacture of Protein Raw Fibers (Preparation of Dope Solution)

After adding spider fibroin (PRT410) mentioned above such that a concentration became 24% by mass to dimethyl sulfoxide (DMSO), a 4.0% by mass concentration of LiCl was added thereto as a dissolution promoter. Thereafter, the mixture was dissolved for 3 hours using a shaker. Thereafter, dust and bubbles were removed to obtain a dope solution. A solution viscosity of the dope solution was 5000 cP (centipoise) at 90° C.

(Spinning)

Using the dope solution obtained as described above and the spinning device 10 shown in FIG. 3, known dry-wet-type spinning was performed to obtain four wound products of protein raw fibers. The dry-wet-type spinning was performed under the following conditions.

Extrusion nozzle diameter: 0.1 mm
Coagulation liquid (methanol) temperature: 2° C.
Draw ratio: 4.52 times
Drying temperature: 80° C.

3. Method for Manufacturing Protein Fiber

Next, using the four wound products of protein raw fibers obtained as described above, and the manufacturing device 40 shown in FIG. 4, after subjecting each of the protein raw fibers fed from the four wound products to a contraction process under conditions shown in Table 4 using the manufacturing device 40 shown in FIG. 4, in a state where the protein raw fibers were not loosened, the protein raw fibers were dried at a temperature of 70° C. such that they were not pulled as much as possible (such that a length thereof was not changed as much as possible). Thereby, four types of wound products of protein fibers with different contraction process conditions were obtained. Thereafter, 20 cm of each of the four types of wound products of protein fibers was cut out to obtain four types of protein fibers (Examples 1 to 4) having the same length but with different contraction process conditions. In addition, protein raw fibers that were not subjected to the contraction process and drying were prepared in the same length as in Examples 1 to 4, and used as protein fibers for comparison (Comparative Example 1).

Next, using the protein fibers of Examples 1 to 4 and the protein fiber of Comparative Example 1 obtained as described above, 0.8 g of a lead weight was attached to each protein fiber, each protein fiber was immersed in hot water at 70° C. for 60 seconds, and a length of each protein fiber was measured in hot water. In addition, contraction percentages (%) when the protein fibers of Examples 1 to 4 and Comparative Example 1 were immersed in hot water were respectively calculated according to Equation 6. The results are also shown in Table 4. For performing the measurement of a length of the protein fibers in hot water, the 0.8 g lead weight was attached to the protein fibers in order to eliminate crimping of the protein fibers in hot water. In addition, 20 cm was substituted into Equation 6 as the length of the protein fibers before being immersed in hot water.

Contraction percentage=(length before immersion−length after immersion)/length before immersion×100   (Equation 6)

TABLE 4

| | Feed speed (m/min) | Winding speed (m/min) | Temperature of hot-water bath (° C.) | Staying time (s) | Contraction percentage (%) |
|---|---|---|---|---|---|
| Example 1 | 52 | 40 | 80 | 1.15 | 5.0 |
| Example 2 | 50 | 40 | 80 | 1.2 | 3.0 |
| Example 3 | 20 | 16 | 70 | 3 | 1.0 |
| Example 4 | 10 | 8 | 50 | 6 | 0 |
| Comparative Example 1 | — | — | — | — | 21.3 |

As is clear from the results in Table 4, although there were some differences in contraction percentages depending on an amount of tension during the contraction process and drying, a temperature of a hot-water bath during the contraction process, a time spent in the bath, and the like, contraction percentages of the protein fibers of Examples 1 to 4 when the protein fibers were immersed in hot water were 0% to 5%, which were sufficiently small value. In addition, when the appearance of the protein fibers of Examples 1 to 4 was visually checked, no crimping was observed in any of the protein fibers. In contrast, a contraction percentage of the protein fiber of Comparative Example 1 when the protein fiber was immersed in hot water was 21.3%, which an extremely large value.

Based on these findings, it could be clearly recognized that, according to the manufacturing method of the present invention, by continuously subjecting protein fibers to the contraction process (an extension and contraction step) to naturally contract the protein fibers, and to the step of drying while adjusting a length thereof such that the length is not changed, it is possible to easily produce protein fibers in which a contraction amount can be effectively suppressed when the protein fibers are brought into contact with moisture for the first time after manufacture. In addition, it could also be recognized that generation of crimping of the protein fibers can be prevented by subjecting protein raw fibers to the contraction process in a state where the protein raw fibers were not loosened. Furthermore, it was confirmed that an immersion time of the protein raw fibers in a hot-water bath can be shortened by increasing a temperature of the hot-water bath in which the protein raw fibers are immersed in the contraction process. Furthermore, it could be recognized that a contraction amount when protein fibers are brought into contact with water for the first time tends to be reduced by reducing an amount of tension of protein raw fibers that have been brought into a non-loosened state in a warm bath during the contraction process.

Test Example 2

Next, protein raw fibers having a predetermined length which were cut out from one wound product of protein raw fibers obtained in the same manner as in Test Example 1 were subjected to the extension and contraction step of immersing the protein raw fibers in hot water at 70° C. for 60 seconds. Thereafter, the protein raw fibers were taken out from the hot water, and immediately after that, they were cut at five places in a length of 30 cm in a state where they were undried and no load was applied. Thereby five protein raw fibers having the same length of 30 cm in the hot water were obtained. According to the verification through several experiments by the inventors of the present invention, when protein raw fibers were immersed in hot water at 70° C. for 60 seconds, and then taken out from the hot water, and a length of the protein raw fibers were measured immediately after that in a state where they were undried and no load was applied, it has been found that a length of the protein raw fibers was about 10% shorter than that measured in a state where protein raw fibers attached with a 0.8 g lead weight were immersed in hot water.

Next, one of the five protein raw fibers having a length of 30 cm was extended by 8 cm in an undried state so that a total length became 38 cm. Another one was extended by 4 cm in an undried state so that a total length became 34 cm. Both ends of each protein raw fiber were fixed on a surface of a predetermined plate so that their extended state was maintained. Thereafter, these two protein raw fibers were naturally dried by exposing them in an environment of a temperature of 20° C. and a relative humidity of 65% overnight to obtain two dried fibers. When a length of each of these two dried fibers was measured, a length of the dried fiber that was extended by 8 cm (a total length of 38 cm) was 37.5 cm, and a length of the dried fiber that was extended by 4 cm (a total length of 34 cm) was 33.5 cm. In this manner, a protein fiber (Example 5) to be obtained by immersing protein raw fibers in hot water to be naturally contracted, and then drying them while adjusting a length so that the length was extended by about 8 cm; and a protein fiber (Example 6) to be obtained by immersing protein raw fibers in hot water to be naturally contracted, and then drying them while adjusting a length so that the length was extended by about 4 cm were obtained.

In addition, one of the remaining three protein fibers was dried naturally in the same manner as in Examples 5 and 6 in a state where the protein fiber was not extended or loosened, and both ends thereof were fixed on a surface of a predetermined plate such that a length of 30 cm was maintained. Thereby a dried fiber was obtained. When a length of this dried fiber was measured, it was 30 cm. In this manner, a protein fiber (Example 7) to be obtained by immersing protein raw fibers in hot water to be naturally contracted, and then drying them while adjusting a length so that the length was not changed was obtained.

Furthermore, the remaining two protein raw fibers were used, and both ends thereof were fixed on a surface of a predetermined plate in a state where the protein raw fibers were loosened. At this time, a distance between both ends of one protein raw fiber was set to 28 cm, while a distance between both ends of the other protein raw fiber was set to 26 cm. Thereafter, these two protein raw fibers were naturally dried in the same manner as in Examples 5, 6, and 7, to obtain two dried fibers. When lengths of these two dried fibers were measured, a length of the dried fiber in which the distance between the both ends was set to 28 cm was 28 cm, and a length of the dried fiber in which the distance between the both ends was set to 26 cm was 26 cm. In this manner, a protein fiber (Example 8) to be obtained by immersing protein raw fibers in hot water to be naturally contracted, and then drying them while adjusting a length so that the length was shortened by about 2 cm; and a protein fiber (Example 9) to be obtained by immersing protein raw fibers in hot water to be naturally contracted, and then drying them while adjusting a length so that the length was shortened by about 4 cm were obtained.

Next, the five protein fibers of Examples 5 to 9 obtained as described above were cut into 20 cm pieces, and lengths thereof were made uniform. Subsequently, 0.8 g of lead weights were attached to the five protein fibers of Examples 5 to 9 having the same length of 20 cm, and each protein fiber was immersed in hot water at 70° C. for 60 seconds to measure a length of each protein fiber in the hot water. In addition, contraction percentages (%) when the protein fibers of Examples 5 to 9 were immersed in hot water were respectively calculated according to Equation 6. The results are shown in Table 5. The measurement of the protein fibers of Examples 5 to 9 in hot water was performed in the same manner as in Test Example 1 in which the protein fibers of Examples 1 to 4 were measured in hot water. In addition, in order to acquire contraction percentages under the same conditions as in Test Example 1 when the protein fibers of Examples 5 to 9 were immersed in hot water, 22 cm, to which a correction value of 2 cm corresponding to 10% of a length of 20 cm obtained by cutting a protein fiber in a dry state as a length before each protein fiber was immersed in hot water was added, was adopted, and this was substituted into Equation 6.

This is due to the following reason. That is, according to various experimental results by the inventors of the present invention, when the protein raw fibers that had been subjected to the extension and contraction step of immersing them in hot water at 70° C. for 60 seconds were taken out of the hot water, and a length of the protein raw fibers were measured immediately after that in a state where they were undried and no load was applied, it has been found that a length of the protein raw fibers was about 10% shorter than that measured in a state where protein raw fibers attached with a 0.8 g lead weight were immersed in hot water. Therefore, regarding the protein raw fibers which were immersed in hot water, at 70° C. for 60 seconds, and then taken out of the hot water, and cut immediately after that so that a measurement length became 30 cm in a state where they were undried and no load was applied (that is, the protein raw fibers that give the protein fibers of Examples 5 to 9), it is considered that a length in the state where the protein raw fibers attached with a 0.8 g lead weight were immersed in hot water is about 33 cm, which is an increase of 10%. In the present Test Example 2 in which the protein fibers cut to 20 cm after being dried were immersed in hot water, in order to set a length of the protein fibers measured in the state where the protein fibers attached with a 0.8 g lead weight were immersed in hot water to the same condition as in Test Example 1 in which the length of the protein fibers before immersion in hot water is used, the length of the protein fibers before immersion was set to 22 cm obtained by adding a correction value of 2 cm corresponding to 10% of the length of 20 cm.

TABLE 5

|  | Length after drying (cm) | Contraction percentage (%) |
|---|---|---|
| Example 5 | 37.5 | 22.7 |
| Example 6 | 34 | 11.4 |
| Example 7 | 30 | 0 |
| Example 8 | 28 | −9.1 |
| Example 9 | 26 | −18.2 |

As is clear from the results in Table 5, a length at the time of immersion in hot water is not changed in the case of the protein fiber of Example 7 to be obtained by immersing protein raw fibers in hot water to be naturally contracted, and then drying so that the length was not changed. In addition, the protein fibers of Example 5 and Example 6, which are to be obtained by immersing protein raw fibers in hot water to be naturally contracted, and then drying them while adjusting a length so that the length was lengthened, were contracted when being immersed in hot water by an amount corresponding to an amount of length adjusted at the time of drying. Furthermore, the protein fibers of Example 8 and Example 9, which are to be obtained by immersing protein raw fibers in hot water to be naturally contracted, and then drying them while adjusting a length so that the length was shortened, were extended when being immersed in hot water by an amount corresponding to an amount of length adjusted at the time of drying. These results clearly show that, by the manufacturing method of the present invention, it is possible to obtain protein fibers in which an amount of change in length when they are brought into contact with moisture for the first time after manufacture can be controlled arbitrarily, and an unexpected length change can be prevented.

REFERENCE SIGNS LIST

1: extrusion device, 4: drying device, 6: dope solution, 10: spinning device, 20: coagulation bath, 21: washing bath, 36: protein raw fiber, 38: protein fiber, 40: manufacturing device, 42: feed roller, 44: winder, 46: water bath, 48: dryer, 54: heater, 56: tension roller, 58: hot roller, 60: contraction processing device, 62: drying device

The invention claimed is:

1. A method for manufacturing a protein fiber, comprising:
an extension and contraction step of contracting or extending a protein raw fiber containing a protein by bringing the protein raw fiber into contact with a liquid or vapor; and
a drying step of drying the protein raw fiber that has undergone the extension and contraction step while adjusting a length of the protein raw fiber to an arbitrary length.

2. The method for manufacturing a protein fiber according to claim 1, wherein the extension and contraction step is a step of naturally contracting the protein raw fiber by bringing the protein raw fiber into contact with the liquid or vapor.

3. The method for manufacturing a protein fiber according to claim 2, wherein the extension and contraction step is performed in a state where the protein raw fiber is not loosened.

4. The method for manufacturing a protein fiber according to claim 3, wherein, in the extension and contraction step, the protein raw fiber is tensioned such that a contraction amount of the protein raw fiber is substantially the same as a contraction amount of the protein raw fiber in a case where the protein raw fiber is naturally contracted by being brought into contact with the liquid or vapor in a state where the protein raw fiber is loosened.

5. The method for manufacturing a protein fiber according to claim 1, wherein the protein is a structural protein.

6. The method for manufacturing a protein fiber according to claim 5, wherein the structural protein is a spider silk fibroin.

7. The method for manufacturing a protein fiber according to claim 1, wherein the liquid is a warmed liquid.

8. The method for manufacturing a protein fiber according to claim 1, wherein the extension and contraction step is performed by immersing the protein raw fiber in the liquid.

9. The method for manufacturing a protein fiber according to claim 1, wherein the liquid or vapor has a polarity.

10. The method for manufacturing a protein fiber according to claim 9, wherein the liquid is water or hot water, and the vapor is water vapor.

11. The method for manufacturing a protein fiber according to claim 1,
wherein the extension and contraction step and the drying step are performed with respect to the protein raw fiber fed continuously,
the method further comprising a step of continuously winding a protein fiber obtained through the extension and contraction step and the drying step.

12. The method for manufacturing a protein fiber according to claim 11, wherein a speed at which the protein fiber is wound is slower than a speed at which the protein raw fiber is fed, and is a speed at which the protein raw fiber is not loosened in the extension and contraction step.

13. A method for manufacturing fabric made of protein fibers, comprising a step of producing fabric using the protein fiber manufactured by the manufacturing method according to claim 1.

14. A method for processing a protein fiber, comprising:
an extension and contraction step of contracting or extending a protein raw fiber containing a protein by bringing the protein raw fiber into contact with a liquid or vapor; and
a drying step of drying the protein raw fiber that has undergone the extension and contraction step while adjusting a length of the protein raw fiber to an arbitrary length.

15. The method for processing a protein fiber according to claim 14, wherein the extension and contraction step is a step of naturally contracting a length of the protein raw fiber by bringing the protein raw fiber into contact with the liquid or vapor.

16. A device for manufacturing a protein fiber, comprising:
extension and contraction means for contracting or extending a protein raw fiber containing a protein by bringing the protein raw fiber into contact with a liquid or vapor that contracts or extends the protein raw fiber upon contact with the protein raw fiber;
drying means for drying the protein raw fiber contracted or extended by the extension and contraction means; and
adjustment means for adjusting a length of the protein raw fiber to an arbitrary length during drying of the protein raw fiber by the drying means.

17. The device for manufacturing a protein fiber according to claim 16, wherein the extension and contraction means is configured to naturally contract the protein raw fiber by bringing the protein raw fiber into contact with the liquid or vapor.

18. The device for manufacturing a protein fiber according to claim 17, further comprising tensioning means for tensioning the protein raw fiber such that the contraction of the protein raw fiber by the extension and contraction means is performed in a state where the protein raw fiber is not loosened.

* * * * *

SEQUENCE LISTING

<160> NUMBER OF SEQ ID NOS: 29

<210> SEQ ID NO 1
<211> LENGTH: 597
<212> TYPE: PRT
<213> ORGANISM: Artificial Sequence
<220> FEATURE:
<223> OTHER INFORMATION: Met-PRT313

<400> SEQUENCE: 1

Met Gly Pro Gly Gly Gln Gly Pro Tyr Gly Pro Gly Ala Ser Ala Ala
1               5                   10                  15

Ala Ala Ala Gly Gly Asn Gly Pro Gly Ser Gly Gln Gln Gly Pro Gly
                20                  25                  30

Gly Ser Ala Ala Ala Ala Gly Gly Tyr Gly Pro Gly Gly Gln Gly
            35                  40                  45

Pro Gly Gln Gln Gly Pro Gly Ser Ser Ala Ala Ala Ala Gly Pro
50                  55                  60

Gly Gly Tyr Gly Pro Gly Gln Gly Pro Ser Ala Ser Ala Ala Ala
65                  70                  75                  80

Ala Ala Gly Pro Gly Ser Gly Gln Gln Gly Pro Gly Ala Ser Ala Ala
                85                  90                  95

Ala Ala Ala Gly Gly Tyr Gly Pro Gly Gly Gln Gly Pro Gly Gln Gln
            100                 105                 110

Gly Pro Gly Ser Ser Ala Ala Ala Ala Gly Gly Tyr Gly Ser Gly
        115                 120                 125

Pro Gly Gln Gln Gly Pro Tyr Gly Ser Ala Ala Ala Ala Gly Pro
    130                 135                 140

Gly Ser Gly Gly Tyr Gly Gln Gly Pro Tyr Gly Pro Gly Ala Ser Ala
145                 150                 155                 160

Ala Ala Ala Gly Pro Gly Gly Tyr Gly Pro Gly Gly Gln Gly Pro
            165                 170                 175

Ser Ala Ser Ala Ala Ala Ala Gly Ser Gly Gln Gln Gly Pro Gly
        180                 185                 190

Gly Tyr Gly Pro Tyr Ala Ser Ala Ala Ala Ala Gly Gly Tyr Gly
    195                 200                 205

Ser Gly Pro Gly Gln Gln Gly Pro Tyr Gly Pro Gly Gly Ser Ala Ala
    210                 215                 220

Ala Ala Ala Gly Ser Gly Gln Gln Gly Pro Gly Gln Gln Gly Pro Tyr
225                 230                 235                 240

Ala Ser Ala Ala Ala Ala Gly Pro Gly Gly Gln Gly Pro Tyr Gly
        245                 250                 255

Pro Gly Ser Ser Ala Ala Ala Ala Gly Gly Tyr Gly Tyr Gly Pro
    260                 265                 270

Gly Gly Gln Gly Pro Tyr Gly Pro Gly Ala Ser Ala Ala Ala Ala
    275                 280                 285

Gly Gly Asn Gly Pro Gly Ser Gly Tyr Gly Pro Gly Gln Gln Gly
    290                 295                 300

Pro Gly Gly Ser Ala Ala Ala Ala Gly Pro Gly Gln Gly Pro
305                 310                 315                 320

Tyr Gly Pro Gly Ala Ser Ala Ala Ala Ala Gly Tyr Gly Pro
            325                 330                 335

Gly Gly Gln Gly Pro Gly Gly Tyr Gly Pro Gly Ser Ser Ala Ala Ala
        340                 345                 350

Ala Ala Gly Pro Gly Gly Gln Gly Pro Tyr Gly Pro Gly Ser Ser Ala

```
            355                 360                 365

Ala Ala Ala Ala Gly Gly Tyr Gly Pro Gly Gln Gln Gly Pro Tyr Gly
        370                 375                 380

Pro Gly Gly Ser Ala Ala Ala Ala Gly Gly Tyr Gln Gln Gly Pro
385                 390                 395                 400

Gly Gly Gln Gly Pro Tyr Gly Pro Gly Ala Ser Ala Ala Ala Ala
                405                 410                 415

Gly Pro Gly Gly Gln Gly Pro Tyr Gly Pro Ala Ser Ala Ala Ala
                420                 425                 430

Ala Ala Gly Pro Gly Gly Tyr Gly Pro Gly Gln Gly Pro Ser Ala
            435                 440                 445

Ser Ala Ala Ala Ala Gly Gly Tyr Gly Ser Gly Pro Gly Gly Tyr
        450                 455                 460

Gly Pro Tyr Gly Pro Gly Gly Ser Ala Ala Ala Ala Gly Pro Gly
465                 470                 475                 480

Ser Gly Gln Gln Gly Gln Gly Pro Tyr Gly Pro Gly Ala Ser Ala Ala
                485                 490                 495

Ala Ala Ala Gly Gly Tyr Gly Pro Gly Gln Gln Gly Pro Tyr Gly Pro
            500                 505                 510

Gly Gly Ser Ala Ala Ala Ala Gly Pro Gly Ser Gly Gly Tyr Gly
        515                 520                 525

Pro Gly Ala Ser Ala Ala Ala Ala Gly Gly Asn Gly Pro Gly Ser
530                 535                 540

Gly Gly Tyr Gly Pro Gly Gln Gln Gly Pro Gly Gly Ser Ala Ala Ala
545                 550                 555                 560

Ala Ala Gly Gly Tyr Gln Gln Gly Pro Gly Gln Gly Pro Tyr Gly
            565                 570                 575

Pro Gly Ala Ser Ala Ala Ala Ala Gly Pro Gly Ser Gly Gln Gln
            580                 585                 590

Gly Pro Gly Ala Ser
        595

<210> SEQ ID NO 2
<211> LENGTH: 590
<212> TYPE: PRT
<213> ORGANISM: Artificial Sequence
<220> FEATURE:
<223> OTHER INFORMATION: Met-PRT399

<400> SEQUENCE: 2

Met Gly Pro Gly Gly Gln Gly Pro Tyr Gly Pro Gly Ala Ser Ala Ala
1               5                   10                  15

Ala Ala Ala Gly Gly Asn Gly Pro Gly Ser Gly Gln Gln Gly Pro Gly
            20                  25                  30

Gly Ser Gly Gly Tyr Gly Pro Gly Gln Gly Pro Gly Gln Gln Gly
        35                  40                  45

Pro Gly Ser Ser Ala Ala Ala Ala Gly Pro Gly Tyr Gly Pro
    50                  55                  60

Gly Gly Gln Gly Pro Ser Ala Ser Ala Ala Ala Ala Gly Pro Gly
65                  70                  75                  80

Ser Gly Gln Gln Gly Pro Gly Ala Ser Gly Gly Tyr Gly Pro Gly Gly
                85                  90                  95

Gln Gly Pro Gly Gln Gln Gly Pro Gly Ser Ser Ala Ala Ala Ala
            100                 105                 110

Gly Gly Tyr Gly Ser Gly Pro Gly Gln Gln Gly Pro Tyr Gly Ser Ala
```

```
            115                 120                 125
Ala Ala Ala Gly Pro Gly Ser Gly Gly Tyr Gly Gln Gly Pro Tyr
130                 135                 140
Gly Pro Gly Ala Ser Gly Pro Gly Gly Tyr Gly Pro Gly Gln Gly
145                 150                 155                 160
Pro Ser Ala Ser Ala Ala Ala Ala Gly Ser Gln Gln Gly Pro
                165                 170             175
Gly Gly Tyr Gly Pro Tyr Ala Ser Ala Ala Ala Ala Gly Gly Tyr
            180                 185                 190
Gly Ser Gly Pro Gly Gln Gln Gly Pro Tyr Gly Pro Gly Ser Gly
            195                 200                 205
Ser Gly Gln Gln Gly Pro Gly Gln Gln Gly Pro Tyr Ala Ser Ala Ala
            210                 215                 220
Ala Ala Ala Gly Pro Gly Gln Gly Pro Tyr Gly Pro Gly Ser Ser
225                 230                 235                 240
Ala Ala Ala Ala Ala Gly Gly Tyr Gly Tyr Gly Pro Gly Gln Gly
                245                 250                 255
Pro Tyr Gly Pro Gly Ala Ser Gly Gly Asn Gly Pro Gly Ser Gly Gly
                260                 265                 270
Tyr Gly Pro Gly Gln Gln Gly Pro Gly Ser Ala Ala Ala Ala Ala
            275                 280                 285
Gly Pro Gly Gln Gly Pro Tyr Gly Pro Gly Ala Ser Ala Ala Ala
            290                 295                 300
Ala Ala Gly Gly Tyr Gly Pro Gly Gln Gly Pro Gly Gly Tyr Gly
305                 310                 315                 320
Pro Gly Ser Ser Gly Pro Gly Gln Gly Pro Tyr Gly Pro Gly Ser
                325                 330                 335
Ser Ala Ala Ala Ala Gly Gly Tyr Gly Pro Gly Gln Gln Gly Pro
                340                 345                 350
Tyr Gly Pro Gly Gly Ser Ala Ala Ala Ala Gly Gly Tyr Gln Gln
            355                 360                 365
Gly Pro Gly Gly Gln Gly Pro Tyr Gly Pro Gly Ala Ser Gly Pro Gly
            370                 375                 380
Gly Gln Gly Pro Tyr Gly Pro Gly Ala Ser Ala Ala Ala Ala Gly
385                 390                 395                 400
Pro Gly Gly Tyr Gly Pro Gly Gln Gly Pro Ser Ala Ser Ala Ala
                405                 410                 415
Ala Ala Ala Gly Gly Tyr Gly Ser Gly Pro Gly Gly Tyr Gly Pro Tyr
            420                 425                 430
Gly Pro Gly Gly Ser Gly Pro Gly Ser Gln Gln Gly Gln Gly Pro
            435                 440                 445
Tyr Gly Pro Gly Ala Ser Ala Ala Ala Ala Gly Gly Tyr Gly Pro
            450                 455                 460
Gly Gln Gln Gly Pro Tyr Gly Pro Gly Ser Ala Ala Ala Ala
465                 470                 475                 480
Gly Pro Gly Ser Gly Gly Tyr Gly Pro Gly Ala Ser Gly Gly Asn Gly
                485                 490                 495
Pro Gly Ser Gly Gly Tyr Gly Pro Gly Gln Gln Gly Pro Gly Gly Ser
                500                 505                 510
Ala Ala Ala Ala Ala Gly Gly Tyr Gln Gln Gly Pro Gly Gly Gln Gly
            515                 520                 525
Pro Tyr Gly Pro Gly Ala Ser Ala Ala Ala Ala Gly Gly Tyr Gly
            530                 535                 540
```

```
Ser Gly Pro Gly Gln Gln Gly Pro Tyr Gly Pro Gly Ser Gly Ser
545                 550                 555                 560

Gly Gln Gln Gly Pro Gly Gln Gly Pro Tyr Ala Ser Ala Ala Ala
                565                 570                 575

Ala Ala Gly Pro Gly Ser Gly Gln Gln Gly Pro Gly Ala Ser
        580                 585                 590

<210> SEQ ID NO 3
<211> LENGTH: 597
<212> TYPE: PRT
<213> ORGANISM: Artificial Sequence
<220> FEATURE:
<223> OTHER INFORMATION: Met-PRT380

<400> SEQUENCE: 3

Met Gly Pro Gly Gln Gln Gly Pro Tyr Gly Pro Gly Ala Ser Ala Ala
1               5                   10                  15

Ala Ala Ala Gly Gln Asn Gly Pro Gly Ser Gly Gln Gln Gly Pro Gly
            20                  25                  30

Gln Ser Ala Ala Ala Ala Gly Gln Tyr Gly Pro Gly Gln Gln Gly
        35                  40                  45

Pro Gly Gln Gln Gly Pro Gly Ser Ser Ala Ala Ala Ala Gly Pro
50                  55                  60

Gly Gln Tyr Gly Pro Gly Gln Gln Gly Pro Ser Ala Ser Ala Ala Ala
65                  70                  75                  80

Ala Ala Gly Pro Gly Ser Gly Gln Gln Gly Pro Gly Ala Ser Ala Ala
            85                  90                  95

Ala Ala Ala Gly Gln Tyr Gly Pro Gly Gln Gln Gly Pro Gly Gln Gln
            100                 105                 110

Gly Pro Gly Ser Ser Ala Ala Ala Ala Gly Gln Tyr Gly Ser Gly
        115                 120                 125

Pro Gly Gln Gln Gly Pro Tyr Gly Ser Ala Ala Ala Ala Gly Pro
130                 135                 140

Gly Ser Gly Gln Tyr Gly Gln Gly Pro Tyr Gly Pro Gly Ala Ser Ala
145                 150                 155                 160

Ala Ala Ala Gly Pro Gly Gln Tyr Gly Pro Gly Gln Gln Gly Pro
            165                 170                 175

Ser Ala Ser Ala Ala Ala Ala Gly Ser Gly Gln Gln Gly Pro Gly
        180                 185                 190

Gln Tyr Gly Pro Tyr Ala Ser Ala Ala Ala Ala Gly Gln Tyr Gly
        195                 200                 205

Ser Gly Pro Gly Gln Gln Gly Pro Tyr Gly Pro Gly Gln Ser Ala Ala
210                 215                 220

Ala Ala Ala Gly Ser Gly Gln Gln Gly Pro Gln Gly Pro Gly Pro Tyr
225                 230                 235                 240

Ala Ser Ala Ala Ala Ala Gly Pro Gly Gln Gln Gly Pro Tyr Gly
        245                 250                 255

Pro Gly Ser Ser Ala Ala Ala Ala Gly Gln Tyr Gly Tyr Gly Pro
        260                 265                 270

Gly Gln Gln Gly Pro Tyr Gly Pro Gly Ala Ser Ala Ala Ala Ala
        275                 280                 285

Gly Gln Asn Gly Pro Gly Ser Gly Gln Tyr Gly Pro Gly Gln Gln Gly
        290                 295                 300

Pro Gly Gln Ser Ala Ala Ala Ala Ala Gly Pro Gly Gln Gln Gly Pro
305                 310                 315                 320
```

-continued

Tyr Gly Pro Gly Ala Ser Ala Ala Ala Ala Gly Gln Tyr Gly Pro
                325                 330                 335

Gly Gln Gln Gly Pro Gly Gln Tyr Gly Pro Gly Ser Ser Ala Ala
            340                 345                 350

Ala Ala Gly Pro Gly Gln Gln Gly Pro Tyr Gly Pro Gly Ser Ser Ala
            355                 360                 365

Ala Ala Ala Gly Gln Tyr Gly Pro Gly Gln Gln Gly Pro Tyr Gly
        370                 375                 380

Pro Gly Gln Ser Ala Ala Ala Ala Gly Gln Tyr Gln Gln Gly Pro
385                 390                 395                 400

Gly Gln Gln Gly Pro Tyr Gly Pro Gly Ala Ser Ala Ala Ala Ala
            405                 410                 415

Gly Pro Gly Gln Gln Gly Pro Tyr Gly Pro Gly Ala Ser Ala Ala
            420                 425                 430

Ala Ala Gly Pro Gly Gln Tyr Gly Pro Gly Gln Gln Gly Pro Ser Ala
            435                 440                 445

Ser Ala Ala Ala Ala Gly Gln Tyr Gly Ser Gly Pro Gly Gln Tyr
    450                 455                 460

Gly Pro Tyr Gly Pro Gly Gln Ser Ala Ala Ala Ala Gly Pro Gly
465                 470                 475                 480

Ser Gly Gln Gln Gly Gln Gly Pro Tyr Gly Pro Gly Ala Ser Ala Ala
            485                 490                 495

Ala Ala Ala Gly Gln Tyr Gly Pro Gly Gln Gln Gly Pro Tyr Gly Pro
            500                 505                 510

Gly Gln Ser Ala Ala Ala Ala Gly Pro Gly Ser Gly Gln Tyr Gly
        515                 520                 525

Pro Gly Ala Ser Ala Ala Ala Ala Gly Gln Asn Gly Pro Gly Ser
530                 535                 540

Gly Gln Tyr Gly Pro Gly Gln Gly Pro Gln Ser Ala Ala Ala
545                 550                 555                 560

Ala Ala Gly Gln Tyr Gln Gln Gly Pro Gly Gln Gln Gly Pro Tyr Gly
            565                 570                 575

Pro Gly Ala Ser Ala Ala Ala Ala Gly Pro Gly Ser Gly Gln Gln
            580                 585                 590

Gly Pro Gly Ala Ser
        595

<210> SEQ ID NO 4
<211> LENGTH: 590
<212> TYPE: PRT
<213> ORGANISM: Artificial Sequence
<220> FEATURE:
<223> OTHER INFORMATION: Met-PRT410

<400> SEQUENCE: 4

Met Gly Pro Gly Gln Gln Gly Pro Tyr Gly Pro Gly Ala Ser Ala Ala
1               5                   10                  15

Ala Ala Ala Gly Gln Asn Gly Pro Gly Ser Gly Gln Gln Gly Pro Gly
            20                  25                  30

Gln Ser Gly Gln Tyr Gly Pro Gly Gln Gly Pro Gln Gln Gly
        35                  40                  45

Pro Gly Ser Ser Ala Ala Ala Ala Gly Pro Gly Gln Tyr Gly Pro
    50                  55                  60

Gly Gln Gln Gly Pro Ser Ala Ser Ala Ala Ala Ala Gly Pro Gly
65                  70                  75                  80

Ser Gly Gln Gln Gly Pro Ala Ser Gly Gln Tyr Gly Pro Gly Gln
                85                  90                  95

Gln Gly Pro Gly Gln Gly Pro Gly Ser Ser Ala Ala Ala Ala Ala
            100                 105                 110

Gly Gln Tyr Gly Ser Gly Pro Gly Gln Gln Gly Pro Tyr Gly Ser Ala
            115                 120                 125

Ala Ala Ala Ala Gly Pro Gly Ser Gln Tyr Gly Gln Gly Pro Tyr
130                 135                 140

Gly Pro Gly Ala Ser Gly Pro Gly Gln Tyr Gly Pro Gly Gln Gln Gly
145                 150                 155                 160

Pro Ser Ala Ser Ala Ala Ala Ala Ala Gly Ser Gly Gln Gln Gly Pro
                165                 170                 175

Gly Gln Tyr Gly Pro Tyr Ala Ser Ala Ala Ala Ala Gly Gln Tyr
            180                 185                 190

Gly Ser Gly Pro Gly Gln Gln Gly Pro Tyr Gly Pro Gly Gln Ser Gly
            195                 200                 205

Ser Gly Gln Gln Gly Pro Gly Gln Gln Gly Pro Tyr Ala Ser Ala Ala
            210                 215                 220

Ala Ala Ala Gly Pro Gly Gln Gln Gly Pro Tyr Gly Pro Gly Ser Ser
225                 230                 235                 240

Ala Ala Ala Ala Ala Gly Gln Tyr Gly Tyr Gly Pro Gly Gln Gln Gly
                245                 250                 255

Pro Tyr Gly Pro Gly Ala Ser Gly Gln Asn Gly Pro Gly Ser Gly Gln
            260                 265                 270

Tyr Gly Pro Gly Gln Gln Gly Pro Gly Gln Ser Ala Ala Ala Ala Ala
            275                 280                 285

Gly Pro Gly Gln Gln Gly Pro Tyr Gly Pro Gly Ala Ser Ala Ala Ala
            290                 295                 300

Ala Ala Gly Gln Tyr Gly Pro Gly Gln Gln Gly Pro Gly Gln Tyr Gly
305                 310                 315                 320

Pro Gly Ser Ser Gly Pro Gly Gln Gln Gly Pro Tyr Gly Pro Gly Ser
            325                 330                 335

Ser Ala Ala Ala Ala Ala Gly Gln Tyr Gly Pro Gly Gln Gln Gly Pro
                340                 345                 350

Tyr Gly Pro Gly Gln Ser Ala Ala Ala Ala Ala Gly Gln Tyr Gln Gln
            355                 360                 365

Gly Pro Gly Gln Gln Gly Pro Tyr Gly Pro Gly Ala Ser Gly Pro Gly
            370                 375                 380

Gln Gln Gly Pro Tyr Gly Pro Gly Ala Ser Ala Ala Ala Ala Ala Gly
385                 390                 395                 400

Pro Gly Gln Tyr Gly Pro Gly Gln Gln Gly Pro Ser Ala Ser Ala Ala
            405                 410                 415

Ala Ala Ala Gly Gln Tyr Gly Ser Gly Pro Gly Gln Tyr Gly Pro Tyr
            420                 425                 430

Gly Pro Gly Gln Ser Gly Pro Gly Ser Gly Gln Gln Gly Gln Gly Pro
            435                 440                 445

Tyr Gly Pro Gly Ala Ser Ala Ala Ala Ala Gly Gln Tyr Gly Pro
            450                 455                 460

Gly Gln Gln Gly Pro Tyr Gly Pro Gly Gln Ser Ala Ala Ala Ala Ala
465                 470                 475                 480

Gly Pro Gly Ser Gly Gln Tyr Gly Pro Gly Ala Ser Gly Gln Asn Gly
            485                 490                 495

```
Pro Gly Ser Gly Gln Tyr Gly Pro Gly Gln Gly Pro Gly Gln Ser
            500                 505                 510

Ala Ala Ala Ala Ala Gly Gln Tyr Gln Gln Gly Pro Gly Gln Gln
        515                 520                 525

Pro Tyr Gly Pro Gly Ala Ser Ala Ala Ala Ala Gly Gln Tyr Gly
        530                 535                 540

Ser Gly Pro Gly Gln Gln Gly Pro Tyr Gly Pro Gln Ser Gly Ser
545                 550                 555                 560

Gly Gln Gln Gly Pro Gly Gln Gly Pro Tyr Ala Ser Ala Ala Ala
                565                 570                 575

Ala Ala Gly Pro Gly Ser Gly Gln Gln Gly Pro Gly Ala Ser
            580                 585                 590

<210> SEQ ID NO 5
<211> LENGTH: 12
<212> TYPE: PRT
<213> ORGANISM: Artificial Sequence
<220> FEATURE:
<223> OTHER INFORMATION: HisTag

<400> SEQUENCE: 5

Met His His His His His His Ser Ser Gly Ser Ser
1               5                   10

<210> SEQ ID NO 6
<211> LENGTH: 608
<212> TYPE: PRT
<213> ORGANISM: Artificial Sequence
<220> FEATURE:
<223> OTHER INFORMATION: PRT313

<400> SEQUENCE: 6

Met His His His His His His Ser Ser Gly Ser Ser Gly Pro Gly Gly
1               5                   10                  15

Gln Gly Pro Tyr Gly Pro Gly Ala Ser Ala Ala Ala Ala Gly Gly
            20                  25                  30

Asn Gly Pro Gly Ser Gly Gln Gln Gly Pro Gly Gly Ser Ala Ala Ala
            35                  40                  45

Ala Ala Gly Gly Tyr Gly Pro Gly Gly Gln Gly Pro Gly Gln Gln Gly
        50                  55                  60

Pro Gly Ser Ser Ala Ala Ala Ala Ala Gly Pro Gly Gly Tyr Gly Pro
65                  70                  75                  80

Gly Gly Gln Gly Pro Ser Ala Ser Ala Ala Ala Ala Gly Pro Gly
                85                  90                  95

Ser Gly Gln Gln Gly Pro Gly Ala Ser Ala Ala Ala Ala Gly Gly
            100                 105                 110

Tyr Gly Pro Gly Gly Gln Gly Pro Gly Gln Gln Gly Pro Gly Ser Ser
            115                 120                 125

Ala Ala Ala Ala Ala Gly Gly Tyr Gly Ser Gly Pro Gly Gln Gln Gly
        130                 135                 140

Pro Tyr Gly Ser Ala Ala Ala Ala Gly Pro Gly Ser Gly Tyr
145                 150                 155                 160

Gly Gln Gly Pro Tyr Gly Pro Gly Ala Ser Ala Ala Ala Ala Gly
                165                 170                 175

Pro Gly Gly Tyr Gly Pro Gly Gly Gln Gly Pro Ser Ala Ser Ala Ala
            180                 185                 190

Ala Ala Ala Gly Ser Gly Gln Gln Gly Pro Gly Gly Tyr Gly Pro Tyr
        195                 200                 205
```

```
Ala Ser Ala Ala Ala Ala Gly Gly Tyr Gly Ser Gly Pro Gly Gln
    210                 215                 220

Gln Gly Pro Tyr Gly Pro Gly Gly Ser Ala Ala Ala Ala Gly Ser
225                 230                 235                 240

Gly Gln Gln Gly Pro Gly Gln Gly Pro Tyr Ala Ser Ala Ala Ala
                245                 250                 255

Ala Ala Gly Pro Gly Gly Gln Gly Pro Tyr Gly Pro Gly Ser Ser Ala
            260                 265                 270

Ala Ala Ala Ala Gly Gly Tyr Gly Tyr Gly Pro Gly Gly Gln Gly Pro
        275                 280                 285

Tyr Gly Pro Gly Ala Ser Ala Ala Ala Ala Gly Asn Gly Pro
        290                 295                 300

Gly Ser Gly Gly Tyr Gly Pro Gly Gln Gln Gly Pro Gly Gly Ser Ala
305                 310                 315                 320

Ala Ala Ala Gly Pro Gly Gly Gln Gly Pro Tyr Gly Pro Gly Ala
            325                 330                 335

Ser Ala Ala Ala Ala Gly Gly Tyr Gly Pro Gly Gly Gln Gly Pro
        340                 345                 350

Gly Gly Tyr Gly Pro Gly Ser Ser Ala Ala Ala Ala Gly Pro Gly
        355                 360                 365

Gly Gln Gly Pro Tyr Gly Pro Gly Ser Ser Ala Ala Ala Ala Gly
    370                 375                 380

Gly Tyr Gly Pro Gly Gln Gln Gly Pro Tyr Gly Pro Gly Ser Ala
385                 390                 395                 400

Ala Ala Ala Gly Gly Tyr Gln Gln Gly Pro Gly Gln Gly Pro
            405                 410                 415

Tyr Gly Pro Gly Ala Ser Ala Ala Ala Ala Gly Pro Gly Gly Gln
        420                 425                 430

Gly Pro Tyr Gly Pro Gly Ala Ser Ala Ala Ala Ala Gly Pro Gly
        435                 440                 445

Gly Tyr Gly Pro Gly Gly Gln Gly Pro Ser Ala Ser Ala Ala Ala
    450                 455                 460

Ala Gly Gly Tyr Gly Ser Gly Pro Gly Gly Tyr Gly Pro Tyr Gly Pro
465                 470                 475                 480

Gly Gly Ser Ala Ala Ala Ala Gly Pro Gly Ser Gly Gln Gln Gly
            485                 490                 495

Gln Gly Pro Tyr Gly Pro Gly Ala Ser Ala Ala Ala Ala Gly Gly
            500                 505                 510

Tyr Gly Pro Gly Gln Gln Gly Pro Tyr Gly Pro Gly Ser Ala Ala
        515                 520                 525

Ala Ala Ala Gly Pro Gly Ser Gly Gly Tyr Gly Pro Gly Ala Ser Ala
        530                 535                 540

Ala Ala Ala Gly Gly Asn Gly Pro Gly Ser Gly Gly Tyr Gly Pro
545                 550                 555                 560

Gly Gln Gln Gly Pro Gly Gly Ser Ala Ala Ala Ala Gly Gly Tyr
                565                 570                 575

Gln Gln Gly Pro Gly Gln Gly Pro Tyr Gly Pro Gly Ala Ser Ala
            580                 585                 590

Ala Ala Ala Gly Pro Gly Ser Gly Gln Gln Gly Pro Gly Ala Ser
        595                 600                 605
```

<210> SEQ ID NO 7
<211> LENGTH: 601

<212> TYPE: PRT
<213> ORGANISM: Artificial Sequence
<220> FEATURE:
<223> OTHER INFORMATION: PRT399

<400> SEQUENCE: 7

```
Met His His His His His Ser Ser Gly Ser Gly Pro Gly Gly
1               5                   10                  15

Gln Gly Pro Tyr Gly Pro Gly Ala Ser Ala Ala Ala Ala Gly Gly
            20                  25                  30

Asn Gly Pro Gly Ser Gly Gln Gln Gly Pro Gly Gly Ser Gly Gly Tyr
            35                  40                  45

Gly Pro Gly Gly Gln Gly Pro Gly Gln Gly Pro Gly Ser Ser Ala
    50                  55                  60

Ala Ala Ala Ala Gly Pro Gly Gly Tyr Gly Pro Gly Gln Gly Pro
65                  70                  75                  80

Ser Ala Ser Ala Ala Ala Ala Gly Pro Gly Ser Gly Gln Gln Gly
                85                  90                  95

Pro Gly Ala Ser Gly Gly Tyr Gly Pro Gly Gln Gly Pro Gly Gln
            100                 105                 110

Gln Gly Pro Gly Ser Ser Ala Ala Ala Ala Gly Gly Tyr Gly Ser
            115                 120                 125

Gly Pro Gly Gln Gln Gly Pro Tyr Gly Ser Ala Ala Ala Ala Gly
    130                 135                 140

Pro Gly Ser Gly Gly Tyr Gly Gln Gly Pro Tyr Gly Pro Gly Ala Ser
145                 150                 155                 160

Gly Pro Gly Gly Tyr Gly Pro Gly Gly Gln Pro Ser Ala Ser Ala
            165                 170                 175

Ala Ala Ala Gly Ser Gly Gln Gln Gly Pro Gly Gly Tyr Gly Pro
            180                 185                 190

Tyr Ala Ser Ala Ala Ala Ala Gly Gly Tyr Gly Ser Gly Pro Gly
            195                 200                 205

Gln Gln Gly Pro Tyr Gly Pro Gly Ser Gly Ser Gly Gln Gln Gly
            210                 215                 220

Pro Gly Gln Gln Gly Pro Tyr Gly Ser Ala Ala Ala Ala Gly Pro
225                 230                 235                 240

Gly Gly Gln Gly Pro Tyr Gly Pro Gly Ser Ser Ala Ala Ala Ala
            245                 250                 255

Gly Gly Tyr Gly Tyr Gly Pro Gly Gln Gly Pro Tyr Gly Pro Gly
            260                 265                 270

Ala Ser Gly Gly Asn Gly Pro Gly Ser Gly Gly Tyr Gly Pro Gly Gln
            275                 280                 285

Gln Gly Pro Gly Gly Ser Ala Ala Ala Ala Gly Pro Gly Gly Gln
            290                 295                 300

Gly Pro Tyr Gly Pro Gly Ala Ser Ala Ala Ala Ala Gly Gly Tyr
305                 310                 315                 320

Gly Pro Gly Gly Gln Gly Pro Gly Gly Tyr Gly Pro Gly Ser Ser Gly
            325                 330                 335

Pro Gly Gly Gln Gly Pro Tyr Gly Pro Gly Ser Ser Ala Ala Ala Ala
            340                 345                 350

Ala Gly Gly Tyr Gly Pro Gly Gln Gln Gly Pro Tyr Gly Pro Gly Gly
            355                 360                 365

Ser Ala Ala Ala Ala Ala Gly Gly Tyr Gln Gln Gly Pro Gly Gly Gln
            370                 375                 380
```

Gly Pro Tyr Gly Pro Gly Ala Ser Gly Pro Gly Gln Gly Pro Tyr
385                 390                 395                 400

Gly Pro Gly Ala Ser Ala Ala Ala Ala Gly Pro Gly Gly Tyr Gly
            405                 410                 415

Pro Gly Gly Gln Gly Pro Ser Ala Ser Ala Ala Ala Ala Gly Gly
            420                 425                 430

Tyr Gly Ser Gly Pro Gly Gly Tyr Gly Pro Tyr Gly Pro Gly Ser
            435                 440                 445

Gly Pro Gly Ser Gly Gln Gln Gly Gln Gly Pro Tyr Gly Pro Gly Ala
    450                 455                 460

Ser Ala Ala Ala Ala Gly Gly Tyr Gly Pro Gly Gln Gln Gly Pro
465                 470                 475                 480

Tyr Gly Pro Gly Gly Ser Ala Ala Ala Ala Gly Pro Gly Ser Gly
            485                 490                 495

Gly Tyr Gly Pro Gly Ala Ser Gly Gly Asn Gly Pro Gly Ser Gly
            500                 505                 510

Tyr Gly Pro Gly Gln Gln Gly Pro Gly Gly Ser Ala Ala Ala Ala
            515                 520                 525

Gly Gly Tyr Gln Gln Gly Pro Gly Gln Pro Tyr Gly Pro Gly
            530                 535                 540

Ala Ser Ala Ala Ala Ala Gly Gly Tyr Gly Ser Gly Pro Gly Gln
545                 550                 555                 560

Gln Gly Pro Tyr Gly Pro Gly Ser Gly Ser Gly Gln Gln Gly Pro
            565                 570                 575

Gly Gln Gln Gly Pro Tyr Ala Ser Ala Ala Ala Ala Gly Pro Gly
            580                 585                 590

Ser Gly Gln Gln Gly Pro Gly Ala Ser
            595                 600

<210> SEQ ID NO 8
<211> LENGTH: 608
<212> TYPE: PRT
<213> ORGANISM: Artificial Sequence
<220> FEATURE:
<223> OTHER INFORMATION: PRT380

<400> SEQUENCE: 8

Met His His His His His Ser Ser Gly Ser Ser Gly Pro Gly Gln
1               5                   10                  15

Gln Gly Pro Tyr Gly Pro Gly Ala Ser Ala Ala Ala Ala Gly Gln
            20                  25                  30

Asn Gly Pro Gly Ser Gly Gln Gln Gly Pro Gly Gln Ser Ala Ala
            35                  40                  45

Ala Ala Gly Gln Tyr Gly Pro Gly Gln Gln Gly Pro Gly Gln Gly
    50                  55                  60

Pro Gly Ser Ser Ala Ala Ala Ala Gly Pro Gly Gln Tyr Gly Pro
65                  70                  75                  80

Gly Gln Gln Gly Pro Ser Ala Ser Ala Ala Ala Ala Gly Pro Gly
            85                  90                  95

Ser Gly Gln Gln Gly Pro Gly Ala Ser Ala Ala Ala Ala Gly Gln
            100                 105                 110

Tyr Gly Pro Gly Gln Gln Gly Pro Gly Gln Gln Gly Pro Gly Ser Ser
            115                 120                 125

Ala Ala Ala Ala Ala Gly Gln Tyr Gly Ser Gly Pro Gly Gln Gln Gly
    130                 135                 140

```
Pro Tyr Gly Ser Ala Ala Ala Ala Gly Pro Gly Gln Tyr
145                 150                 155                 160

Gly Gln Gly Pro Tyr Gly Pro Gly Ala Ser Ala Ala Ala Gly
                165                 170                 175

Pro Gly Gln Tyr Gly Pro Gly Gln Gln Gly Pro Ser Ala Ser Ala Ala
            180                 185                 190

Ala Ala Ala Gly Ser Gly Gln Gln Gly Pro Gly Gln Tyr Gly Pro Tyr
        195                 200                 205

Ala Ser Ala Ala Ala Ala Gly Gln Tyr Gly Ser Gly Pro Gly Gln
        210                 215                 220

Gln Gly Pro Tyr Gly Pro Gly Gln Ser Ala Ala Ala Ala Gly Ser
225                 230                 235                 240

Gly Gln Gln Gly Pro Gly Gln Gly Pro Tyr Ala Ser Ala Ala
            245                 250                 255

Ala Ala Gly Pro Gly Gln Gln Gly Pro Tyr Gly Pro Gly Ser Ser Ala
            260                 265                 270

Ala Ala Ala Ala Gly Gln Tyr Gly Tyr Gly Pro Gly Gln Gln Gly Pro
        275                 280                 285

Tyr Gly Pro Gly Ala Ser Ala Ala Ala Ala Gly Gln Asn Gly Pro
290                 295                 300

Gly Ser Gly Gln Tyr Gly Pro Gly Gln Gln Gly Pro Gly Gln Ser Ala
305                 310                 315                 320

Ala Ala Ala Ala Gly Pro Gly Gln Gln Gly Pro Tyr Gly Pro Gly Ala
                325                 330                 335

Ser Ala Ala Ala Ala Gly Gln Tyr Gly Pro Gly Gln Gln Gly Pro
        340                 345                 350

Gly Gln Tyr Gly Pro Gly Ser Ser Ala Ala Ala Ala Gly Pro Gly
            355                 360                 365

Gln Gly Pro Tyr Gly Pro Gly Ser Ser Ala Ala Ala Ala Gly
            370                 375                 380

Gln Tyr Gly Pro Gly Gln Gln Gly Pro Tyr Gly Pro Gly Gln Ser Ala
385                 390                 395                 400

Ala Ala Ala Gly Gln Tyr Gln Gln Gly Pro Gly Gln Gln Gly Pro
            405                 410                 415

Tyr Gly Pro Gly Ala Ser Ala Ala Ala Ala Gly Pro Gly Gln Gln
            420                 425                 430

Gly Pro Tyr Gly Pro Gly Ala Ser Ala Ala Ala Ala Gly Pro Gly
            435                 440                 445

Gln Tyr Gly Pro Gly Gln Gln Gly Pro Ser Ala Ser Ala Ala Ala
    450                 455                 460

Ala Gly Gln Tyr Gly Ser Gly Pro Gly Gln Tyr Gly Pro Tyr Gly Pro
465                 470                 475                 480

Gly Gln Ser Ala Ala Ala Ala Ala Gly Pro Gly Ser Gly Gln Gln Gly
            485                 490                 495

Gln Gly Pro Tyr Gly Pro Gly Ala Ser Ala Ala Ala Ala Gly Gln
            500                 505                 510

Tyr Gly Pro Gly Gln Gln Gly Pro Tyr Gly Pro Gly Gln Ser Ala Ala
            515                 520                 525

Ala Ala Ala Gly Pro Gly Ser Gly Gln Tyr Gly Pro Gly Ala Ser Ala
        530                 535                 540

Ala Ala Ala Gly Gln Asn Gly Pro Gly Ser Gly Gln Tyr Gly Pro
545                 550                 555                 560

Gly Gln Gln Gly Pro Gly Gln Ser Ala Ala Ala Ala Ala Gly Gln Tyr
```

```
                        565                 570                 575
Gln Gln Gly Pro Gly Gln Gln Gly Pro Tyr Gly Pro Gly Ala Ser Ala
                580                 585                 590
Ala Ala Ala Ala Gly Pro Gly Ser Gly Gln Gln Gly Pro Gly Ala Ser
                595                 600                 605

<210> SEQ ID NO 9
<211> LENGTH: 601
<212> TYPE: PRT
<213> ORGANISM: Artificial Sequence
<220> FEATURE:
<223> OTHER INFORMATION: PRT410

<400> SEQUENCE: 9

Met His His His His His Ser Ser Gly Ser Ser Gly Pro Gly Gln
1               5                   10                  15

Gln Gly Pro Tyr Gly Pro Gly Ala Ser Ala Ala Ala Ala Gly Gln
                20                  25                  30

Asn Gly Pro Gly Ser Gly Gln Gln Gly Pro Gly Gln Ser Gly Gln Tyr
                35                  40                  45

Gly Pro Gly Gln Gln Gly Pro Gly Gln Gln Gly Pro Gly Ser Ser Ala
        50                  55                  60

Ala Ala Ala Ala Gly Pro Gly Gln Tyr Gly Pro Gly Gln Gln Gly Pro
65                  70                  75                  80

Ser Ala Ser Ala Ala Ala Ala Gly Pro Gly Ser Gly Gln Gln Gly
                85                  90                  95

Pro Gly Ala Ser Gly Gln Tyr Gly Pro Gly Gln Gln Gly Pro Gly Gln
                100                 105                 110

Gln Gly Pro Gly Ser Ser Ala Ala Ala Ala Gly Gln Tyr Gly Ser
        115                 120                 125

Gly Pro Gly Gln Gln Gly Pro Tyr Gly Ser Ala Ala Ala Ala Gly
        130                 135                 140

Pro Gly Ser Gly Gln Tyr Gly Gln Gly Pro Tyr Gly Pro Gly Ala Ser
145                 150                 155                 160

Gly Pro Gly Gln Tyr Gly Pro Gly Gln Gln Gly Pro Ser Ala Ser Ala
                165                 170                 175

Ala Ala Ala Gly Ser Gly Gln Gln Gly Pro Gly Gln Tyr Gly Pro
        180                 185                 190

Tyr Ala Ser Ala Ala Ala Ala Gly Gln Tyr Gly Ser Gly Pro Gly
        195                 200                 205

Gln Gln Gly Pro Tyr Gly Pro Gly Gln Ser Gly Ser Gly Gln Gln Gly
        210                 215                 220

Pro Gly Gln Gln Gly Pro Tyr Ala Ser Ala Ala Ala Ala Gly Pro
225                 230                 235                 240

Gly Gln Gln Gly Pro Tyr Gly Pro Gly Ser Ser Ala Ala Ala Ala
                245                 250                 255

Gly Gln Tyr Gly Tyr Gly Pro Gly Gln Gly Pro Tyr Gly Pro Gly
        260                 265                 270

Ala Ser Gly Gln Asn Gly Pro Gly Ser Gly Gln Tyr Gly Pro Gly Gln
        275                 280                 285

Gln Gly Pro Gly Ser Ala Ala Ala Ala Gly Pro Gly Gln Gln
        290                 295                 300

Gly Pro Tyr Gly Pro Gly Ala Ser Ala Ala Ala Ala Gly Gln Tyr
305                 310                 315                 320

Gly Pro Gly Gln Gln Gly Pro Gly Gln Tyr Gly Pro Gly Ser Ser Gly
```

-continued

```
                325                 330                 335
Pro Gly Gln Gln Gly Pro Tyr Gly Pro Gly Ser Ser Ala Ala Ala Ala
            340                 345                 350

Ala Gly Gln Tyr Gly Pro Gly Gln Gln Gly Pro Tyr Gly Pro Gly Gln
        355                 360                 365

Ser Ala Ala Ala Ala Gly Gln Tyr Gln Gly Pro Gly Gln Gln
    370                 375                 380

Gly Pro Tyr Gly Pro Gly Ala Ser Gly Pro Gly Gln Gln Gly Pro Tyr
385                 390                 395                 400

Gly Pro Gly Ala Ser Ala Ala Ala Ala Gly Pro Gly Gln Tyr Gly
                405                 410                 415

Pro Gly Gln Gln Gly Pro Ser Ala Ser Ala Ala Ala Ala Gly Gln
            420                 425                 430

Tyr Gly Ser Gly Pro Gly Gln Tyr Gly Pro Tyr Gly Pro Gly Gln Ser
        435                 440                 445

Gly Pro Gly Ser Gly Gln Gln Gly Gln Gly Pro Tyr Gly Pro Gly Ala
    450                 455                 460

Ser Ala Ala Ala Ala Gly Gln Tyr Gly Pro Gly Gln Gln Gly Pro
465                 470                 475                 480

Tyr Gly Pro Gly Gln Ser Ala Ala Ala Ala Gly Pro Gly Ser Gly
                485                 490                 495

Gln Tyr Gly Pro Gly Ala Ser Gly Gln Asn Gly Pro Gly Ser Gly Gln
        500                 505                 510

Tyr Gly Pro Gly Gln Gln Gly Pro Gln Ser Ala Ala Ala Ala
    515                 520                 525

Gly Gln Tyr Gln Gln Gly Pro Gly Gln Gly Pro Tyr Gly Pro Gly
    530                 535                 540

Ala Ser Ala Ala Ala Ala Gly Gln Tyr Gly Ser Gly Pro Gly Gln
545                 550                 555                 560

Gln Gly Pro Tyr Gly Pro Gly Gln Ser Gly Ser Gly Gln Gln Gly Pro
                565                 570                 575

Gly Gln Gln Gly Pro Tyr Ala Ser Ala Ala Ala Ala Gly Pro Gly
            580                 585                 590

Ser Gly Gln Gln Gly Pro Gly Ala Ser
    595                 600
```

<210> SEQ ID NO 10
<211> LENGTH: 565
<212> TYPE: PRT
<213> ORGANISM: Artificial Sequence
<220> FEATURE:
<223> OTHER INFORMATION: Met-PRT468

<400> SEQUENCE: 10

```
Met Gly Pro Gly Gln Gln Gly Pro Tyr Gly Pro Gly Ala Ser Ala Ala
1               5                   10                  15

Ala Ala Ala Ala Gly Ser Asn Gly Pro Gly Ser Gly Gln Gln Gly
            20                  25                  30

Pro Gly Gln Ser Gly Gln Tyr Gly Pro Gly Gln Gln Gly Pro Gly Gln
        35                  40                  45

Gln Gly Pro Gly Ser Ser Ala Ala Ala Ala Ala Gly Pro Gly
    50                  55                  60

Gln Tyr Gly Pro Gly Gln Gln Gly Pro Ser Ala Ser Ala Ala Ala Ala
65                  70                  75                  80

Ala Ala Ala Gly Pro Gly Ser Gly Gln Gln Gly Pro Gly Ala Ser Gly
```

```
                    85                  90                  95
Gln Tyr Gly Pro Gly Gln Gln Gly Pro Gly Gln Gln Gly Pro Gly Ser
                100                 105                 110
Ser Ala Ala Ala Ala Ala Ala Ala Gly Ser Tyr Gly Ser Gly Pro Gly
                115                 120                 125
Gln Gln Gly Pro Tyr Gly Ser Ala Ala Ala Ala Ala Ala Ala Gly Pro
            130                 135                 140
Gly Ser Gly Gln Tyr Gln Gly Pro Tyr Gly Pro Gly Ala Ser Gly
145                 150                 155                 160
Pro Gly Gln Tyr Gly Pro Gly Gln Gln Gly Pro Ser Ala Ser Ala Ala
                165                 170                 175
Ala Ala Ala Ala Ala Gly Ser Gly Gln Gln Gly Pro Gly Gln Tyr Gly
                180                 185                 190
Pro Tyr Ala Ser Ala Ala Ala Ala Ala Ala Gly Ser Tyr Gly Ser
            195                 200                 205
Gly Pro Gly Gln Gln Pro Tyr Gly Pro Gly Gln Ser Gly Ser Gly
        210                 215                 220
Gln Gln Gly Pro Gly Gln Gln Gly Pro Tyr Ala Ser Ala Ala Ala Ala
225                 230                 235                 240
Ala Ala Ala Gly Pro Gly Gln Gln Pro Tyr Gly Pro Gly Ser Ser
            245                 250                 255
Ala Ala Ala Ala Ala Ala Gly Ser Tyr Gly Tyr Gly Pro Gly Gln
        260                 265                 270
Gln Gly Pro Tyr Gly Pro Gly Ala Ser Gly Gln Asn Gly Pro Gly Ser
            275                 280                 285
Gly Gln Tyr Gly Pro Gly Gln Gln Pro Gly Pro Ser Ala Ala Ala
        290                 295                 300
Ala Ala Ala Gly Pro Gly Gln Gln Gly Pro Tyr Gly Pro Gly Ala
305                 310                 315                 320
Ser Ala Ala Ala Ala Ala Ala Gly Ser Tyr Gly Pro Gly Gln Gln
            325                 330                 335
Gly Pro Gly Gln Tyr Gly Pro Gly Ser Ser Gly Pro Gly Gln Gln Gly
        340                 345                 350
Pro Tyr Gly Pro Gly Ser Ser Ala Ala Ala Ala Ala Ala Gly Ser
    355                 360                 365
Tyr Gly Pro Gly Gln Gln Gly Pro Tyr Gly Pro Gly Pro Ser Ala Ala
        370                 375                 380
Ala Ala Ala Ala Ala Gly Ser Tyr Gln Gln Gly Pro Gly Gln Gln Gly
385                 390                 395                 400
Pro Tyr Gly Pro Gly Ala Ser Gly Pro Gly Gln Gln Gly Pro Tyr Gly
            405                 410                 415
Pro Gly Ala Ser Ala Ala Ala Ala Ala Ala Gly Pro Gly Gln Tyr
        420                 425                 430
Gly Pro Gly Gln Gln Gly Pro Ser Ala Ser Ala Ala Ala Ala Ala
    435                 440                 445
Ala Gly Ser Tyr Gly Ser Gly Pro Gly Gln Tyr Gly Pro Tyr Gly Pro
    450                 455                 460
Gly Gln Ser Gly Pro Gly Ser Gly Gln Gln Gly Pro Tyr Gly
465                 470                 475                 480
Pro Gly Ala Ser Ala Ala Ala Ala Ala Ala Gly Ser Tyr Gly Pro
        485                 490                 495
Gly Gln Gln Gly Pro Tyr Gly Pro Gly Pro Ser Ala Ala Ala Ala Ala
        500                 505                 510
```

Ala Ala Gly Pro Gly Ser Gly Gln Tyr Gly Pro Gly Ala Ser Gly Gln
            515                 520                 525

Asn Gly Pro Gly Ser Gly Gln Tyr Gly Pro Gly Gln Gln Gly Pro Gly
            530                 535                 540

Pro Ser Ala Ala Ala Ala Ala Ala Gly Pro Gly Ser Gly Gln Gln
545                 550                 555                 560

Gly Pro Gly Ala Ser
            565

<210> SEQ ID NO 11
<211> LENGTH: 576
<212> TYPE: PRT
<213> ORGANISM: Artificial Sequence
<220> FEATURE:
<223> OTHER INFORMATION: PRT468

<400> SEQUENCE: 11

Met His His His His His Ser Ser Gly Ser Gly Pro Gly Gln
1               5                   10                  15

Gln Gly Pro Tyr Gly Pro Gly Ala Ser Ala Ala Ala Ala Ala Ala
                20                  25                  30

Gly Ser Asn Gly Pro Gly Ser Gly Gln Gln Gly Pro Gly Gln Ser Gly
            35                  40                  45

Gln Tyr Gly Pro Gly Gln Gln Gly Pro Gly Gln Gln Gly Pro Gly Ser
    50                  55                  60

Ser Ala Ala Ala Ala Ala Ala Ala Gly Pro Gly Gln Tyr Gly Pro Gly
65                  70                  75                  80

Gln Gln Gly Pro Ser Ala Ser Ala Ala Ala Ala Ala Ala Gly Pro
                85                  90                  95

Gly Ser Gly Gln Gln Gly Pro Gly Ala Ser Gly Gln Tyr Gly Pro Gly
            100                 105                 110

Gln Gln Gly Pro Gly Gln Gln Gly Pro Gly Ser Ser Ala Ala Ala Ala
            115                 120                 125

Ala Ala Ala Gly Ser Tyr Gly Ser Gly Pro Gly Gln Gln Gly Pro Tyr
    130                 135                 140

Gly Ser Ala Ala Ala Ala Ala Ala Gly Pro Gly Ser Gly Gln Tyr
145                 150                 155                 160

Gly Gln Gly Pro Tyr Gly Pro Gly Ala Ser Gly Pro Gly Gln Tyr Gly
                165                 170                 175

Pro Gly Gln Gln Gly Pro Ser Ala Ser Ala Ala Ala Ala Ala Ala
                180                 185                 190

Gly Ser Gly Gln Gln Gly Pro Gly Gln Tyr Gly Pro Tyr Ala Ser Ala
        195                 200                 205

Ala Ala Ala Ala Ala Gly Ser Tyr Gly Ser Gly Pro Gly Gln Gln
    210                 215                 220

Gly Pro Tyr Gly Pro Gly Gln Ser Gly Ser Gly Gln Gln Gly Pro Gly
225                 230                 235                 240

Gln Gln Gly Pro Tyr Gly Ser Ala Ala Ala Ala Ala Ala Gly Pro
                245                 250                 255

Gly Gln Gln Gly Pro Tyr Gly Pro Gly Ser Ser Ala Ala Ala Ala
            260                 265                 270

Ala Ala Gly Ser Tyr Gly Tyr Gly Pro Gly Gln Gln Gly Pro Tyr Gly
    275                 280                 285

Pro Gly Ala Ser Gly Gln Asn Gly Pro Gly Ser Gly Gln Tyr Gly Pro
    290                 295                 300

Gly Gln Gln Gly Pro Gly Pro Ser Ala Ala Ala Ala Ala Gly
305                 310                 315                 320

Pro Gly Gln Gln Gly Pro Tyr Gly Pro Gly Ala Ser Ala Ala Ala
            325                 330                 335

Ala Ala Ala Gly Ser Tyr Gly Pro Gly Gln Gln Gly Pro Gly Gln Tyr
            340                 345                 350

Gly Pro Gly Ser Ser Gly Pro Gly Gln Gln Gly Pro Tyr Gly Pro Gly
        355                 360                 365

Ser Ser Ala Ala Ala Ala Ala Ala Gly Ser Tyr Gly Pro Gly Gln
    370                 375                 380

Gln Gly Pro Tyr Gly Pro Gly Pro Ser Ala Ala Ala Ala Ala Ala
385                 390                 395                 400

Gly Ser Tyr Gln Gln Gly Pro Gly Gln Gln Gly Pro Tyr Gly Pro Gly
            405                 410                 415

Ala Ser Gly Pro Gly Gln Gln Gly Pro Tyr Gly Pro Gly Ala Ser Ala
            420                 425                 430

Ala Ala Ala Ala Ala Gly Pro Gly Gln Tyr Gly Pro Gly Gln Gln
    435                 440                 445

Gly Pro Ser Ala Ser Ala Ala Ala Ala Ala Gly Ser Tyr Gly
    450                 455                 460

Ser Gly Pro Gly Gln Tyr Gly Pro Tyr Gly Pro Gly Gln Ser Gly Pro
465                 470                 475                 480

Gly Ser Gly Gln Gln Gly Gln Gly Pro Tyr Gly Pro Gly Ala Ser Ala
            485                 490                 495

Ala Ala Ala Ala Ala Gly Ser Tyr Gly Pro Gly Gln Gln Gly Pro
            500                 505                 510

Tyr Gly Pro Gly Pro Ser Ala Ala Ala Ala Ala Ala Gly Pro Gly
            515                 520                 525

Ser Gly Gln Tyr Gly Pro Gly Ala Ser Gly Gln Asn Gly Pro Gly Ser
            530                 535                 540

Gly Gln Tyr Gly Pro Gly Gln Gln Gly Pro Gly Pro Ser Ala Ala Ala
545                 550                 555                 560

Ala Ala Ala Ala Gly Pro Gly Ser Gly Gln Gln Gly Pro Gly Ala Ser
            565                 570                 575

<210> SEQ ID NO 12
<211> LENGTH: 2364
<212> TYPE: PRT
<213> ORGANISM: Artificial Sequence
<220> FEATURE:
<223> OTHER INFORMATION: Met-PRT799

<400> SEQUENCE: 12

Met Gly Pro Gly Gln Gln Gly Pro Tyr Gly Pro Gly Ala Ser Ala Ala
1               5                   10                  15

Ala Ala Ala Gly Gln Asn Gly Pro Gly Ser Gln Gln Gly Pro Gly
            20                  25                  30

Gln Ser Gly Gln Tyr Gly Pro Gly Gln Gln Gly Pro Gly Gln Gln Gly
        35                  40                  45

Pro Gly Ser Ser Ala Ala Ala Ala Ala Gly Pro Gly Gln Tyr Gly Pro
    50                  55                  60

Gly Gln Gln Gly Pro Ser Ala Ser Ala Ala Ala Ala Gly Pro Gly
65                  70                  75                  80

Ser Gly Gln Gln Gly Pro Gly Ala Ser Gly Gln Tyr Gly Pro Gly Gln
            85                  90                  95

```
Gln Gly Pro Gly Gln Gly Pro Gly Ser Ala Ala Ala Ala
            100             105             110

Gly Gln Tyr Gly Ser Gly Pro Gly Gln Gln Gly Pro Tyr Gly Ser Ala
            115             120             125

Ala Ala Ala Ala Gly Pro Gly Ser Gly Gln Tyr Gly Gln Gly Pro Tyr
            130             135             140

Gly Pro Gly Ala Ser Gly Pro Gly Gln Tyr Gly Pro Gly Gln Gln Gly
145             150             155             160

Pro Ser Ala Ser Ala Ala Ala Ala Gly Ser Gln Gln Gly Pro
                165             170             175

Gly Gln Tyr Gly Pro Tyr Ala Ser Ala Ala Ala Ala Gly Gln Tyr
            180             185             190

Gly Ser Gly Pro Gly Gln Gln Gly Pro Tyr Gly Pro Gly Gln Ser Gly
            195             200             205

Ser Gly Gln Gln Gly Pro Gly Gln Gln Gly Pro Tyr Ala Ser Ala Ala
    210             215             220

Ala Ala Ala Gly Pro Gly Gln Gln Gly Pro Tyr Gly Pro Gly Ser Ser
225             230             235             240

Ala Ala Ala Ala Ala Gly Gln Tyr Gly Tyr Gly Pro Gly Gln Gln Gly
            245             250             255

Pro Tyr Gly Pro Gly Ala Ser Gly Gln Asn Gly Pro Gly Ser Gly Gln
            260             265             270

Tyr Gly Pro Gly Gln Gln Gly Pro Gly Gln Ser Ala Ala Ala Ala Ala
            275             280             285

Gly Pro Gly Gln Gln Gly Pro Tyr Gly Pro Gly Ala Ser Ala Ala Ala
            290             295             300

Ala Ala Gly Gln Tyr Gly Pro Gly Gln Gln Gly Pro Gly Gln Tyr Gly
305             310             315             320

Pro Gly Ser Ser Gly Pro Gly Gln Gln Gly Pro Tyr Gly Pro Gly Ser
            325             330             335

Ser Ala Ala Ala Ala Ala Gly Gln Tyr Gly Pro Gly Gln Gln Gly Pro
            340             345             350

Tyr Gly Pro Gly Gln Ser Ala Ala Ala Ala Gly Gln Tyr Gln Gln
            355             360             365

Gly Pro Gly Gln Gln Gly Pro Tyr Gly Pro Gly Ala Ser Gly Pro Gly
            370             375             380

Gln Gln Gly Pro Tyr Gly Pro Gly Ala Ser Ala Ala Ala Ala Gly
385             390             395             400

Pro Gly Gln Tyr Gly Pro Gly Gln Gly Pro Ser Ala Ser Ala Ala
            405             410             415

Ala Ala Ala Gly Gln Tyr Gly Ser Gly Pro Gly Gln Tyr Gly Pro Tyr
            420             425             430

Gly Pro Gly Gln Ser Gly Pro Gly Ser Gly Gln Gln Gly Gln Gly Pro
            435             440             445

Tyr Gly Pro Gly Ala Ser Ala Ala Ala Ala Gly Gln Tyr Gly Pro
            450             455             460

Gly Gln Gln Gly Pro Tyr Gly Pro Gly Ser Ala Ala Ala Ala Ala
465             470             475             480

Gly Pro Gly Ser Gly Gln Tyr Gly Pro Gly Ala Ser Gly Gln Asn Gly
            485             490             495

Pro Gly Ser Gly Gln Tyr Gly Pro Gly Gln Gln Gly Pro Gly Gln Ser
            500             505             510
```

Ala Ala Ala Ala Gly Gln Tyr Gln Gln Gly Pro Gly Gln Gln Gly
            515                 520                 525

Pro Tyr Gly Pro Gly Ala Ser Ala Ala Ala Ala Gly Gln Tyr Gly
    530                 535                 540

Ser Gly Pro Gly Gln Gln Gly Pro Tyr Gly Pro Gly Gln Ser Gly Ser
545                 550                 555                 560

Gly Gln Gln Gly Pro Gly Gln Gln Gly Pro Tyr Ala Ser Ala Ala Ala
                565                 570                 575

Ala Ala Gly Pro Gly Ser Gly Gln Gln Gly Pro Gly Ala Ser Gly Gln
            580                 585                 590

Gln Gly Pro Tyr Gly Pro Gly Ala Ser Ala Ala Ala Ala Gly Gln
        595                 600                 605

Asn Gly Pro Gly Ser Gly Gln Gln Gly Pro Gly Gln Ser Gly Gln Tyr
    610                 615                 620

Gly Pro Gly Gln Gln Gly Pro Gly Gln Gln Gly Pro Gly Ser Ser Ala
625                 630                 635                 640

Ala Ala Ala Ala Gly Pro Gly Gln Tyr Gly Pro Gly Gln Gln Gly Pro
            645                 650                 655

Ser Ala Ser Ala Ala Ala Ala Gly Pro Gly Ser Gly Gln Gln Gly
    660                 665                 670

Pro Gly Ala Ser Gly Gln Tyr Gly Pro Gly Gln Gln Gly Pro Gly Gln
            675                 680                 685

Gln Gly Pro Gly Ser Ser Ala Ala Ala Ala Gly Gln Tyr Gly Ser
    690                 695                 700

Gly Pro Gly Gln Gln Gly Pro Tyr Gly Ser Ala Ala Ala Ala Gly
705                 710                 715                 720

Pro Gly Ser Gly Gln Tyr Gly Gln Gly Pro Tyr Gly Pro Gly Ala Ser
            725                 730                 735

Gly Pro Gly Gln Tyr Gly Pro Gly Gln Gln Gly Pro Ser Ala Ser Ala
                740                 745                 750

Ala Ala Ala Gly Ser Gly Gln Gln Gly Pro Gly Gln Tyr Gly Pro
            755                 760                 765

Tyr Ala Ser Ala Ala Ala Ala Gly Gln Tyr Gly Ser Gly Pro Gly
    770                 775                 780

Gln Gln Gly Pro Tyr Gly Pro Gly Gln Ser Gly Ser Gly Gln Gln Gly
785                 790                 795                 800

Pro Gly Gln Gln Gly Pro Tyr Ala Ser Ala Ala Ala Ala Gly Pro
            805                 810                 815

Gly Gln Gln Gly Pro Tyr Gly Pro Gly Ser Ser Ala Ala Ala Ala
    820                 825                 830

Gly Gln Tyr Gly Tyr Gly Pro Gly Gln Gln Gly Pro Tyr Gly Pro Gly
                835                 840                 845

Ala Ser Gly Gln Asn Gly Pro Gly Ser Gly Gln Tyr Gly Pro Gly Gln
850                 855                 860

Gln Gly Pro Gly Gln Ser Ala Ala Ala Ala Gly Pro Gly Gln Gln
865                 870                 875                 880

Gly Pro Tyr Gly Pro Gly Ala Ser Ala Ala Ala Ala Gly Gln Tyr
            885                 890                 895

Gly Pro Gly Gln Gln Gly Pro Gly Gln Tyr Gly Pro Gly Ser Ser Gly
        900                 905                 910

Pro Gly Gln Gln Gly Pro Tyr Gly Pro Gly Ser Ser Ala Ala Ala Ala
            915                 920                 925

Ala Gly Gln Tyr Gly Pro Gly Gln Gln Gly Pro Tyr Gly Pro Gly Gln

-continued

```
                930             935             940
Ser Ala Ala Ala Ala Gly Gln Tyr Gln Gln Gly Pro Gly Gln Gln
945                 950             955             960

Gly Pro Tyr Gly Pro Gly Ala Ser Gly Pro Gly Gln Gln Pro Tyr
                965             970             975

Gly Pro Gly Ala Ser Ala Ala Ala Ala Gly Pro Gly Gln Tyr Gly
            980             985             990

Pro Gly Gln Gln Gly Pro Ser Ala Ser Ala Ala Ala Ala Gly Gln
        995             1000            1005

Tyr Gly Ser Gly Pro Gly Gln Tyr Gly Pro Tyr Gly Pro Gly Gln
    1010            1015            1020

Ser Gly Pro Gly Ser Gly Gln Gln Gly Gln Gly Pro Tyr Gly Pro
    1025            1030            1035

Gly Ala Ser Ala Ala Ala Ala Gly Gln Tyr Gly Pro Gly Gln
    1040            1045            1050

Gln Gly Pro Tyr Gly Pro Gly Gln Ser Ala Ala Ala Ala Ala Gly
    1055            1060            1065

Pro Gly Ser Gly Gln Tyr Gly Pro Gly Ala Ser Gly Gln Asn Gly
    1070            1075            1080

Pro Gly Ser Gly Gln Tyr Gly Pro Gly Gln Gln Gly Pro Gly Gln
    1085            1090            1095

Ser Ala Ala Ala Ala Gly Gln Tyr Gln Gln Gly Pro Gly Gln
    1100            1105            1110

Gln Gly Pro Tyr Gly Pro Gly Ala Ser Ala Ala Ala Ala Ala Gly
    1115            1120            1125

Gln Tyr Gly Ser Gly Pro Gly Gln Gln Gly Pro Tyr Gly Pro Gly
    1130            1135            1140

Gln Ser Gly Ser Gly Gln Gln Gly Pro Gln Gln Gly Pro Tyr
    1145            1150            1155

Ala Ser Ala Ala Ala Ala Ala Gly Pro Gly Ser Gly Gln Gln Gly
    1160            1165            1170

Pro Gly Ala Ser Gly Gln Gln Gly Pro Tyr Gly Pro Gly Ala Ser
    1175            1180            1185

Ala Ala Ala Ala Gly Gln Asn Gly Pro Gly Ser Gly Gln Gln
    1190            1195            1200

Gly Pro Gly Gln Ser Gly Gln Tyr Gly Pro Gly Gln Gln Gly Pro
    1205            1210            1215

Gly Gln Gln Gly Pro Gly Ser Ser Ala Ala Ala Ala Gly Pro
    1220            1225            1230

Gly Gln Tyr Gly Pro Gly Gln Gln Gly Pro Ser Ala Ser Ala Ala
    1235            1240            1245

Ala Ala Ala Gly Pro Gly Ser Gly Gln Gln Gly Pro Gly Ala Ser
    1250            1255            1260

Gly Gln Tyr Gly Pro Gly Gln Gln Gly Pro Gly Gln Gln Gly Pro
    1265            1270            1275

Gly Ser Ser Ala Ala Ala Ala Gly Gln Tyr Gly Ser Gly Pro
    1280            1285            1290

Gly Gln Gln Gly Pro Tyr Gly Ser Ala Ala Ala Ala Gly Pro
    1295            1300            1305

Gly Ser Gly Gln Tyr Gly Gly Pro Tyr Gly Pro Gly Ala Ser
    1310            1315            1320

Gly Pro Gly Gln Tyr Gly Pro Gly Gln Gln Gly Pro Ser Ala Ser
    1325            1330            1335
```

```
Ala Ala Ala Ala Ala Gly Ser Gly Gln Gln Gly Pro Gly Gln Tyr
1340                1345                1350
Gly Pro Tyr Ala Ser Ala Ala Ala Ala Gly Gln Tyr Gly Ser
1355                1360                1365
Gly Pro Gly Gln Gln Gly Pro Tyr Gly Pro Gly Gln Ser Gly Ser
1370                1375                1380
Gly Gln Gln Gly Pro Gly Gln Gln Gly Pro Tyr Ala Ser Ala Ala
1385                1390                1395
Ala Ala Ala Gly Pro Gly Gln Gln Gly Pro Tyr Gly Pro Gly Ser
1400                1405                1410
Ser Ala Ala Ala Ala Gly Gln Tyr Gly Tyr Gly Pro Gly Gln
1415                1420                1425
Gln Gly Pro Tyr Gly Pro Gly Ala Ser Gly Gln Asn Gly Pro Gly
1430                1435                1440
Ser Gly Gln Tyr Gly Pro Gly Gln Gln Gly Pro Gly Gln Ser Ala
1445                1450                1455
Ala Ala Ala Ala Gly Pro Gly Gln Gln Gly Pro Tyr Gly Pro Gly
1460                1465                1470
Ala Ser Ala Ala Ala Ala Ala Gly Gln Tyr Gly Pro Gly Gln Gln
1475                1480                1485
Gly Pro Gly Gln Tyr Gly Pro Gly Ser Ser Gly Pro Gly Gln Gln
1490                1495                1500
Gly Pro Tyr Gly Pro Gly Ser Ser Ala Ala Ala Ala Gly Gln
1505                1510                1515
Tyr Gly Pro Gly Gln Gln Gly Pro Tyr Gly Pro Gly Gln Ser Ala
1520                1525                1530
Ala Ala Ala Gly Gln Tyr Gln Gln Gly Pro Gly Gln Gln Gly
1535                1540                1545
Pro Tyr Gly Pro Gly Ala Ser Gly Pro Gly Gln Gln Gly Pro Tyr
1550                1555                1560
Gly Pro Gly Ala Ser Ala Ala Ala Ala Gly Pro Gly Gln Tyr
1565                1570                1575
Gly Pro Gly Gln Gln Gly Pro Ser Ala Ser Ala Ala Ala Ala Ala
1580                1585                1590
Gly Gln Tyr Gly Ser Gly Pro Gly Gln Tyr Gly Pro Tyr Gly Pro
1595                1600                1605
Gly Gln Ser Gly Pro Gly Ser Gly Gln Gln Gly Gln Gly Pro Tyr
1610                1615                1620
Gly Pro Gly Ala Ser Ala Ala Ala Ala Gly Gln Tyr Gly Pro
1625                1630                1635
Gly Gln Gln Gly Pro Tyr Gly Pro Gly Gln Ser Ala Ala Ala Ala
1640                1645                1650
Ala Gly Pro Gly Ser Gly Gln Tyr Gly Pro Gly Ala Ser Gly Gln
1655                1660                1665
Asn Gly Pro Gly Ser Gly Gln Tyr Gly Pro Gly Gln Gln Gly Pro
1670                1675                1680
Gly Gln Ser Ala Ala Ala Ala Gly Gln Tyr Gln Gln Gly Pro
1685                1690                1695
Gly Gln Gln Gly Pro Tyr Gly Pro Gly Ala Ser Ala Ala Ala Ala
1700                1705                1710
Ala Gly Gln Tyr Gly Ser Gly Pro Gly Gln Gln Gly Pro Tyr Gly
1715                1720                1725
```

```
Pro Gly Gln Ser Gly Ser Gly Gln Gln Gly Pro Gly Gln Gln Gly
1730                1735                1740

Pro Tyr Ala Ser Ala Ala Ala Ala Gly Pro Gly Ser Gly Gln
1745                1750                1755

Gln Gly Pro Gly Ala Ser Gly Gln Gln Gly Pro Tyr Gly Pro Gly
1760                1765                1770

Ala Ser Ala Ala Ala Ala Ala Gly Gln Asn Gly Pro Gly Ser Gly
1775                1780                1785

Gln Gln Gly Pro Gly Gln Ser Gly Gln Tyr Gly Pro Gly Gln Gln
1790                1795                1800

Gly Pro Gly Gln Gln Gly Pro Gly Ser Ser Ala Ala Ala Ala Ala
1805                1810                1815

Gly Pro Gly Gln Tyr Gly Pro Gly Gln Gln Gly Pro Ser Ala Ser
1820                1825                1830

Ala Ala Ala Ala Ala Gly Pro Gly Ser Gly Gln Gln Gly Pro Gly
1835                1840                1845

Ala Ser Gly Gln Tyr Gly Pro Gly Gln Gln Gly Pro Gly Gln Gln
1850                1855                1860

Gly Pro Gly Ser Ser Ala Ala Ala Ala Ala Gly Gln Tyr Gly Ser
1865                1870                1875

Gly Pro Gly Gln Gln Gly Pro Tyr Gly Ser Ala Ala Ala Ala Ala
1880                1885                1890

Gly Pro Gly Ser Gly Gln Tyr Gly Gln Gly Pro Tyr Gly Pro Gly
1895                1900                1905

Ala Ser Gly Pro Gly Gln Tyr Gly Pro Gly Gln Gln Gly Pro Ser
1910                1915                1920

Ala Ser Ala Ala Ala Ala Ala Gly Ser Gly Gln Gln Gly Pro Gly
1925                1930                1935

Gln Tyr Gly Pro Tyr Ala Ser Ala Ala Ala Ala Ala Gly Gln Tyr
1940                1945                1950

Gly Ser Gly Pro Gly Gln Gln Gly Pro Tyr Gly Pro Gly Gln Ser
1955                1960                1965

Gly Ser Gly Gln Gln Gly Pro Gly Gln Gln Gly Pro Tyr Ala Ser
1970                1975                1980

Ala Ala Ala Ala Ala Gly Pro Gly Gln Gln Gly Pro Tyr Gly Pro
1985                1990                1995

Gly Ser Ser Ala Ala Ala Ala Ala Gly Gln Tyr Gly Tyr Gly Pro
2000                2005                2010

Gly Gln Gln Gly Pro Tyr Gly Pro Gly Ala Ser Gly Gln Asn Gly
2015                2020                2025

Pro Gly Ser Gly Gln Tyr Gly Pro Gly Gln Gln Gly Pro Gly Gln
2030                2035                2040

Ser Ala Ala Ala Ala Ala Gly Pro Gly Gln Gln Gly Pro Tyr Gly
2045                2050                2055

Pro Gly Ala Ser Ala Ala Ala Ala Ala Gly Gln Tyr Gly Pro Gly
2060                2065                2070

Gln Gln Gly Pro Gly Gln Tyr Gly Pro Gly Ser Ser Gly Pro Gly
2075                2080                2085

Gln Gln Gly Pro Tyr Gly Pro Gly Ser Ser Ala Ala Ala Ala Ala
2090                2095                2100

Gly Gln Tyr Gly Pro Gly Gln Gln Gly Pro Tyr Gly Pro Gly Gln
2105                2110                2115

Ser Ala Ala Ala Ala Ala Gly Gln Tyr Gln Gln Gly Pro Gly Gln
```

```
                        2120                2125                2130

Gln Gly Pro Tyr Gly Pro Gly Ala Ser Gly Pro Gly Gln Gln Gly
    2135                2140                2145

Pro Tyr Gly Pro Gly Ala Ser Ala Ala Ala Ala Gly Pro Gly
    2150                2155                2160

Gln Tyr Gly Pro Gly Gln Gln Gly Pro Ser Ala Ser Ala Ala Ala
    2165                2170                2175

Ala Ala Gly Gln Tyr Gly Ser Gly Pro Gly Gln Tyr Gly Pro Tyr
    2180                2185                2190

Gly Pro Gly Gln Ser Gly Pro Gly Ser Gly Gln Gln Gly Gln Gly
    2195                2200                2205

Pro Tyr Gly Pro Gly Ala Ser Ala Ala Ala Ala Gly Gln Tyr
    2210                2215                2220

Gly Pro Gly Gln Gln Gly Pro Tyr Gly Pro Gly Gln Ser Ala Ala
    2225                2230                2235

Ala Ala Ala Gly Pro Gly Ser Gly Gln Tyr Gly Pro Gly Ala Ser
    2240                2245                2250

Gly Gln Asn Gly Pro Gly Ser Gly Gln Tyr Gly Pro Gly Gln Gln
    2255                2260                2265

Gly Pro Gly Gln Ser Ala Ala Ala Ala Ala Gly Gln Tyr Gln Gln
    2270                2275                2280

Gly Pro Gly Gln Gln Gly Pro Tyr Gly Pro Gly Ala Ser Ala Ala
    2285                2290                2295

Ala Ala Ala Gly Gln Tyr Gly Ser Gly Pro Gly Gln Gln Gly Pro
    2300                2305                2310

Tyr Gly Pro Gly Gln Ser Gly Ser Gly Gln Gln Gly Pro Gly Gln
    2315                2320                2325

Gln Gly Pro Tyr Ala Ser Ala Ala Ala Ala Gly Pro Gly Ser
    2330                2335                2340

Gly Gln Gln Gly Ser Ser Val Asp Lys Leu Ala Ala Ala Leu Glu
    2345                2350                2355

His His His His His His
    2360

<210> SEQ ID NO 13
<211> LENGTH: 2375
<212> TYPE: PRT
<213> ORGANISM: Artificial Sequence
<220> FEATURE:
<223> OTHER INFORMATION: PRT799

<400> SEQUENCE: 13

Met His His His His His His Ser Ser Gly Ser Ser Gly Pro Gly Gln
1               5                   10                  15

Gln Gly Pro Tyr Gly Pro Gly Ala Ser Ala Ala Ala Ala Gly Gln
            20                  25                  30

Asn Gly Pro Gly Ser Gly Gln Gln Gly Pro Gly Gln Ser Gly Gln Tyr
        35                  40                  45

Gly Pro Gly Gln Gln Gly Pro Gly Gln Gln Gly Pro Gly Ser Ser Ala
    50                  55                  60

Ala Ala Ala Gly Pro Gly Gln Tyr Gly Pro Gly Gln Gln Gly Pro
65                  70                  75                  80

Ser Ala Ser Ala Ala Ala Ala Gly Pro Gly Ser Gly Gln Gln Gly
                85                  90                  95

Pro Gly Ala Ser Gly Gln Tyr Gly Pro Gly Gln Gln Gly Pro Gly Gln
```

```
                100                 105                 110
Gln Gly Pro Gly Ser Ser Ala Ala Ala Ala Gly Gln Tyr Gly Ser
            115                 120                 125
Gly Pro Gly Gln Gln Gly Pro Tyr Gly Ser Ala Ala Ala Ala Gly
            130                 135                 140
Pro Gly Ser Gly Gln Tyr Gly Gln Gly Pro Tyr Gly Pro Gly Ala Ser
145                 150                 155                 160
Gly Pro Gly Gln Tyr Gly Pro Gly Gln Gln Gly Pro Ser Ala Ser Ala
            165                 170                 175
Ala Ala Ala Ala Gly Ser Gly Gln Gln Gly Pro Gly Gln Tyr Gly Pro
            180                 185                 190
Tyr Ala Ser Ala Ala Ala Ala Gly Gln Tyr Gly Ser Gly Pro Gly
            195                 200                 205
Gln Gln Gly Pro Tyr Gly Pro Gly Gln Ser Gly Ser Gly Gln Gln Gly
            210                 215                 220
Pro Gly Gln Gln Gly Pro Tyr Ala Ser Ala Ala Ala Ala Gly Pro
225                 230                 235                 240
Gly Gln Gln Gly Pro Tyr Gly Pro Gly Ser Ser Ala Ala Ala Ala
            245                 250                 255
Gly Gln Tyr Gly Tyr Gly Pro Gly Gln Gln Gly Pro Tyr Gly Pro Gly
            260                 265                 270
Ala Ser Gly Gln Asn Gly Pro Gly Ser Gly Gln Tyr Gly Pro Gly Gln
            275                 280                 285
Gln Gly Pro Gly Gln Ser Ala Ala Ala Ala Gly Pro Gly Gln Gln
            290                 295                 300
Gly Pro Tyr Gly Pro Gly Ala Ser Ala Ala Ala Ala Gly Gln Tyr
305                 310                 315                 320
Gly Pro Gly Gln Gln Gly Pro Gly Gln Tyr Gly Pro Gly Ser Ser Gly
            325                 330                 335
Pro Gly Gln Gln Gly Pro Tyr Gly Pro Gly Ser Ser Ala Ala Ala Ala
            340                 345                 350
Ala Gly Gln Tyr Gly Pro Gly Gln Gln Gly Pro Tyr Gly Pro Gly Gln
            355                 360                 365
Ser Ala Ala Ala Ala Gly Gln Tyr Gln Gln Gly Pro Gly Gln Gln
            370                 375                 380
Gly Pro Tyr Gly Pro Gly Ala Ser Gly Pro Gly Gln Gln Gly Pro Tyr
385                 390                 395                 400
Gly Pro Gly Ala Ser Ala Ala Ala Ala Gly Pro Gly Gln Tyr Gly
            405                 410                 415
Pro Gly Gln Gln Gly Pro Ser Ala Ser Ala Ala Ala Ala Gly Gln
            420                 425                 430
Tyr Gly Ser Gly Pro Gly Gln Tyr Gly Pro Tyr Gly Pro Gly Gln Ser
            435                 440                 445
Gly Pro Gly Ser Gly Gln Gln Gly Gln Gly Pro Tyr Gly Pro Gly Ala
            450                 455                 460
Ser Ala Ala Ala Ala Ala Gly Gln Tyr Gly Pro Gly Gln Gln Gly Pro
465                 470                 475                 480
Tyr Gly Pro Gly Gln Ser Ala Ala Ala Ala Gly Pro Gly Ser Gly
            485                 490                 495
Gln Tyr Gly Pro Gly Ala Ser Gly Gln Asn Gly Pro Gly Ser Gly Gln
            500                 505                 510
Tyr Gly Pro Gly Gln Gln Gly Pro Gly Gln Ser Ala Ala Ala Ala Ala
            515                 520                 525
```

-continued

Gly Gln Tyr Gln Gln Gly Pro Gly Gln Gln Gly Pro Tyr Gly Pro Gly
            530                 535                 540

Ala Ser Ala Ala Ala Ala Gly Gln Tyr Gly Ser Gly Pro Gly Gln
545                 550                 555                 560

Gln Gly Pro Tyr Gly Pro Gly Gln Ser Gly Ser Gly Gln Gln Gly Pro
                565                 570                 575

Gly Gln Gln Gly Pro Tyr Ala Ser Ala Ala Ala Ala Gly Pro Gly
            580                 585                 590

Ser Gly Gln Gln Gly Pro Gly Ala Ser Gly Gln Gln Gly Pro Tyr Gly
            595                 600                 605

Pro Gly Ala Ser Ala Ala Ala Ala Gly Gln Asn Gly Pro Gly Ser
610                 615                 620

Gly Gln Gln Gly Pro Gly Gln Ser Gly Gln Tyr Gly Pro Gly Gln Gln
625                 630                 635                 640

Gly Pro Gly Gln Gln Gly Pro Gly Ser Ser Ala Ala Ala Ala Gly
                645                 650                 655

Pro Gly Gln Tyr Gly Pro Gly Gln Gln Gly Pro Ser Ala Ser Ala Ala
            660                 665                 670

Ala Ala Ala Gly Pro Gly Ser Gly Gln Gln Gly Pro Gly Ala Ser Gly
            675                 680                 685

Gln Tyr Gly Pro Gly Gln Gln Gly Pro Gly Gln Gln Gly Pro Gly Ser
690                 695                 700

Ser Ala Ala Ala Ala Gly Gln Tyr Gly Ser Gly Pro Gly Gln Gln
705                 710                 715                 720

Gly Pro Tyr Gly Ser Ala Ala Ala Ala Gly Pro Gly Ser Gly Gln
                725                 730                 735

Tyr Gly Gln Gly Pro Tyr Gly Pro Gly Ala Ser Gly Pro Gly Gln Tyr
            740                 745                 750

Gly Pro Gly Gln Gln Gly Pro Ser Ala Ser Ala Ala Ala Ala Gly
            755                 760                 765

Ser Gly Gln Gln Gly Pro Gly Gln Tyr Gly Pro Tyr Ala Ser Ala Ala
770                 775                 780

Ala Ala Ala Gly Gln Tyr Gly Ser Gly Pro Gly Gln Gln Gly Pro Tyr
785                 790                 795                 800

Gly Pro Gly Gln Ser Gly Ser Gly Gln Gln Gly Pro Gly Gln Gln Gly
                805                 810                 815

Pro Tyr Ala Ser Ala Ala Ala Ala Gly Pro Gly Gln Gln Gly Pro
            820                 825                 830

Tyr Gly Pro Gly Ser Ser Ala Ala Ala Ala Gly Gln Tyr Gly Tyr
835                 840                 845

Gly Pro Gly Gln Gln Gly Pro Tyr Gly Pro Gly Ala Ser Gly Gln Asn
850                 855                 860

Gly Pro Gly Ser Gly Gln Tyr Gly Pro Gly Gln Gln Gly Pro Gly Gln
865                 870                 875                 880

Ser Ala Ala Ala Ala Gly Pro Gly Gln Gln Gly Pro Tyr Gly Pro
                885                 890                 895

Gly Ala Ser Ala Ala Ala Ala Gly Gln Tyr Gly Pro Gly Gln Gln
            900                 905                 910

Gly Pro Gly Gln Tyr Gly Pro Gly Ser Ser Gly Pro Gly Gln Gln Gly
            915                 920                 925

Pro Tyr Gly Pro Gly Ser Ser Ala Ala Ala Ala Gly Gln Tyr Gly
930                 935                 940

```
Pro Gly Gln Gln Gly Pro Tyr Gly Pro Gly Gln Ser Ala Ala Ala
945                 950                 955                 960

Ala Gly Gln Tyr Gln Gln Gly Pro Gly Gln Gly Pro Tyr Gly Pro
            965                 970                 975

Gly Ala Ser Gly Pro Gly Gln Gln Gly Pro Tyr Gly Pro Gly Ala Ser
            980                 985                 990

Ala Ala Ala Ala Ala Gly Pro Gly Gln Tyr Gly Pro Gly Gln Gln Gly
        995                 1000                1005

Pro Ser Ala Ser Ala Ala Ala Ala Gly Gln Tyr Gly Ser Gly
    1010                1015                1020

Pro Gly Gln Tyr Gly Pro Tyr Gly Pro Gly Gln Ser Gly Pro Gly
    1025                1030                1035

Ser Gly Gln Gln Gly Gln Gly Pro Tyr Gly Pro Gly Ala Ser Ala
    1040                1045                1050

Ala Ala Ala Ala Gly Gln Tyr Gly Pro Gly Gln Gln Gly Pro Tyr
    1055                1060                1065

Gly Pro Gly Gln Ser Ala Ala Ala Ala Ala Gly Pro Gly Ser Gly
    1070                1075                1080

Gln Tyr Gly Pro Gly Ala Ser Gly Gln Asn Gly Pro Gly Ser Gly
    1085                1090                1095

Gln Tyr Gly Pro Gly Gln Gln Gly Pro Gly Gln Ser Ala Ala Ala
    1100                1105                1110

Ala Ala Gly Gln Tyr Gly Gln Gly Pro Gly Gln Gln Gly Pro Tyr
    1115                1120                1125

Gly Pro Gly Ala Ser Ala Ala Ala Ala Gly Gln Tyr Gly Ser
    1130                1135                1140

Gly Pro Gly Gln Gln Gly Pro Tyr Gly Pro Gly Gln Ser Gly Ser
    1145                1150                1155

Gly Gln Gln Gly Pro Gly Gln Gln Gly Pro Tyr Ala Ser Ala Ala
    1160                1165                1170

Ala Ala Ala Gly Pro Gly Ser Gly Gln Gln Gly Pro Gly Ala Ser
    1175                1180                1185

Gly Gln Gln Gly Pro Tyr Gly Pro Gly Ala Ser Ala Ala Ala Ala
    1190                1195                1200

Ala Gly Gln Asn Gly Pro Gly Ser Gly Gln Gln Gly Pro Gly Gln
    1205                1210                1215

Ser Gly Gln Tyr Gly Pro Gly Gln Gln Gly Pro Gly Gln Gln Gly
    1220                1225                1230

Pro Gly Ser Ser Ala Ala Ala Ala Gly Pro Gly Gln Tyr Gly
    1235                1240                1245

Pro Gly Gln Gln Gly Pro Ser Ala Ser Ala Ala Ala Ala Ala Gly
    1250                1255                1260

Pro Gly Ser Gly Gln Gln Gly Pro Gly Ala Ser Gly Gln Tyr Gly
    1265                1270                1275

Pro Gly Gln Gln Gly Pro Gly Gln Gln Gly Pro Gly Ser Ser Ala
    1280                1285                1290

Ala Ala Ala Gly Gln Tyr Gly Ser Gly Pro Gly Gln Gln Gly
    1295                1300                1305

Pro Tyr Gly Ser Ala Ala Ala Ala Gly Pro Gly Ser Gly Gln
    1310                1315                1320

Tyr Gly Gln Gly Pro Tyr Gly Pro Gly Ala Ser Gly Pro Gly Gln
    1325                1330                1335

Tyr Gly Pro Gly Gln Gln Gly Pro Ser Ala Ser Ala Ala Ala Ala
```

```
            1340            1345            1350

Ala Gly Ser Gly Gln Gln Gly Pro Gly Gln Tyr Gly Pro Tyr Ala
        1355            1360            1365

Ser Ala Ala Ala Ala Ala Gly Gln Tyr Gly Ser Gly Pro Gly Gln
        1370            1375            1380

Gln Gly Pro Tyr Gly Pro Gly Gln Ser Gly Ser Gly Gln Gln Gly
        1385            1390            1395

Pro Gly Gln Gln Gly Pro Tyr Ala Ser Ala Ala Ala Ala Ala Gly
        1400            1405            1410

Pro Gly Gln Gln Gly Pro Tyr Gly Pro Gly Ser Ser Ala Ala Ala
        1415            1420            1425

Ala Ala Gly Gln Tyr Gly Tyr Gly Pro Gly Gln Gln Gly Pro Tyr
        1430            1435            1440

Gly Pro Gly Ala Ser Gly Gln Asn Gly Pro Gly Ser Gly Gln Tyr
        1445            1450            1455

Gly Pro Gly Gln Gln Gly Pro Gly Gln Ser Ala Ala Ala Ala Ala
        1460            1465            1470

Gly Pro Gly Gln Gln Gly Pro Tyr Gly Pro Gly Ala Ser Ala Ala
        1475            1480            1485

Ala Ala Ala Gly Gln Tyr Gly Pro Gly Gln Gln Gly Pro Gly Gln
        1490            1495            1500

Tyr Gly Pro Gly Ser Ser Gly Pro Gly Gln Gln Gly Pro Tyr Gly
        1505            1510            1515

Pro Gly Ser Ser Ala Ala Ala Ala Ala Gly Gln Tyr Gly Pro Gly
        1520            1525            1530

Gln Gln Gly Pro Tyr Gly Pro Gly Gln Ser Ala Ala Ala Ala Ala
        1535            1540            1545

Gly Gln Tyr Gln Gln Gly Pro Gly Gln Gln Gly Pro Tyr Gly Pro
        1550            1555            1560

Gly Ala Ser Gly Pro Gly Gln Gln Gly Pro Tyr Gly Pro Gly Ala
        1565            1570            1575

Ser Ala Ala Ala Ala Ala Gly Pro Gly Gln Tyr Gly Pro Gly Gln
        1580            1585            1590

Gln Gly Pro Ser Ala Ser Ala Ala Ala Ala Gly Gln Tyr Gly
        1595            1600            1605

Ser Gly Pro Gly Gln Tyr Gly Pro Tyr Gly Pro Gly Gln Ser Gly
        1610            1615            1620

Pro Gly Ser Gly Gln Gln Gly Gln Gly Pro Tyr Gly Pro Gly Ala
        1625            1630            1635

Ser Ala Ala Ala Ala Ala Gly Gln Tyr Gly Pro Gly Gln Gln Gly
        1640            1645            1650

Pro Tyr Gly Pro Gly Gln Ser Ala Ala Ala Ala Ala Gly Pro Gly
        1655            1660            1665

Ser Gly Gln Tyr Gly Pro Gly Ala Ser Gly Gln Asn Gly Pro Gly
        1670            1675            1680

Ser Gly Gln Tyr Gly Pro Gly Gln Gln Gly Pro Gly Gln Ser Ala
        1685            1690            1695

Ala Ala Ala Gly Gln Tyr Gln Gln Gly Pro Gly Gln Gln Gly
        1700            1705            1710

Pro Tyr Gly Pro Gly Ala Ser Ala Ala Ala Ala Ala Gly Gln Tyr
        1715            1720            1725

Gly Ser Gly Pro Gly Gln Gln Gly Pro Tyr Gly Pro Gly Gln Ser
        1730            1735            1740
```

```
Gly Ser Gly Gln Gln Gly Pro Gly Gln Gly Pro Tyr Ala Ser
    1745                1750               1755

Ala Ala Ala Ala Ala Gly Pro Gly Ser Gly Gln Gln Gly Pro Gly
    1760                1765               1770

Ala Ser Gly Gln Gln Gly Pro Tyr Gly Pro Gly Ala Ser Ala Ala
    1775                1780               1785

Ala Ala Ala Gly Gln Asn Gly Pro Gly Ser Gly Gln Gln Gly Pro
    1790                1795               1800

Gly Gln Ser Gly Gln Tyr Gly Pro Gly Gln Gly Pro Gly Gln
    1805                1810               1815

Gln Gly Pro Gly Ser Ser Ala Ala Ala Ala Gly Pro Gly Gln
    1820                1825               1830

Tyr Gly Pro Gly Gln Gln Gly Pro Ser Ala Ser Ala Ala Ala Ala
    1835                1840               1845

Ala Gly Pro Gly Ser Gly Gln Gln Gly Pro Gly Ala Ser Gly Gln
    1850                1855               1860

Tyr Gly Pro Gly Gln Gln Gly Pro Gly Gln Gln Gly Pro Gly Ser
    1865                1870               1875

Ser Ala Ala Ala Ala Ala Gly Gln Tyr Gly Ser Gly Pro Gly Gln
    1880                1885               1890

Gln Gly Pro Tyr Gly Ser Ala Ala Ala Ala Gly Pro Gly Ser
    1895                1900               1905

Gly Gln Tyr Gly Gln Gly Pro Tyr Gly Pro Gly Ala Ser Gly Pro
    1910                1915               1920

Gly Gln Tyr Gly Pro Gly Gln Gln Gly Pro Ser Ala Ser Ala Ala
    1925                1930               1935

Ala Ala Ala Gly Ser Gly Gln Gln Gly Pro Gly Gln Tyr Gly Pro
    1940                1945               1950

Tyr Ala Ser Ala Ala Ala Ala Gly Gln Tyr Gly Ser Gly Pro
    1955                1960               1965

Gly Gln Gln Gly Pro Tyr Gly Pro Gly Gln Ser Gly Ser Gly Gln
    1970                1975               1980

Gln Gly Pro Gly Gln Gln Gly Pro Tyr Ala Ser Ala Ala Ala Ala
    1985                1990               1995

Ala Gly Pro Gly Gln Gln Gly Pro Tyr Gly Pro Gly Ser Ser Ala
    2000                2005               2010

Ala Ala Ala Ala Gly Gln Tyr Gly Tyr Gly Pro Gly Gln Gln Gly
    2015                2020               2025

Pro Tyr Gly Pro Gly Ala Ser Gly Gln Asn Gly Pro Gly Ser Gly
    2030                2035               2040

Gln Tyr Gly Pro Gly Gln Gln Gly Pro Gly Gln Ser Ala Ala Ala
    2045                2050               2055

Ala Ala Gly Pro Gly Gln Gln Gly Pro Tyr Gly Pro Gly Ala Ser
    2060                2065               2070

Ala Ala Ala Ala Ala Gly Gln Tyr Gly Pro Gly Gln Gln Gly Pro
    2075                2080               2085

Gly Gln Tyr Gly Pro Gly Ser Ser Gly Pro Gly Gln Gln Gly Pro
    2090                2095               2100

Tyr Gly Pro Gly Ser Ser Ala Ala Ala Ala Gly Gln Tyr Gly
    2105                2110               2115

Pro Gly Gln Gln Gly Pro Tyr Gly Pro Gly Gln Ser Ala Ala Ala
    2120                2125               2130
```

Ala Ala Gly Gln Tyr Gln Gln Gly Pro Gly Gln Gln Gly Pro Tyr
2135                2140                2145

Gly Pro Gly Ala Ser Gly Pro Gly Gln Gln Gly Pro Tyr Gly Pro
2150                2155                2160

Gly Ala Ser Ala Ala Ala Ala Gly Pro Gly Gln Tyr Gly Pro
2165                2170                2175

Gly Gln Gln Gly Pro Ser Ala Ser Ala Ala Ala Ala Gly Gln
2180                2185                2190

Tyr Gly Ser Gly Pro Gly Gln Tyr Gly Pro Tyr Gly Pro Gly Gln
2195                2200                2205

Ser Gly Pro Gly Ser Gly Gln Gln Gly Gln Gly Pro Tyr Gly Pro
2210                2215                2220

Gly Ala Ser Ala Ala Ala Ala Gly Gln Tyr Gly Pro Gly Gln
2225                2230                2235

Gln Gly Pro Tyr Gly Pro Gly Gln Ser Ala Ala Ala Ala Ala Gly
2240                2245                2250

Pro Gly Ser Gly Gln Tyr Gly Pro Gly Ala Ser Gly Gln Asn Gly
2255                2260                2265

Pro Gly Ser Gly Gln Tyr Gly Pro Gly Gln Gln Gly Pro Gly Gln
2270                2275                2280

Ser Ala Ala Ala Ala Gly Gln Tyr Gln Gly Pro Gly Gln
2285                2290                2295

Gln Gly Pro Tyr Gly Pro Gly Ala Ser Ala Ala Ala Ala Ala Gly
2300                2305                2310

Gln Tyr Gly Ser Gly Pro Gly Gln Gln Gly Pro Tyr Gly Pro Gly
2315                2320                2325

Gln Ser Gly Ser Gly Gln Gln Gly Pro Gly Gln Gln Gly Pro Tyr
2330                2335                2340

Ala Ser Ala Ala Ala Ala Ala Gly Pro Gly Ser Gly Gln Gln Gly
2345                2350                2355

Ser Ser Val Asp Lys Leu Ala Ala Ala Leu Glu His His His His
2360                2365                2370

His His
2375

<210> SEQ ID NO 14
<211> LENGTH: 50
<212> TYPE: PRT
<213> ORGANISM: Araneus diadematus

<400> SEQUENCE: 14

Ser Gly Cys Asp Val Leu Val Gln Ala Leu Leu Glu Val Val Ser Ala
1               5                   10                  15

Leu Val Ser Ile Leu Gly Ser Ser Ser Ile Gly Gln Ile Asn Tyr Gly
                20                  25                  30

Ala Ser Ala Gln Tyr Thr Gln Met Val Gly Gln Ser Val Ala Gln Ala
        35                  40                  45

Leu Ala
    50

<210> SEQ ID NO 15
<211> LENGTH: 30
<212> TYPE: PRT
<213> ORGANISM: Araneus diadematus

<400> SEQUENCE: 15

```
Ser Gly Cys Asp Val Leu Val Gln Ala Leu Leu Glu Val Val Ser Ala
1               5                   10                  15

Leu Val Ser Ile Leu Gly Ser Ser Ile Gly Gln Ile Asn
            20                  25                  30
```

<210> SEQ ID NO 16
<211> LENGTH: 21
<212> TYPE: PRT
<213> ORGANISM: Araneus diadematus

<400> SEQUENCE: 16

```
Ser Gly Cys Asp Val Leu Val Gln Ala Leu Leu Glu Val Val Ser Ala
1               5                   10                  15

Leu Val Ser Ile Leu
            20
```

<210> SEQ ID NO 17
<211> LENGTH: 1154
<212> TYPE: PRT
<213> ORGANISM: Artificial Sequence
<220> FEATURE:
<223> OTHER INFORMATION: recombinant spider silk protein
      ADF3KaiLargeNRSH1

<400> SEQUENCE: 17

```
Met His His His His His His His His His Ser Ser Gly Ser Ser
1               5                   10                  15

Leu Glu Val Leu Phe Gln Gly Pro Ala Arg Ala Gly Ser Gly Gln Gln
            20                  25                  30

Gly Pro Gly Gln Gln Gly Pro Gly Gln Gln Gly Pro Gly Gln Gln Gly
        35                  40                  45

Pro Tyr Gly Pro Gly Ala Ser Ala Ala Ala Ala Ala Ala Gly Gly Tyr
    50                  55                  60

Gly Pro Gly Ser Gly Gln Gln Gly Pro Ser Gln Gln Gly Pro Gly Gln
65                  70                  75                  80

Gln Gly Pro Gly Gly Gln Gly Pro Tyr Gly Pro Gly Ala Ser Ala Ala
                85                  90                  95

Ala Ala Ala Ala Gly Gly Tyr Gly Pro Gly Ser Gly Gln Gln Gly Pro
            100                 105                 110

Gly Gly Gln Gly Pro Tyr Gly Pro Gly Ser Ser Ala Ala Ala Ala Ala
        115                 120                 125

Ala Gly Gly Asn Gly Pro Gly Ser Gly Gln Gln Gly Ala Gly Gln Gln
    130                 135                 140

Gly Pro Gly Gln Gln Gly Pro Gly Ala Ser Ala Ala Ala Ala Ala Ala
145                 150                 155                 160

Gly Gly Tyr Gly Pro Gly Ser Gly Gln Gln Gly Pro Gly Gln Gln Gly
                165                 170                 175

Pro Gly Gln Gly Pro Tyr Gly Pro Gly Ala Ser Ala Ala Ala Ala Ala
            180                 185                 190

Ala Ala Gly Gly Tyr Gly Pro Gly Ser Gly Gln Gly Pro Gly Gln Gln
        195                 200                 205

Gly Pro Gly Gly Gln Pro Tyr Gly Pro Gly Ala Ser Ala Ala Ala Ala
    210                 215                 220

Ala Ala Ala Gly Gly Tyr Gly Pro Gly Ser Gly Gln Gln Pro Gly Gly
225                 230                 235                 240

Gln Gln Gly Pro Gly Gln Gln Pro Gly Gly Gln Gly Pro Tyr Gly
                245                 250                 255
```

```
Pro Gly Ala Ser Ala Ala Ala Ala Ala Gly Tyr Gly Pro Gly
            260                 265                 270

Tyr Gly Gln Gln Gly Pro Gly Gln Gln Gly Pro Gly Gln Gly Pro
        275                 280                 285

Tyr Gly Pro Gly Ala Ser Ala Ala Ser Ala Ala Ser Gly Gly Tyr Gly
        290                 295                 300

Pro Gly Ser Gly Gln Gln Gly Pro Gly Gln Gln Gly Pro Gly Gln
305                 310                 315                 320

Gly Pro Tyr Gly Pro Gly Ala Ser Ala Ala Ala Ala Ala Gly Gly
            325                 330                 335

Tyr Gly Pro Gly Ser Gly Gln Gln Gly Pro Gly Gln Gln Gly Pro Gly
            340                 345                 350

Gln Gln Gly Pro Gly Gln Gln Gly Pro Gly Gln Gln Gly Pro Tyr Gly
            355                 360                 365

Pro Gly Ala Ser Ala Ala Ala Ala Ala Gly Gly Tyr Gly Pro Gly
            370                 375                 380

Ser Gly Gln Gln Gly Pro Gly Gln Gln Gly Pro Gly Gln Gln Gly Pro
385                 390                 395                 400

Gly Gln Gln Gly Pro Gly Gln Gln Gly Pro Gly Gln Gln Gly Pro Gly
            405                 410                 415

Gln Gln Gly Pro Gly Gln Gln Gly Pro Gly Gln Gln Gly Pro Gly Gly
            420                 425                 430

Gln Gly Ala Tyr Gly Pro Gly Ala Ser Ala Ala Ala Gly Ala Ala Gly
            435                 440                 445

Gly Tyr Gly Pro Gly Ser Gly Gln Gln Gly Pro Gly Gln Gln Gly Pro
        450                 455                 460

Gly Gln Gln Gly Pro Gly Gln Gln Gly Pro Gly Gln Gln Gly Pro Gly
465                 470                 475                 480

Gln Gln Gly Pro Gly Gln Gln Gly Pro Gly Gln Gln Gly Pro Tyr Gly
            485                 490                 495

Pro Gly Ala Ser Ala Ala Ala Ala Ala Gly Gly Tyr Gly Pro Gly
            500                 505                 510

Ser Gly Gln Gln Gly Pro Gly Gln Gln Gly Pro Gly Gln Gln Gly Pro
        515                 520                 525

Gly Gly Gln Gly Pro Tyr Gly Pro Gly Ala Ala Ser Ala Ala Val Ser
        530                 535                 540

Val Ser Arg Ala Arg Ala Gly Ser Gly Gln Gln Gly Pro Gly Gln Gln
545                 550                 555                 560

Gly Pro Gly Gln Gln Gly Pro Gly Gln Gln Gly Pro Tyr Gly Pro Gly
            565                 570                 575

Ala Ser Ala Ala Ala Ala Ala Ala Gly Gly Tyr Gly Pro Gly Ser Gly
            580                 585                 590

Gln Gln Gly Pro Ser Gln Gln Gly Pro Gly Gln Gln Gly Pro Gly Gly
            595                 600                 605

Gln Gly Pro Tyr Gly Pro Gly Ala Ser Ala Ala Ala Ala Ala Gly
            610                 615                 620

Gly Tyr Gly Pro Gly Ser Gly Gln Gln Gly Pro Gly Gln Gln Gly Pro
625                 630                 635                 640

Tyr Gly Pro Gly Ser Ser Ala Ala Ala Ala Ala Gly Gly Asn Gly
            645                 650                 655

Pro Gly Ser Gly Gln Gln Gly Ala Gly Gln Gln Gly Pro Gly Gln Gln
            660                 665                 670

Gly Pro Gly Ala Ser Ala Ala Ala Ala Ala Gly Gly Tyr Gly Pro
```

```
            675                 680                 685
Gly Ser Gly Gln Gln Gly Pro Gly Gln Gln Gly Pro Gly Gln Gly
    690                 695                 700
Pro Tyr Gly Pro Gly Ala Ser Ala Ala Ala Ala Ala Gly Gly Tyr
705                 710                 715                 720
Gly Pro Gly Ser Gly Gln Gln Gly Pro Gly Gln Gln Gly Pro Gly Gln
                725                 730                 735
Gly Pro Tyr Gly Pro Gly Ala Ser Ala Ala Ala Ala Ala Gly Gly
                740                 745                 750
Tyr Gly Pro Gly Ser Gly Gln Gln Gly Pro Gly Gln Gln Gly Pro Gly
                755                 760                 765
Gln Gln Gly Pro Gly Gly Gln Gly Pro Tyr Gly Pro Gly Ala Ser Ala
    770                 775                 780
Ala Ala Ala Ala Gly Gly Tyr Gly Pro Gly Tyr Gly Gln Gln Gly
785                 790                 795                 800
Pro Gly Gln Gln Gly Pro Gly Gln Gly Pro Tyr Gly Pro Gly Ala
                805                 810                 815
Ser Ala Ala Ser Ala Ala Ser Gly Gly Tyr Gly Pro Gly Ser Gly Gln
                820                 825                 830
Gln Gly Pro Gly Gln Gln Gly Pro Gly Gln Gln Gly Pro Tyr Gly Pro
    835                 840                 845
Gly Ala Ser Ala Ala Ala Ala Ala Gly Gly Tyr Gly Pro Gly Ser
850                 855                 860
Gly Gln Gln Gly Pro Gly Gln Gln Gly Pro Gly Gln Gln Gly Pro Gly
865                 870                 875                 880
Gln Gln Gly Pro Gly Gly Gln Gly Pro Tyr Gly Pro Gly Ala Ser Ala
                885                 890                 895
Ala Ala Ala Ala Gly Gly Tyr Gly Pro Gly Ser Gln Gln Gly
                900                 905                 910
Pro Gly Gln Gln Gly Pro Gly Gln Gln Gly Pro Gly Gln Gln Gly Pro
    915                 920                 925
Gly Gln Gln Gly Pro Gly Gln Gln Gly Pro Gly Gln Gln Gly Pro Gly
930                 935                 940
Gln Gln Gly Pro Gly Gln Gln Gly Pro Gly Gln Gln Gly Ala Tyr Gly
945                 950                 955                 960
Pro Gly Ala Ser Ala Ala Gly Ala Ala Gly Gly Tyr Gly Pro Gly
                965                 970                 975
Ser Gly Gln Gln Gly Pro Gly Gln Gln Gly Pro Gly Gln Gln Gly Pro
                980                 985                 990
Gly Gln Gln Gly Pro Gly Gln Gln Gly Pro Gly Gln Gln Gly Pro Gly
    995                 1000                1005
Gln Gln  Gly Pro Gly Gln Gln  Gly Pro Tyr Gly  Pro Gly Ala Ser
    1010                1015                1020
Ala Ala  Ala Ala Ala Ala Gly  Gly Tyr Gly Pro Gly  Ser Gly Gln
    1025                1030                1035
Gln Gly  Pro Gly Gln Gln Gly  Pro Gly Gln Gln Gly  Pro Gly Gly
    1040                1045                1050
Gln Gly  Pro Tyr Gly Pro Gly  Ala Ala Ser Ala Ala  Val Ser Val
    1055                1060                1065
Gly Gly  Tyr Gly Pro Gln Ser  Ser Ser Val Pro Val  Ala Ser Ala
    1070                1075                1080
Val Ala  Ser Arg Leu Ser Ser  Pro Ala Ala Ser Ser  Arg Val Ser
    1085                1090                1095
```

```
Ser Ala Val Ser Ser Leu Val Ser Ser Gly Pro Thr Lys His Ala
    1100            1105                1110

Ala Leu Ser Asn Thr Ile Ser Ser Val Val Ser Gln Val Ser Ala
    1115            1120                1125

Ser Asn Pro Gly Leu Ser Gly Cys Asp Val Leu Val Gln Ala Leu
    1130            1135                1140

Leu Glu Val Val Ser Ala Leu Val Ser Ile Leu
    1145            1150

<210> SEQ ID NO 18
<211> LENGTH: 24
<212> TYPE: PRT
<213> ORGANISM: Artificial Sequence
<220> FEATURE:
<223> OTHER INFORMATION: His tag and start codon

<400> SEQUENCE: 18

Met His His His His His His His His Ser Ser Gly Ser Ser
1               5                   10                  15

Leu Glu Val Leu Phe Gln Gly Pro
            20

<210> SEQ ID NO 19
<211> LENGTH: 590
<212> TYPE: PRT
<213> ORGANISM: Artificial Sequence
<220> FEATURE:
<223> OTHER INFORMATION: Met-PRT410

<400> SEQUENCE: 19

Met Gly Pro Gly Gln Gln Gly Pro Tyr Gly Pro Gly Ala Ser Ala
1               5                   10                  15

Ala Ala Ala Gly Gln Asn Gly Pro Gly Ser Gly Gln Gln Gly Pro
            20                  25                  30

Gln Ser Gly Gln Tyr Gly Pro Gly Gln Gln Gly Pro Gly Gln Gly
            35                  40                  45

Pro Gly Ser Ser Ala Ala Ala Ala Gly Pro Gly Gln Tyr Gly Pro
    50                  55                  60

Gly Gln Gln Gly Pro Ser Ala Ser Ala Ala Ala Ala Gly Pro Gly
65              70                  75                  80

Ser Gly Gln Gln Gly Pro Gly Ala Ser Gly Gln Tyr Gly Pro Gly Gln
            85                  90                  95

Gln Gly Pro Gly Gln Gln Gly Pro Gly Ser Ala Ala Ala Ala Ala
            100                 105                 110

Gly Gln Tyr Gly Ser Gly Pro Gly Gln Gln Gly Pro Tyr Gly Ser Ala
            115                 120                 125

Ala Ala Ala Ala Gly Pro Gly Ser Gly Gln Tyr Gly Gln Gly Pro Tyr
    130                 135                 140

Gly Pro Gly Ala Ser Gly Pro Gly Gln Tyr Gly Pro Gly Gln Gln Gly
145                 150                 155                 160

Pro Ser Ala Ser Ala Ala Ala Ala Gly Ser Gly Gln Gln Gly Pro
                165                 170                 175

Gly Gln Tyr Gly Pro Tyr Ala Ser Ala Ala Ala Ala Gly Gln Tyr
            180                 185                 190

Gly Ser Gly Pro Gly Gln Gln Gly Pro Tyr Gly Pro Gly Gln Ser Gly
            195                 200                 205

Ser Gly Gln Gln Gly Pro Gly Gln Gln Gly Pro Tyr Ala Ser Ala Ala
```

```
            210                 215                 220

Ala Ala Ala Gly Pro Gly Gln Gln Gly Pro Tyr Gly Pro Gly Ser Ser
225                 230                 235                 240

Ala Ala Ala Ala Ala Gly Gln Tyr Gly Tyr Gly Pro Gly Gln Gln Gly
                245                 250                 255

Pro Tyr Gly Pro Gly Ala Ser Gly Gln Asn Gly Pro Gly Ser Gly Gln
                260                 265                 270

Tyr Gly Pro Gly Gln Gln Gly Pro Gly Gln Ser Ala Ala Ala Ala Ala
            275                 280                 285

Gly Pro Gly Gln Gln Gly Pro Tyr Gly Pro Gly Ala Ser Ala Ala Ala
            290                 295                 300

Ala Ala Gly Gln Tyr Gly Pro Gly Gln Gln Gly Pro Gly Gln Tyr Gly
305                 310                 315                 320

Pro Gly Ser Ser Gly Pro Gly Gln Gln Gly Pro Tyr Gly Pro Gly Ser
                325                 330                 335

Ser Ala Ala Ala Ala Gly Gln Tyr Gly Pro Gly Gln Gln Gly Pro
                340                 345                 350

Tyr Gly Pro Gly Gln Ser Ala Ala Ala Ala Gly Gln Tyr Gln Gln
            355                 360                 365

Gly Pro Gly Gln Gln Gly Pro Tyr Gly Pro Gly Ala Ser Gly Pro Gly
            370                 375                 380

Gln Gln Gly Pro Tyr Gly Pro Gly Ala Ser Ala Ala Ala Ala Gly
385                 390                 395                 400

Pro Gly Gln Tyr Gly Pro Gly Gln Gln Gly Pro Ser Ala Ser Ala Ala
                405                 410                 415

Ala Ala Ala Gly Gln Tyr Gly Ser Gly Pro Gly Gln Tyr Gly Pro Tyr
            420                 425                 430

Gly Pro Gly Gln Ser Gly Pro Gly Ser Gly Gln Gln Gly Gln Gly Pro
            435                 440                 445

Tyr Gly Pro Gly Ala Ser Ala Ala Ala Ala Gly Gln Tyr Gly Pro
            450                 455                 460

Gly Gln Gln Gly Pro Tyr Gly Pro Gly Gln Ser Ala Ala Ala Ala
465                 470                 475                 480

Gly Pro Gly Ser Gly Gln Tyr Gly Pro Gly Ala Ser Gly Gln Asn Gly
                485                 490                 495

Pro Gly Ser Gly Gln Tyr Gly Pro Gly Gln Gln Gly Pro Gly Gln Ser
                500                 505                 510

Ala Ala Ala Ala Ala Gly Gln Tyr Gln Gln Gly Pro Gly Gln Gln Gly
            515                 520                 525

Pro Tyr Gly Pro Gly Ala Ser Ala Ala Ala Ala Gly Gln Tyr Gly
            530                 535                 540

Ser Gly Pro Gly Gln Gln Gly Pro Tyr Gly Pro Gly Gln Ser Gly Ser
545                 550                 555                 560

Gly Gln Gln Gly Pro Gly Gln Gln Gly Pro Tyr Ala Ser Ala Ala Ala
                565                 570                 575

Ala Ala Gly Pro Gly Ser Gly Gln Gln Gly Pro Gly Ala Ser
                580                 585                 590

<210> SEQ ID NO 20
<211> LENGTH: 612
<212> TYPE: PRT
<213> ORGANISM: Artificial Sequence
<220> FEATURE:
<223> OTHER INFORMATION: Met-PRT720
```

```
<400> SEQUENCE: 20

Met Gly Pro Gly Gln Gln Gly Pro Tyr Gly Pro Gly Ala Ser Ala Ala
1               5                   10                  15

Ala Ala Ala Gly Gln Asn Gly Pro Gly Ser Gly Gln Gln Gly Pro Gly
                20                  25                  30

Gln Ser Gly Gln Tyr Gly Pro Gly Gln Gln Gly Pro Gly Gln Gln Gly
            35                  40                  45

Pro Gly Ser Ser Ala Ala Ala Ala Gly Pro Gly Gln Tyr Val Leu
        50                  55                  60

Ile Gly Pro Gly Gln Gln Val Leu Ile Gly Pro Ser Ala Ser Ala Ala
65                  70                  75                  80

Ala Ala Ala Gly Pro Gly Ser Gly Gln Gln Gly Pro Gly Ala Ser Gly
                85                  90                  95

Gln Tyr Gly Pro Gly Gln Gly Pro Gly Gln Gln Gly Pro Gly Ser
            100                 105                 110

Ser Ala Ala Ala Ala Gly Ser Tyr Gly Ser Val Leu Ile Gly Pro
        115                 120                 125

Gly Gln Gln Val Leu Ile Gly Pro Tyr Gly Ser Ala Ala Ala Ala
    130                 135                 140

Gly Pro Gly Ser Gly Gln Tyr Gly Gln Gly Pro Tyr Gly Pro Gly Ala
145                 150                 155                 160

Ser Gly Pro Gly Gln Tyr Gly Pro Gly Gln Gln Gly Pro Ser Ala Ser
                165                 170                 175

Ala Ala Ala Ala Ala Gly Ser Gly Gln Gln Val Leu Ile Gly Pro Gly
            180                 185                 190

Gln Tyr Val Leu Ile Gly Pro Tyr Ala Ser Ala Ala Ala Ala Gly
    195                 200                 205

Gln Tyr Gly Ser Gly Pro Gly Gln Gln Gly Pro Tyr Gly Pro Gly Gln
210                 215                 220

Ser Gly Ser Gly Gln Gln Gly Pro Gly Gln Gln Gly Pro Tyr Ala Ser
225                 230                 235                 240

Ala Ala Ala Ala Ala Gly Pro Gly Gln Gln Val Leu Ile Gly Pro Tyr
            245                 250                 255

Val Leu Ile Gly Pro Gly Ser Ser Ala Ala Ala Ala Gly Gln Tyr
        260                 265                 270

Gly Tyr Gly Pro Gly Gln Gln Gly Pro Tyr Gly Pro Gly Ala Ser Gly
    275                 280                 285

Gln Asn Gly Pro Gly Ser Gly Gln Tyr Gly Pro Gly Gln Gln Gly Pro
        290                 295                 300

Gly Gln Ser Ala Ala Ala Ala Gly Pro Gly Gln Gln Val Leu Ile
305                 310                 315                 320

Gly Pro Tyr Val Leu Ile Gly Pro Gly Ala Ser Ala Ala Ala Ala
            325                 330                 335

Gly Gln Tyr Gly Pro Gly Gln Gln Gly Pro Gly Gln Tyr Gly Pro Gly
        340                 345                 350

Ser Ser Gly Pro Gly Gln Gln Gly Pro Tyr Gly Pro Gly Ser Ser Ala
        355                 360                 365

Ala Ala Ala Gly Ser Tyr Gly Pro Gly Gln Gln Val Leu Ile Gly
            370                 375                 380

Pro Tyr Val Leu Ile Gly Pro Gly Pro Ser Ala Ala Ala Ala Gly
385                 390                 395                 400

Gln Tyr Gln Gln Gly Pro Gly Gln Gln Gly Pro Tyr Gly Pro Gly Ala
            405                 410                 415
```

-continued

Ser Gly Pro Gly Gln Gln Gly Pro Tyr Gly Pro Gly Ala Ser Ala Ala
            420                 425                 430

Ala Ala Ala Gly Pro Gly Gln Tyr Val Leu Ile Gly Pro Gly Gln Gln
            435                 440                 445

Val Leu Ile Gly Pro Ser Ala Ser Ala Ala Ala Gly Gln Tyr
450                 455                 460

Gly Ser Gly Pro Gly Gln Tyr Gly Pro Tyr Gly Pro Gly Gln Ser Gly
465                 470                 475                 480

Pro Gly Ser Gly Gln Gln Gly Gln Gly Pro Tyr Gly Pro Gly Ala Ser
            485                 490                 495

Ala Ala Ala Ala Gly Ser Tyr Gly Pro Gly Gln Gln Val Leu Ile
            500                 505                 510

Gly Pro Tyr Val Leu Ile Gly Pro Gly Ser Ala Ala Ala Ala
            515                 520                 525

Gly Pro Gly Ser Gly Gln Tyr Gly Pro Gly Ala Ser Gly Gln Asn Gly
            530                 535                 540

Pro Gly Ser Gly Gln Tyr Gly Pro Gly Gln Gln Gly Pro Gly Gln Ser
545                 550                 555                 560

Ala Ala Ala Ala Gly Gln Tyr Gln Gln Val Leu Ile Gly Pro Gly
            565                 570                 575

Gln Gln Gly Pro Tyr Val Leu Ile Gly Pro Gly Ala Ser Ala Ala Ala
            580                 585                 590

Ala Ala Gly Pro Gly Ser Gly Gln Gln Val Leu Ile Gly Pro Gly Ala
            595                 600                 605

Ser Val Leu Ile
    610

<210> SEQ ID NO 21
<211> LENGTH: 565
<212> TYPE: PRT
<213> ORGANISM: Artificial Sequence
<220> FEATURE:
<223> OTHER INFORMATION: Met-PRT468

<400> SEQUENCE: 21

Met Gly Pro Gly Gln Gln Gly Pro Tyr Gly Pro Gly Ala Ser Ala Ala
1               5                   10                  15

Ala Ala Ala Ala Gly Ser Asn Gly Pro Gly Ser Gly Gln Gln Gly
            20                  25                  30

Pro Gly Gln Ser Gly Gln Tyr Gly Pro Gly Gln Gln Gly Pro Gly Gln
            35                  40                  45

Gln Gly Pro Gly Ser Ser Ala Ala Ala Ala Ala Ala Gly Pro Gly
50                  55                  60

Gln Tyr Gly Pro Gly Gln Gln Gly Pro Ser Ala Ser Ala Ala Ala
65                  70                  75                  80

Ala Ala Ala Gly Pro Gly Ser Gly Gln Gln Gly Pro Gly Ala Ser Gly
            85                  90                  95

Gln Tyr Gly Pro Gly Gln Gln Gly Pro Gly Gln Gln Gly Pro Gly Ser
            100                 105                 110

Ser Ala Ala Ala Ala Ala Ala Gly Ser Tyr Gly Ser Gly Pro Gly
            115                 120                 125

Gln Gln Gly Pro Tyr Gly Ser Ala Ala Ala Ala Ala Ala Gly Pro
            130                 135                 140

Gly Ser Gly Gln Tyr Gly Gln Gly Pro Tyr Gly Pro Gly Ala Ser Gly
145                 150                 155                 160

```
Pro Gly Gln Tyr Gly Pro Gln Gln Gly Pro Ser Ala Ser Ala Ala
            165                 170                 175

Ala Ala Ala Ala Ala Gly Ser Gly Gln Gln Gly Pro Gly Gln Tyr Gly
            180                 185                 190

Pro Tyr Ala Ser Ala Ala Ala Ala Ala Ala Gly Ser Tyr Gly Ser
            195                 200                 205

Gly Pro Gly Gln Gln Gly Pro Tyr Gly Pro Gln Ser Gly Ser Gly
            210                 215                 220

Gln Gln Gly Pro Gly Gln Gln Gly Pro Tyr Ala Ser Ala Ala Ala
225                 230                 235                 240

Ala Ala Ala Gly Pro Gly Gln Gln Gly Pro Tyr Gly Pro Gly Ser Ser
            245                 250                 255

Ala Ala Ala Ala Ala Ala Gly Ser Tyr Gly Tyr Gly Pro Gly Gln
            260                 265                 270

Gln Gly Pro Tyr Gly Pro Gly Ala Ser Gly Gln Asn Gly Pro Gly Ser
            275                 280                 285

Gly Gln Tyr Gly Pro Gly Gln Gln Gly Pro Gly Pro Ser Ala Ala Ala
            290                 295                 300

Ala Ala Ala Ala Gly Pro Gly Gln Gln Gly Pro Tyr Gly Pro Gly Ala
305                 310                 315                 320

Ser Ala Ala Ala Ala Ala Ala Gly Ser Tyr Gly Pro Gly Gln Gln
            325                 330                 335

Gly Pro Gly Gln Tyr Gly Pro Gly Ser Ser Gly Pro Gly Gln Gln Gly
            340                 345                 350

Pro Tyr Gly Pro Gly Ser Ser Ala Ala Ala Ala Ala Ala Gly Ser
            355                 360                 365

Tyr Gly Pro Gly Gln Gln Gly Pro Tyr Gly Pro Gly Pro Ser Ala Ala
            370                 375                 380

Ala Ala Ala Ala Ala Gly Ser Tyr Gln Gln Gly Pro Gly Gln Gln Gly
385                 390                 395                 400

Pro Tyr Gly Pro Gly Ala Ser Gly Pro Gly Gln Gln Gly Pro Tyr Gly
            405                 410                 415

Pro Gly Ala Ser Ala Ala Ala Ala Ala Ala Gly Pro Gly Gln Tyr
            420                 425                 430

Gly Pro Gly Gln Gln Gly Pro Ser Ala Ser Ala Ala Ala Ala Ala
            435                 440                 445

Ala Gly Ser Tyr Gly Ser Gly Pro Gly Gln Tyr Gly Pro Tyr Gly Pro
            450                 455                 460

Gly Gln Ser Gly Pro Gly Ser Gly Gln Gln Gly Gln Gly Pro Tyr Gly
465                 470                 475                 480

Pro Gly Ala Ser Ala Ala Ala Ala Ala Ala Gly Ser Tyr Gly Pro
            485                 490                 495

Gly Gln Gln Gly Pro Tyr Gly Pro Gly Ser Ala Ala Ala Ala Ala
            500                 505                 510

Ala Ala Gly Pro Gly Ser Gly Gln Tyr Gly Pro Gly Ala Ser Gly Gln
            515                 520                 525

Asn Gly Pro Gly Ser Gly Gln Tyr Gly Pro Gly Gln Gln Gly Pro Gly
            530                 535                 540

Pro Ser Ala Ala Ala Ala Ala Ala Gly Pro Gly Ser Gly Gln Gln
545                 550                 555                 560

Gly Pro Gly Ala Ser
            565
```

<210> SEQ ID NO 22
<211> LENGTH: 592
<212> TYPE: PRT
<213> ORGANISM: Artificial Sequence
<220> FEATURE:
<223> OTHER INFORMATION: Met-PRT665

<400> SEQUENCE: 22

```
Met Gly Pro Gly Gln Gln Gly Pro Tyr Gly Pro Gly Ala Ser Ala Ala
1               5                   10                  15

Ala Ala Ala Ala Ala Gly Ser Asn Gly Pro Gly Ser Gly Gln Gln Gly
            20                  25                  30

Pro Gly Gln Ser Gly Gln Tyr Gly Pro Gly Gln Gln Gly Pro Gly Gln
        35                  40                  45

Gln Gly Pro Gly Ser Ser Ala Ala Ala Ala Ala Ala Gly Pro Gly
    50                  55                  60

Gln Tyr Val Leu Ile Gly Pro Gly Gln Gln Gly Pro Ser Ala Ser Ala
65              70                  75                  80

Ala Ala Ala Ala Ala Gly Pro Gly Ser Gly Gln Gln Gly Pro Gly
            85                  90                  95

Ala Ser Gly Gln Tyr Gly Pro Gly Gln Gln Gly Pro Gly Gln Gln Gly
            100                 105                 110

Pro Gly Ser Ser Ala Ala Ala Ala Ala Ala Gly Ser Tyr Gly Ser
        115                 120                 125

Val Leu Ile Gly Pro Gly Gln Gln Pro Tyr Gly Ser Ala Ala Ala
    130                 135                 140

Ala Ala Ala Ala Gly Pro Gly Ser Gly Gln Tyr Gly Gln Gly Pro Tyr
145                 150                 155                 160

Gly Pro Gly Ala Ser Gly Pro Gly Gln Tyr Gly Pro Gly Gln Gln Gly
                165                 170                 175

Pro Ser Ala Ser Ala Ala Ala Ala Ala Ala Gly Ser Gly Gln Gln
        180                 185                 190

Val Leu Ile Gly Pro Gly Gln Tyr Gly Pro Tyr Ala Ser Ala Ala Ala
    195                 200                 205

Ala Ala Ala Ala Gly Ser Tyr Gly Ser Gly Pro Gly Gln Gln Gly Pro
    210                 215                 220

Tyr Gly Pro Gly Gln Ser Gly Ser Gly Gln Gln Gly Pro Gly Gln Gln
225                 230                 235                 240

Gly Pro Tyr Ala Ser Ala Ala Ala Ala Ala Ala Gly Pro Gly Gln
                245                 250                 255

Gln Val Leu Ile Gly Pro Tyr Gly Pro Gly Ser Ser Ala Ala Ala Ala
        260                 265                 270

Ala Ala Ala Gly Ser Tyr Gly Tyr Gly Pro Gly Gln Gln Gly Pro Tyr
    275                 280                 285

Gly Pro Gly Ala Ser Gly Gln Asn Gly Pro Gly Ser Gly Gln Tyr Gly
    290                 295                 300

Pro Gly Gln Gln Gly Pro Gly Pro Ser Ala Ala Ala Ala Ala Ala Ala
305                 310                 315                 320

Gly Pro Gly Gln Gln Val Leu Ile Gly Pro Tyr Gly Pro Gly Ala Ser
                325                 330                 335

Ala Ala Ala Ala Ala Ala Ala Gly Ser Tyr Gly Pro Gly Gln Gln Gly
            340                 345                 350

Pro Gly Gln Tyr Gly Pro Gly Ser Ser Gly Pro Gly Gln Gln Gly Pro
        355                 360                 365
```

-continued

Tyr Gly Pro Gly Ser Ser Ala Ala Ala Ala Ala Gly Ser Tyr
    370                 375                 380

Gly Pro Gly Gln Gln Val Leu Ile Gly Pro Tyr Gly Pro Gly Pro Ser
385                 390                 395                 400

Ala Ala Ala Ala Ala Ala Gly Ser Tyr Gln Gln Gly Pro Gly Gln
                405                 410                 415

Gln Gly Pro Tyr Gly Pro Gly Ala Ser Gly Pro Gly Gln Gln Gly Pro
            420                 425                 430

Tyr Gly Pro Gly Ala Ser Ala Ala Ala Ala Ala Ala Gly Pro Gly
            435                 440                 445

Gln Tyr Val Leu Ile Gly Pro Gly Gln Gln Gly Pro Ser Ala Ser Ala
450                 455                 460

Ala Ala Ala Ala Ala Gly Ser Tyr Gly Ser Gly Pro Gly Gln Tyr
465                 470                 475                 480

Gly Pro Tyr Gly Pro Gly Gln Ser Gly Pro Gly Ser Gly Gln Gln Gly
                485                 490                 495

Gln Gly Pro Tyr Gly Pro Gly Ala Ser Ala Ala Ala Ala Ala Ala
            500                 505                 510

Gly Ser Tyr Gly Pro Gly Gln Gln Val Leu Ile Gly Pro Tyr Gly Pro
    515                 520                 525

Gly Pro Ser Ala Ala Ala Ala Ala Ala Gly Pro Gly Ser Gly Gln
    530                 535                 540

Tyr Gly Pro Gly Ala Ser Gly Gln Asn Gly Pro Gly Ser Gly Gln Tyr
545                 550                 555                 560

Gly Pro Gly Gln Gln Gly Pro Gly Pro Ser Ala Ala Ala Ala Ala
                565                 570                 575

Ala Gly Pro Gly Ser Gly Gln Gln Gly Pro Gly Ala Ser Val Leu Ile
                580                 585                 590

<210> SEQ ID NO 23
<211> LENGTH: 619
<212> TYPE: PRT
<213> ORGANISM: Artificial Sequence
<220> FEATURE:
<223> OTHER INFORMATION: Met-PRT666

<400> SEQUENCE: 23

Met Gly Pro Gly Gln Gln Gly Pro Tyr Gly Pro Gly Ala Ser Ala Ala
1               5                   10                  15

Ala Ala Ala Ala Gly Ser Asn Gly Pro Gly Ser Gly Gln Gln Gly
                20                  25                  30

Pro Gly Gln Ser Gly Gln Tyr Gly Pro Gly Gln Gln Gly Pro Gly Gln
            35                  40                  45

Gln Gly Pro Gly Ser Ser Ala Ala Ala Ala Ala Ala Gly Pro Gly
    50                  55                  60

Gln Tyr Val Leu Ile Gly Pro Gly Gln Gln Val Leu Ile Gly Pro Ser
65                  70                  75                  80

Ala Ser Ala Ala Ala Ala Ala Ala Gly Pro Gly Ser Gly Gln Gln
                85                  90                  95

Gly Pro Gly Ala Ser Gly Gln Tyr Gly Pro Gly Gln Gln Gly Pro Gly
            100                 105                 110

Gln Gln Gly Pro Gly Ser Ser Ala Ala Ala Ala Ala Ala Gly Ser
    115                 120                 125

Tyr Gly Ser Val Leu Ile Gly Pro Gly Gln Gln Val Leu Ile Gly Pro
    130                 135                 140

```
Tyr Gly Ser Ala Ala Ala Ala Ala Gly Pro Gly Ser Gly Gln
145                 150                 155                 160

Tyr Gly Gln Gly Pro Tyr Gly Pro Gly Ala Ser Gly Pro Gly Gln Tyr
            165                 170                 175

Gly Pro Gly Gln Gln Gly Pro Ser Ala Ser Ala Ala Ala Ala Ala
                180                 185                 190

Ala Gly Ser Gly Gln Gln Val Leu Ile Gly Pro Gly Gln Tyr Val Leu
        195                 200                 205

Ile Gly Pro Tyr Ala Ser Ala Ala Ala Ala Ala Gly Ser Tyr
210                 215                 220

Gly Ser Gly Pro Gly Gln Gln Gly Pro Tyr Gly Pro Gly Gln Ser Gly
225                 230                 235                 240

Ser Gly Gln Gln Gly Pro Gly Gln Gln Gly Pro Tyr Ala Ser Ala Ala
                245                 250                 255

Ala Ala Ala Ala Ala Gly Pro Gly Gln Gln Val Leu Ile Gly Pro Tyr
            260                 265                 270

Val Leu Ile Gly Pro Gly Ser Ser Ala Ala Ala Ala Ala Ala Gly
            275                 280                 285

Ser Tyr Gly Tyr Gly Pro Gly Gln Gln Gly Pro Tyr Gly Pro Gly Ala
290                 295                 300

Ser Gly Gln Asn Gly Pro Gly Ser Gly Gln Tyr Gly Pro Gly Gln Gln
305                 310                 315                 320

Gly Pro Gly Pro Ser Ala Ala Ala Ala Ala Ala Gly Pro Gly Gln
                325                 330                 335

Gln Val Leu Ile Gly Pro Tyr Val Leu Ile Gly Pro Gly Ala Ser Ala
        340                 345                 350

Ala Ala Ala Ala Ala Gly Ser Tyr Gly Pro Gly Gln Gln Gly Pro
            355                 360                 365

Gly Gln Tyr Gly Pro Gly Ser Ser Gly Pro Gly Gln Gln Gly Pro Tyr
        370                 375                 380

Gly Pro Gly Ser Ser Ala Ala Ala Ala Ala Ala Gly Ser Tyr Gly
385                 390                 395                 400

Pro Gly Gln Gln Val Leu Ile Gly Pro Tyr Val Leu Ile Gly Pro Gly
            405                 410                 415

Pro Ser Ala Ala Ala Ala Ala Ala Gly Ser Tyr Gln Gln Gly Pro
            420                 425                 430

Gly Gln Gln Gly Pro Tyr Gly Pro Gly Ala Ser Gly Pro Gly Gln Gln
        435                 440                 445

Gly Pro Tyr Gly Pro Gly Ala Ser Ala Ala Ala Ala Ala Ala Gly
        450                 455                 460

Pro Gly Gln Tyr Val Leu Ile Gly Pro Gly Gln Gln Val Leu Ile Gly
465                 470                 475                 480

Pro Ser Ala Ser Ala Ala Ala Ala Ala Gly Ser Tyr Gly Ser
            485                 490                 495

Gly Pro Gly Gln Tyr Gly Pro Tyr Gly Pro Gly Gln Ser Gly Pro Gly
            500                 505                 510

Ser Gly Gln Gln Gly Gln Gly Pro Tyr Gly Pro Gly Ala Ser Ala Ala
        515                 520                 525

Ala Ala Ala Ala Gly Ser Tyr Gly Pro Gly Gln Gln Val Leu Ile
            530                 535                 540

Gly Pro Tyr Val Leu Ile Gly Pro Gly Pro Ser Ala Ala Ala Ala Ala
545                 550                 555                 560

Ala Ala Gly Pro Gly Ser Gly Gln Tyr Gly Pro Gly Ala Ser Gly Gln
```

```
                    565                 570                 575
Asn Gly Pro Gly Ser Gly Gln Tyr Gly Pro Gly Gln Gly Pro Gly
                580                 585                 590

Pro Ser Ala Ala Ala Ala Ala Ala Gly Pro Gly Ser Gly Gln Gln
            595                 600                 605

Val Leu Ile Gly Pro Gly Ala Ser Val Leu Ile
        610                 615

<210> SEQ ID NO 24
<211> LENGTH: 623
<212> TYPE: PRT
<213> ORGANISM: Artificial Sequence
<220> FEATURE:
<223> OTHER INFORMATION: PRT468

<400> SEQUENCE: 24

Met His His His His His Ser Ser Gly Ser Ser Gly Pro Gly Gln
1               5                   10                  15

Gln Gly Pro Tyr Gly Pro Gly Ala Ser Ala Ala Ala Ala Gly Gln
            20                  25                  30

Asn Gly Pro Gly Ser Gly Gln Gln Gly Pro Gly Gln Ser Gly Gln Tyr
            35                  40                  45

Gly Pro Gly Gln Gln Gly Pro Gly Gln Gly Pro Gly Ser Ser Ala
    50                  55                  60

Ala Ala Ala Gly Pro Gly Gln Tyr Val Leu Ile Gly Pro Gly Gln
65                  70                  75                  80

Gln Val Leu Ile Gly Pro Ser Ala Ser Ala Ala Ala Ala Gly Pro
                85                  90                  95

Gly Ser Gly Gln Gln Gly Pro Gly Ala Ser Gly Gln Tyr Gly Pro Gly
            100                 105                 110

Gln Gln Gly Pro Gly Gln Gln Gly Pro Gly Ser Ser Ala Ala Ala Ala
        115                 120                 125

Ala Gly Ser Tyr Gly Ser Val Leu Ile Gly Pro Gly Gln Gln Val Leu
    130                 135                 140

Ile Gly Pro Tyr Gly Ser Ala Ala Ala Ala Gly Pro Gly Ser Gly
145                 150                 155                 160

Gln Tyr Gly Gln Gly Pro Tyr Gly Pro Gly Ala Ser Gly Pro Gly Gln
            165                 170                 175

Tyr Gly Pro Gly Gln Gln Gly Pro Ser Ala Ser Ala Ala Ala Ala
        180                 185                 190

Gly Ser Gly Gln Gln Val Leu Ile Gly Pro Gly Gln Tyr Val Leu Ile
    195                 200                 205

Gly Pro Tyr Ala Ser Ala Ala Ala Ala Gln Tyr Gly Ser Gly
    210                 215                 220

Pro Gly Gln Gln Gly Pro Tyr Gly Pro Gly Gln Ser Gly Ser Gly Gln
225                 230                 235                 240

Gln Gly Pro Gly Gln Gln Gly Pro Tyr Ala Ser Ala Ala Ala Ala
            245                 250                 255

Gly Pro Gly Gln Gln Val Leu Ile Gly Pro Tyr Val Leu Ile Gly Pro
        260                 265                 270

Gly Ser Ser Ala Ala Ala Ala Gly Gln Tyr Gly Tyr Gly Pro Gly
            275                 280                 285

Gln Gln Gly Pro Tyr Gly Pro Gly Ala Ser Gln Asn Gly Pro Gly
        290                 295                 300

Ser Gly Gln Tyr Gly Pro Gly Gln Gln Gly Pro Gly Gln Ser Ala Ala
```

```
            305                 310                 315                 320
    Ala Ala Ala Gly Pro Gly Gln Gln Val Leu Ile Gly Pro Tyr Val Leu
                    325                 330                 335

Ile Gly Pro Gly Ala Ser Ala Ala Ala Ala Gly Gln Tyr Gly Pro
                340                 345                 350

Gly Gln Gln Gly Pro Gly Tyr Gly Pro Gly Ser Ser Gly Pro Gly
                    355                 360                 365

Gln Gln Gly Pro Tyr Gly Pro Gly Ser Ala Ala Ala Ala Gly
        370                 375                 380

Ser Tyr Gly Pro Gly Gln Gln Val Leu Ile Gly Pro Tyr Val Leu Ile
    385                 390                 395                 400

Gly Pro Gly Pro Ser Ala Ala Ala Ala Gly Gln Tyr Gln Gln Gly
                    405                 410                 415

Pro Gly Gln Gln Gly Pro Tyr Gly Pro Gly Ala Ser Gly Pro Gly Gln
                420                 425                 430

Gln Gly Pro Tyr Gly Pro Gly Ala Ser Ala Ala Ala Ala Gly Pro
            435                 440                 445

Gly Gln Tyr Val Leu Ile Gly Pro Gly Gln Gln Val Leu Ile Gly Pro
            450                 455                 460

Ser Ala Ser Ala Ala Ala Ala Gly Gln Tyr Gly Ser Gly Pro Gly
    465                 470                 475                 480

Gln Tyr Gly Pro Tyr Gly Pro Gly Gln Ser Gly Pro Gly Ser Gly Gln
                    485                 490                 495

Gln Gly Gln Gly Pro Tyr Gly Pro Gly Ala Ser Ala Ala Ala Ala
                500                 505                 510

Gly Ser Tyr Gly Pro Gly Gln Gln Val Leu Ile Gly Pro Tyr Val Leu
            515                 520                 525

Ile Gly Pro Gly Pro Ser Ala Ala Ala Ala Gly Pro Gly Ser Gly
            530                 535                 540

Gln Tyr Gly Pro Gly Ala Ser Gly Gln Asn Gly Pro Gly Ser Gly Gln
    545                 550                 555                 560

Tyr Gly Pro Gly Gln Gln Gly Pro Gly Gln Ser Ala Ala Ala Ala
                    565                 570                 575

Gly Gln Tyr Gln Gln Val Leu Ile Gly Pro Gly Gln Gly Pro Tyr
                580                 585                 590

Val Leu Ile Gly Pro Gly Ala Ser Ala Ala Ala Ala Gly Pro Gly
                595                 600                 605

Ser Gly Gln Gln Val Leu Ile Gly Pro Gly Ala Ser Val Leu Ile
    610                 615                 620

<210> SEQ ID NO 25
<211> LENGTH: 603
<212> TYPE: PRT
<213> ORGANISM: Artificial Sequence
<220> FEATURE:
<223> OTHER INFORMATION: PRT665

<400> SEQUENCE: 25

Met His His His His His Ser Ser Gly Ser Ser Gly Pro Gly Gln
1               5                   10                  15

Gln Gly Pro Tyr Gly Pro Gly Ala Ser Ala Ala Ala Ala Ala Ala
                20                  25                  30

Gly Ser Asn Gly Pro Gly Ser Gly Gln Gln Pro Gly Gln Ser Gly
            35                  40                  45

Gln Tyr Gly Pro Gly Gln Gln Gly Pro Gly Gln Gln Gly Pro Gly Ser
```

```
                50                  55                  60
Ser Ala Ala Ala Ala Ala Ala Gly Pro Gly Gln Tyr Val Leu Ile
 65                  70                  75                  80

Gly Pro Gly Gln Gln Gly Pro Ser Ala Ser Ala Ala Ala Ala Ala
                 85                  90                  95

Ala Gly Pro Gly Ser Gly Gln Gln Gly Pro Gly Ala Ser Gly Gln Tyr
                100                 105                 110

Gly Pro Gly Gln Gln Gly Pro Gly Gln Gln Pro Gly Ser Ser Ala
                115                 120                 125

Ala Ala Ala Ala Ala Ala Gly Ser Tyr Gly Ser Val Leu Ile Gly Pro
                130                 135                 140

Gly Gln Gln Gly Pro Tyr Gly Ser Ala Ala Ala Ala Ala Ala Gly
145                 150                 155                 160

Pro Gly Ser Gly Gln Tyr Gly Gln Gly Pro Tyr Gly Pro Gly Ala Ser
                165                 170                 175

Gly Pro Gly Gln Tyr Gly Pro Gly Gln Gln Gly Pro Ser Ala Ser Ala
                180                 185                 190

Ala Ala Ala Ala Ala Ala Gly Ser Gly Gln Gln Val Leu Ile Gly Pro
                195                 200                 205

Gly Gln Tyr Gly Pro Tyr Ala Ser Ala Ala Ala Ala Ala Ala Gly
210                 215                 220

Ser Tyr Gly Ser Gly Pro Gly Gln Gln Gly Pro Tyr Gly Pro Gly Gln
225                 230                 235                 240

Ser Gly Ser Gly Gln Gln Gly Pro Gly Gln Gln Gly Pro Tyr Ala Ser
                245                 250                 255

Ala Ala Ala Ala Ala Ala Gly Pro Gly Gln Gln Val Leu Ile Gly
                260                 265                 270

Pro Tyr Gly Pro Gly Ser Ser Ala Ala Ala Ala Ala Ala Gly Ser
                275                 280                 285

Tyr Gly Tyr Gly Pro Gly Gln Gln Gly Pro Tyr Gly Pro Gly Ala Ser
                290                 295                 300

Gly Gln Asn Gly Pro Gly Ser Gly Gln Tyr Gly Pro Gly Gln Gln Gly
305                 310                 315                 320

Pro Gly Pro Ser Ala Ala Ala Ala Ala Ala Gly Pro Gly Gln Gln
                325                 330                 335

Val Leu Ile Gly Pro Tyr Gly Pro Gly Ala Ser Ala Ala Ala Ala
                340                 345                 350

Ala Ala Gly Ser Tyr Gly Pro Gly Gln Gln Gly Pro Gly Gln Tyr Gly
                355                 360                 365

Pro Gly Ser Ser Gly Pro Gly Gln Gln Gly Pro Tyr Gly Pro Gly Ser
                370                 375                 380

Ser Ala Ala Ala Ala Ala Ala Gly Ser Tyr Gly Pro Gly Gln Gln
385                 390                 395                 400

Val Leu Ile Gly Pro Tyr Gly Pro Gly Ser Ala Ala Ala Ala Ala
                405                 410                 415

Ala Ala Gly Ser Tyr Gln Gln Gly Pro Gly Gln Gln Gly Pro Tyr Gly
                420                 425                 430

Pro Gly Ala Ser Gly Pro Gly Gln Gln Gly Pro Tyr Gly Pro Gly Ala
                435                 440                 445

Ser Ala Ala Ala Ala Ala Ala Ala Gly Pro Gly Gln Tyr Val Leu Ile
                450                 455                 460

Gly Pro Gly Gln Gln Gly Pro Ser Ala Ser Ala Ala Ala Ala Ala Ala
465                 470                 475                 480
```

```
Ala Gly Ser Tyr Gly Ser Gly Pro Gly Gln Tyr Pro Tyr Gly Pro
                485                 490                 495

Gly Gln Ser Gly Pro Gly Ser Gly Gln Gly Gln Gly Pro Tyr Gly
                500                 505                 510

Pro Gly Ala Ser Ala Ala Ala Ala Ala Ala Gly Ser Tyr Gly Pro
                515                 520                 525

Gly Gln Gln Val Leu Ile Gly Pro Tyr Gly Pro Gly Pro Ser Ala Ala
                530                 535                 540

Ala Ala Ala Ala Ala Gly Pro Gly Ser Gly Gln Tyr Gly Pro Gly Ala
545                 550                 555                 560

Ser Gly Gln Asn Gly Pro Gly Ser Gly Gln Tyr Gly Pro Gly Gln Gln
                565                 570                 575

Gly Pro Gly Pro Ser Ala Ala Ala Ala Ala Ala Gly Pro Gly Ser
                580                 585                 590

Gly Gln Gln Gly Pro Gly Ala Ser Val Leu Ile
                595                 600

<210> SEQ ID NO 26
<211> LENGTH: 559
<212> TYPE: PRT
<213> ORGANISM: Artificial Sequence
<220> FEATURE:
<223> OTHER INFORMATION: Recombinant spider silk protein Flag_92_short2

<400> SEQUENCE: 26

Met His His His His His His His His Ser Ser Gly Ser Ser
1               5                   10                  15

Leu Glu Val Leu Phe Gln Gly Pro Gly Ala Gly Gly Ser Gly Pro Gly
                20                  25                  30

Gly Ala Gly Pro Gly Gly Val Gly Pro Gly Gly Ser Gly Pro Gly Gly
                35                  40                  45

Val Gly Pro Gly Gly Ser Gly Pro Gly Gly Val Gly Pro Gly Gly Ser
                50                  55                  60

Gly Pro Gly Gly Val Gly Pro Gly Gly Ala Gly Pro Tyr Gly Pro
65                  70                  75                  80

Gly Gly Ser Gly Pro Gly Ala Gly Ala Gly Pro Gly Gly
                85                  90                  95

Ala Tyr Gly Pro Gly Gly Ser Tyr Gly Pro Gly Gly Ser Gly Gly Pro
                100                 105                 110

Gly Gly Ala Gly Pro Tyr Gly Pro Gly Gly Glu Gly Pro Gly Gly
                115                 120                 125

Ala Gly Pro Tyr Gly Pro Gly Gly Ala Gly Pro Tyr Gly Pro
                130                 135                 140

Gly Gly Ala Gly Gly Pro Tyr Gly Pro Gly Gly Glu Gly Gly Pro Tyr
145                 150                 155                 160

Gly Pro Gly Gly Ser Tyr Gly Pro Gly Gly Ala Gly Pro Tyr Gly
                165                 170                 175

Pro Gly Gly Pro Tyr Gly Pro Gly Gly Glu Gly Pro Gly Ala Gly
                180                 185                 190

Gly Pro Tyr Gly Pro Gly Gly Val Gly Pro Gly Gly Gly Pro Gly
                195                 200                 205

Gly Tyr Gly Pro Gly Gly Ala Gly Pro Gly Gly Tyr Gly Pro Gly Gly
                210                 215                 220

Ser Gly Pro Gly Gly Tyr Gly Pro Gly Gly Ser Gly Pro Gly Gly Tyr
225                 230                 235                 240
```

Gly Pro Gly Gly Ser Gly Pro Gly Tyr Gly Pro Gly Gly Ser Gly
                245                 250                 255

Pro Gly Gly Tyr Gly Pro Gly Gly Ser Gly Pro Gly Gly Ser Gly Pro
                260                 265                 270

Gly Gly Tyr Gly Pro Gly Gly Ser Gly Pro Gly Gly Ser Gly Pro Gly
                275                 280                 285

Gly Tyr Gly Pro Gly Gly Ser Gly Pro Gly Gly Tyr Gly Pro Gly Gly
                290                 295                 300

Ser Gly Pro Gly Gly Ser Gly Pro Gly Gly Tyr Gly Pro Gly Gly Ser
305                 310                 315                 320

Gly Pro Gly Gly Ser Gly Pro Gly Gly Tyr Gly Pro Gly Gly Ser Gly
                325                 330                 335

Pro Gly Gly Phe Gly Pro Gly Gly Phe Gly Pro Gly Gly Ser Gly Pro
                340                 345                 350

Gly Gly Tyr Gly Pro Gly Gly Ser Gly Pro Gly Gly Ala Gly Pro Gly
                355                 360                 365

Gly Val Gly Pro Gly Gly Phe Gly Pro Gly Gly Ala Gly Pro Gly Gly
                370                 375                 380

Ala Gly Pro Gly Gly Ala Gly Pro Gly Gly Ala Gly Pro Gly Gly Ala
385                 390                 395                 400

Gly Pro Gly Gly Ala Gly Pro Gly Gly Ala Gly Pro Gly Gly Ala Gly
                405                 410                 415

Pro Gly Gly Ala Gly Ala Gly Gly Ala Gly Gly Ala Gly Gly Ser
                420                 425                 430

Gly Gly Ala Gly Gly Ser Gly Gly Thr Thr Ile Ile Glu Asp Leu Asp
                435                 440                 445

Ile Thr Ile Asp Gly Ala Asp Gly Pro Ile Thr Ile Ser Glu Glu Leu
        450                 455                 460

Thr Ile Ser Ala Tyr Tyr Pro Ser Ser Arg Val Pro Asp Met Val Asn
465                 470                 475                 480

Gly Ile Met Ser Ala Met Gln Gly Ser Gly Phe Asn Tyr Gln Met Phe
                485                 490                 495

Gly Asn Met Leu Ser Gln Tyr Ser Ser Gly Ser Gly Thr Cys Asn Pro
                500                 505                 510

Asn Asn Val Asn Val Leu Met Asp Ala Leu Leu Ala Ala Leu His Cys
                515                 520                 525

Leu Ser Asn His Gly Ser Ser Ser Phe Ala Pro Ser Pro Thr Pro Ala
                530                 535                 540

Ala Met Ser Ala Tyr Ser Asn Ser Val Gly Arg Met Phe Ala Tyr
545                 550                 555

<210> SEQ ID NO 27
<211> LENGTH: 252
<212> TYPE: PRT
<213> ORGANISM: Artificial Sequence
<220> FEATURE:
<223> OTHER INFORMATION: Collagen-type4-Kai

<400> SEQUENCE: 27

Met His His His His His Ser Ser Gly Ser Ser Lys Asp Gly Val
1               5                   10                  15

Pro Gly Phe Pro Gly Ser Glu Gly Val Lys Gly Asn Arg Gly Phe Pro
                20                  25                  30

Gly Leu Met Gly Glu Asp Gly Ile Lys Gly Gln Lys Gly Asp Ile Gly
                35                  40                  45

```
Pro Pro Gly Phe Arg Gly Pro Thr Glu Tyr Tyr Asp Thr Tyr Gln Glu
    50                  55                  60

Lys Gly Asp Glu Gly Thr Pro Gly Pro Pro Gly Pro Arg Gly Ala Arg
 65                  70                  75                  80

Gly Pro Gln Gly Pro Ser Gly Pro Pro Gly Val Pro Gly Ser Pro Gly
                 85                  90                  95

Ser Ser Arg Pro Gly Leu Arg Gly Ala Pro Gly Trp Pro Gly Leu Lys
                100                 105                 110

Gly Ser Lys Gly Glu Arg Gly Arg Pro Gly Lys Asp Ala Met Gly Thr
            115                 120                 125

Pro Gly Ser Pro Gly Cys Ala Gly Ser Pro Gly Leu Pro Gly Ser Pro
        130                 135                 140

Gly Pro Pro Gly Pro Pro Gly Asp Ile Val Phe Arg Lys Gly Pro Pro
145                 150                 155                 160

Gly Asp His Gly Leu Pro Gly Tyr Leu Gly Ser Pro Gly Ile Pro Gly
                165                 170                 175

Val Asp Gly Pro Lys Gly Glu Pro Gly Leu Leu Cys Thr Gln Cys Pro
            180                 185                 190

Tyr Ile Pro Gly Pro Pro Gly Leu Pro Gly Leu Pro Gly Leu His Gly
        195                 200                 205

Val Lys Gly Ile Pro Gly Arg Gln Gly Ala Ala Gly Leu Lys Gly Ser
210                 215                 220

Pro Gly Ser Pro Gly Asn Thr Gly Leu Pro Gly Phe Pro Gly Phe Pro
225                 230                 235                 240

Gly Ala Gln Gly Asp Pro Gly Leu Lys Gly Glu Lys
                245                 250

<210> SEQ ID NO 28
<211> LENGTH: 310
<212> TYPE: PRT
<213> ORGANISM: Artificial Sequence
<220> FEATURE:
<223> OTHER INFORMATION: Resilin-Kai

<400> SEQUENCE: 28

Met His His His His His Pro Glu Pro Val Asn Ser Tyr Leu
 1               5                  10                  15

Pro Pro Ser Asp Ser Tyr Gly Ala Pro Gly Gln Ser Gly Pro Gly Gly
                 20                  25                  30

Arg Pro Ser Asp Ser Tyr Gly Ala Pro Gly Gly Asn Gly Gly Arg
            35                  40                  45

Pro Ser Asp Ser Tyr Gly Ala Pro Gly Gln Gly Gln Gly Gln Gly Gln
 50                  55                  60

Gly Gln Gly Gly Tyr Ala Gly Lys Pro Ser Asp Ser Tyr Gly Ala Pro
 65                  70                  75                  80

Gly Gly Gly Asp Gly Asn Gly Gly Arg Pro Ser Ser Ser Tyr Gly Ala
                 85                  90                  95

Pro Gly Gly Gly Asn Gly Gly Arg Pro Ser Asp Thr Tyr Gly Ala Pro
                100                 105                 110

Gly Gly Gly Asn Gly Gly Arg Pro Ser Asp Thr Tyr Gly Ala Pro Gly
            115                 120                 125

Gly Gly Gly Asn Gly Asn Gly Arg Pro Ser Ser Ser Tyr Gly Ala
        130                 135                 140

Pro Gly Gln Gly Gln Gly Asn Gly Asn Gly Gly Arg Pro Ser Ser Ser
145                 150                 155                 160
```

```
Tyr Gly Ala Pro Gly Gly Asn Gly Gly Arg Pro Ser Asp Thr Tyr
            165                 170                 175

Gly Ala Pro Gly Gly Asn Gly Gly Arg Pro Ser Asp Thr Tyr Gly
            180                 185                 190

Ala Pro Gly Gly Asn Asn Gly Gly Arg Pro Ser Ser Ser Tyr Gly
            195                 200                 205

Ala Pro Gly Gly Asn Gly Gly Arg Pro Ser Asp Thr Tyr Gly Ala
            210                 215                 220

Pro Gly Gly Asn Gly Asn Gly Ser Gly Arg Pro Ser Ser Ser
225                 230                 235                 240

Tyr Gly Ala Pro Gly Gln Gly Gln Gly Gly Phe Gly Gly Arg Pro Ser
            245                 250                 255

Asp Ser Tyr Gly Ala Pro Gly Gln Asn Gln Lys Pro Ser Asp Ser Tyr
            260                 265                 270

Gly Ala Pro Gly Ser Gly Asn Gly Asn Gly Gly Arg Pro Ser Ser Ser
            275                 280                 285

Tyr Gly Ala Pro Gly Ser Gly Pro Gly Gly Arg Pro Ser Asp Ser Tyr
            290                 295                 300

Gly Pro Pro Ala Ser Gly
305                 310

<210> SEQ ID NO 29
<211> LENGTH: 282
<212> TYPE: PRT
<213> ORGANISM: Artificial Sequence
<220> FEATURE:
<223> OTHER INFORMATION: elastin short

<400> SEQUENCE: 29

Met His His His His His His Ser Ser Gly Ser Ser Leu Gly Val Ser
1               5                   10                  15

Ala Gly Ala Val Val Pro Gln Pro Gly Ala Gly Val Lys Pro Gly Lys
            20                  25                  30

Val Pro Gly Val Gly Leu Pro Gly Val Tyr Pro Gly Gly Val Leu Pro
            35                  40                  45

Gly Ala Arg Phe Pro Gly Val Gly Val Leu Pro Gly Val Pro Thr Gly
        50                  55                  60

Ala Gly Val Lys Pro Lys Ala Pro Gly Val Gly Gly Ala Phe Ala Gly
65                  70                  75                  80

Ile Pro Gly Val Gly Pro Phe Gly Gly Pro Gln Pro Gly Val Pro Leu
                85                  90                  95

Gly Tyr Pro Ile Lys Ala Pro Lys Leu Pro Gly Gly Tyr Gly Leu Pro
            100                 105                 110

Tyr Thr Thr Gly Lys Leu Pro Tyr Gly Tyr Gly Pro Gly Gly Val Ala
            115                 120                 125

Gly Ala Ala Gly Lys Ala Gly Tyr Pro Thr Gly Thr Gly Val Gly Pro
            130                 135                 140

Gln Ala Ala Ala Ala Ala Ala Lys Ala Ala Lys Phe Gly Ala
145                 150                 155                 160

Gly Ala Ala Gly Val Leu Pro Gly Val Gly Ala Gly Val Pro Gly
            165                 170                 175

Val Pro Gly Ala Ile Pro Gly Ile Gly Gly Ile Ala Gly Val Gly Thr
            180                 185                 190

Pro Ala Ala Ala Ala Ala Ala Ala Ala Lys Ala Ala Lys Tyr
            195                 200                 205
```

-continued

```
Gly Ala Ala Ala Gly Leu Val Pro Gly Gly Pro Gly Phe Gly Pro Gly
        210                 215                 220

Val Val Gly Val Pro Gly Ala Gly Val Pro Gly Val Gly Val Pro Gly
225                 230                 235                 240

Ala Gly Ile Pro Val Val Pro Gly Ala Gly Ile Pro Gly Ala Ala Val
                245                 250                 255

Pro Gly Val Val Ser Pro Glu Ala Ala Ala Lys Ala Ala Ala Lys Ala
                260                 265                 270

Ala Lys Tyr Gly Ala Arg Pro Gly Val Gly
                275                 280
```